US009024044B2

United States Patent
Koshiba et al.

(10) Patent No.: US 9,024,044 B2
(45) Date of Patent: May 5, 2015

(54) HETEROARYLCARBOXYLIC ACID ESTER DERIVATIVE

(75) Inventors: Takahiro Koshiba, Kawasaki (JP); Munetaka Tokumasu, Kawasaki (JP); Taisuke Ichimaru, Kawasaki (JP); Koji Ohsumi, Kawasaki (JP); Tadakiyo Nakagawa, Kawasaki (JP); Tatsuhiro Yamada, Kawasaki (JP); Kayo Matsumoto, Kawasaki (JP); Tamotsu Suzuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/517,805

(22) Filed: Jun. 14, 2012

(65) Prior Publication Data
US 2013/0338132 A1     Dec. 19, 2013

(51) Int. Cl.
*C07D 319/12*     (2006.01)

(52) U.S. Cl.
CPC .................................. *C07D 319/12* (2013.01)

(58) Field of Classification Search
CPC ..................................................... C07D 319/12
USPC .......................................................... 549/77
See application file for complete search history.

(56) References Cited

U.S. PATENT DOCUMENTS

| | | | |
|---|---|---|---|
| 4,563,527 A | 1/1986 | Fujii et al. | |
| 5,532,267 A | 7/1996 | Nakayama et al. | |
| 6,262,114 B1 | 7/2001 | Nakai et al. | |
| 6,358,960 B1 | 3/2002 | Senokuchi et al. | |
| 8,609,715 B2 * | 12/2013 | Konishi et al. | 514/448 |
| 2002/0128315 A1 | 9/2002 | Nakai et al. | |
| 2007/0298025 A1 | 12/2007 | Harosh et al. | |
| 2008/0009537 A1 | 1/2008 | Sakai | |
| 2010/0311690 A1 | 12/2010 | Harosh et al. | |
| 2012/0283222 A1 | 11/2012 | Konishi et al. | |
| 2014/0080790 A1 | 3/2014 | Konishi et al. | |

FOREIGN PATENT DOCUMENTS

| | | |
|---|---|---|
| JP | 61-022075 | 1/1986 |
| JP | 5-213927 | 8/1993 |
| JP | 8-143529 | 4/1996 |
| JP | 2008-266174 | 11/2008 |
| WO | WO 99/41231 A1 | 8/1999 |
| WO | WO 2006/050999 A2 | 5/2006 |
| WO | WO 2006/057152 A1 | 6/2006 |
| WO | WO 2009/071601 A1 | 6/2009 |
| WO | 2011/071048 | 6/2011 |
| WO | WO 2013/039187 A1 | 3/2013 |

OTHER PUBLICATIONS

Konishi et al DN 155:67824 (2011).*
Masashi Matsushima, et al."Inhibition of Enteropeptidase by Antitrypsin drugs", Biomedical Research 22 (5), 2001, pp. 257-260.
T. Yokoyama, et al., "Studies on new Synthetic Inhibitors of Kallikreins and Chymotrypsin", Advances in Experimental Medicine and Biology, 1989, 247(B), pp. 271-276.
International Search Report issued in PCT/JP2013/067015 on Sep. 10, 2013.
Written Opinion issued in PCT/JP2013/067015 on Sep. 10, 2013.
U.S. Appl. No. 14/098,774, filed Dec. 6, 2013, Suzuki, et al.

* cited by examiner

*Primary Examiner* — Noble Jarrell
*Assistant Examiner* — Raymond Covington
(74) *Attorney, Agent, or Firm* — Oblon, McClelland, Maier & Neustadt, L.L.P.

(57)     ABSTRACT

Compounds represented by the following formula (I), are useful as hyperglycemic inhibitors having a serine protease inhibitory action and as prophylactic or therapeutic drugs for diabetes.

8 Claims, No Drawings

HETEROARYLCARBOXYLIC ACID ESTER DERIVATIVE

BACKGROUND OF THE INVENTION

Field of the Invention

The present invention relates to novel compounds, heteroarylcarboxylic acid ester derivatives, which exhibit a serine protease (particularly trypsin and enteropeptidase) inhibitory activity. The present invention also relates to pharmaceutical compositions which contain such a compounds and drugs for the treatment or prophylaxis of diabetes. The present invention further relates to methods for the treatment and/or prophylaxis of diabetes by administering such a heteroarylcarboxylic acid ester derivative.

DISCUSSION OF THE BACKGROUND

At present, insulin secretagogues (sulfonylureas), glucose absorption inhibitors (α-glucosidase inhibitors), insulin sensitizers (biguanide, thiazolidine derivatives), and the like are clinically used as therapeutic drugs for diabetes. However, since all of them are accompanied by side effects such as hypoglycemia, diarrhea, lactic acidosis, edema, and the like; show an insufficient effect; and the like, a medicament satisfying clinical needs is still demanded.

In recent years, a benzoic acid ester having a protease inhibitory activity, which is represented by the following compound, has been reported to show a blood glucose elevation suppressing action in a diabetes animal model (see WO2006/057152, which is incorporated herein by reference in its entirety). The following compound is considered to show an enzyme inhibitory activity on trypsin, thrombin, pancreatic, and plasma kallikreins, plasmin and the like and a leukotriene receptor antagonistic action. Moreover, an enteropeptidase inhibitory activity of the following compound has also been reported (see Biomedical Research (2001), 22(5) 257-260, which is incorporated herein by reference in its entirety). However, many unclear points remain in the relationship between such actions and a blood glucose elevation suppressing action.

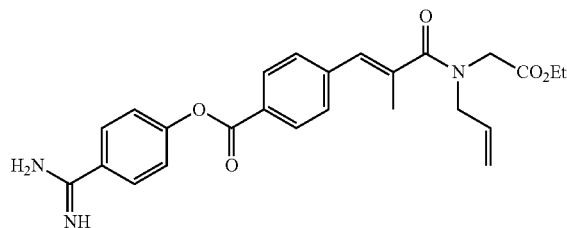 [SMILES: C=CCN(CC(=O)OCC)C(=O)/C(C)=C/c1ccc(C(=O)Oc2ccc(C(=N)N)cc2)cc1]

On the other hand, as for a heteroarylcarboxylic acid ester structures, JP-A-55-167275, which is incorporated herein by reference in its entirety, discloses a compound as a therapeutic drug for pancreatitis. In this document, only heteroarylcarboxylic acid ester compounds wherein the substituent of the heteroarylcarboxylic acid moiety is a methyl group or a methoxy group or unsubstituted compounds are disclosed, as represented by the following formula. While these compounds are disclosed as showing an inhibitory activity on trypsin, chymotrypsin and thrombin, no description is given as to the enteropeptidase inhibitory activity and blood glucose elevation suppressing action.

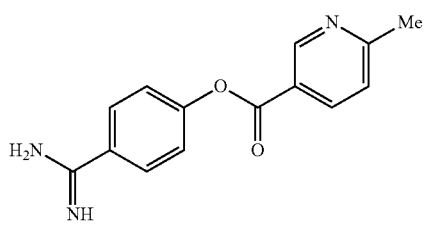 [SMILES: Cc1ccc(C(=O)Oc2ccc(C(=N)N)cc2)cn1]

In addition, Advances in Experimental Medicine and Biology (1989), 247B (Kinins 5, Pt. B), 271-6, which is incorporated herein by reference in its entirety, also describes a heteroarylcarboxylic acid ester having a protease inhibitory activity, which is represented by the following formula. However, only compounds wherein the heteroaryl moiety is unsubstituted are disclosed, and no description is given as to the enteropeptidase inhibitory activity and blood glucose elevation suppressing action of these compounds.

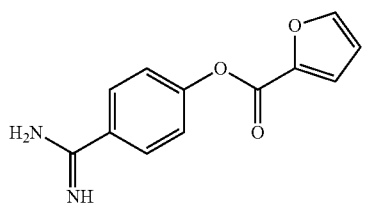 [SMILES: N=C(N)c1ccc(OC(=O)c2ccco2)cc1]

Furthermore, WO99/41231, which is incorporated herein by reference in its entirety, describes a compound represented by the following formula. However, it has a structure wherein an aryl group substituted by a carboxyl group is directly bonded to the heteroaryl moiety, which is completely different from the compound of the present invention. The document discloses an inhibitory activity against blood coagulation factor VIIa; however, no description is given as to the enteropeptidase inhibitory activity and blood glucose elevation suppressing action.

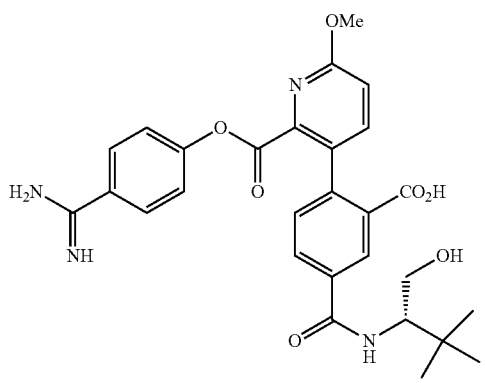 [SMILES: COc1ccc(-c2ccc(C(=O)N[C@H](CO)C(C)(C)C)cc2C(=O)O)c(C(=O)Oc2ccc(C(=N)N)cc2)n1]

On the other hand, trypsin is one of the intestinal serine proteases and is produced by degradation of inactive trypsinogen by enteropeptidase. Trypsin is known to activate various digestive enzymes by acting on chymotrypsinogen, proelastase, procarboxylesterase, procolipase and pro-sucrase-isomaltase, and the like. Therefore, it is considered that an inhibitor of enteropeptidase and trypsin lowers the digestive capacity for protein, lipid, and carbohydrates, and is effective as a drug for the treatment or prophylaxis of obesity and hyperlipidemia.

WO2006/050999, which is incorporated herein by reference in its entirety, describes that a medicament that inhibits both enteropeptidase and trypsin is interesting as a body fat-reducing agent. In addition, WO2009/071601, which is incorporated herein by reference in its entirety reports a compound which has an inhibitory activity against enteropeptidase, trypsin, plasmin, kallikrein, and the like as an antiobesity drug. However, neither of these publications describes suppression of blood glucose elevation and hypoglycemic effect afforded by simultaneous inhibition of enteropeptidase and trypsin, and the protease inhibitor described therein has a structure completely different from that of the compound of the present invention.

Accordingly, there remains a need for compounds which are useful for the treatment or prophylaxis of diabetes. Therefore, to further satisfy the clinical needs from the aspects of effect, safety and the like, a hyperglycemic inhibitor having a serine protease inhibitory action, which is a new drug for the treatment or prophylaxis of diabetes, is desired.

SUMMARY OF THE INVENTION

Accordingly, it is one object of the present invention to provide novel compounds which are useful for the treatment or prophylaxis of diabetes.

It is another object of the present invention to provide novel compounds which exhibit a serine protease inhibitory action.

It is another object of the present invention to provide novel serine protease (particularly trypsin and enteropeptidase) inhibitors.

It is another object of the present invention to provide novel hyperglycemic inhibitors or hypoglycemic agents, and further, drugs for the treatment and/or prophylaxis of any of diabetes, obesity, hyperlipidemia, diabetic complication, and metabolic syndrome.

It is another object of the present invention to provide novel methods for the treatment and/or prophylaxis of any of diabetes, obesity, hyperlipidemia, diabetic complication, and metabolic syndrome.

These and other objects, which will become apparent during the following detailed description, have been achieved by the inventors' discovery that the heteroarylcarboxylic acid ester derivatives described below have serine protease inhibitory activity and are useful for the treatment and/or prophylaxis of any of diabetes, obesity, hyperlipidemia, diabetic complication, and metabolic syndrome.

Thus, in view of the above-mentioned current situation, the present inventors have conducted intensive studies and considered that simultaneous inhibition of trypsin and enteropeptidase is particularly effective for the suppression of blood glucose elevation. They have synthesized various heteroarylcarboxylic acid ester derivatives, which are novel compounds, evaluated trypsin and enteropeptidase inhibitory activity, and found that certain heteroarylcarboxylic acid ester derivatives are protease inhibitors that simultaneously inhibit them. Furthermore, they have also found that such representative compounds show a blood glucose elevation suppressing effect in diabetes animal model.

Accordingly, the present invention provides a compound represented by the following formula (I):

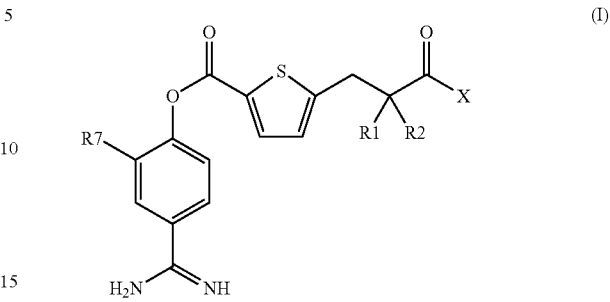

wherein $R^1$ and $R^2$ are the same or different and each is independently a $C_{1-4}$ alkyl group, a $C_{2-4}$ alkenyl group, or $R^1$ and $R^2$ together with the carbon atoms to which they are bonded form a $C_{3-8}$ cycloalkyl group;

X is $-OR^3$, $-NR^4R^5$ or formula (II):

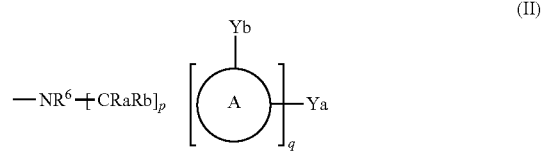

$R^3$ is a hydrogen atom or a $C_{1-4}$ alkyl group;

$R^4$, $R^5$ and $R^6$ are the same or different and each is independently a hydrogen atom, a $C_{1-8}$ alkyl, carboxyl $C_{1-8}$ alkyl, or $C_{3-8}$ alkenyl group, or $R^4$ and $R^5$ together with the nitrogen to which they are bonded form a $C_{3-9}$ heterocyclic group, wherein said $C_{1-8}$ alkyl group, said $C_{3-8}$ alkenyl group, and said $C_{3-9}$ heterocyclic group may be substituted with one or more substituents;

Ra and Rb are the same or different and each is independently a hydrogen atom, a $C_{1-8}$ alkyl, carboxyl $C_{1-8}$ alkyl, carboxyl, aryl, $C_{3-6}$ heterocyclic group containing 1 to 4 heteroatoms selected from the group of O, N, and S, or a $C_{3-8}$ cycloalkyl group, or Ra and Rb together with the atom to which they are bonded form $C_{3-8}$ cycloalkyl or a $C_{3-9}$ heterocyclic group containing 1-4 heteroatoms selected from the group of O, N and S, wherein said $C_{1-8}$ alkyl group, said aryl group, said $C_{3-8}$ cycloalkyl group, and said $C_{3-9}$ heterocyclic group may be substituted with one or more substituents;

A is an aryl or $C_{3-6}$ heterocyclic group containing 1-4 heteroatoms selected from the group of O, N, and S, or a $C_{3-8}$ cycloalkyl group;

Ya is a hydrogen atom, a halogen atom, a carboxyl, hydroxyl, carbonyl, carboxyl $C_{1-3}$ alkyl, or sulfo group;

Yb is a hydrogen atom, a halogen atom, a carboxyl, hydroxyl, carbonyl, carboxyl $C_{1-3}$ alkyl, nitro, cyano or $C_{1-3}$ alkoxyl group;

p is 0, 1, 2, 3, or 4;

q is 0 or 1;

$R^7$ is a hydrogen atom, a halogen atom, or a nitro group;

with the proviso that when $R^1$ and $R^2$ are both methyl, then neither of $R^4$ and $R^5$ are an ethyl group substituted with two carboxyl groups, and when $R^1$ and $R^2$ are both methyl, then the group represented by formula (II) is not a group of:

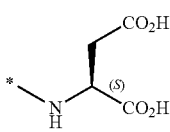

or a pharmaceutically acceptable salt thereof.

The present invention also provides a compound represented by the aforementioned formula (I), in which X is —NR$^4$R$^5$ or formula (II), wherein R$^4$, R$^5$ and R$^6$ are each independently a hydrogen atom or a C$_{1-8}$ alkyl group, or a pharmaceutically acceptable salt thereof.

The present invention also provides a compound represented by the aforementioned formula (I), wherein X is NR$^4$R$^5$, wherein R$^4$ and R$^5$ together with the nitrogen to which they are bonded form a C$_{3-9}$ heterocyclic group substituted by a hydrogen atom, a carboxyl, carboxyl C$_{1-3}$ alkyl, hydroxyl group or a halogen atom, or a pharmaceutically acceptable salt thereof.

The present invention also provides a compound represented by the aforementioned formula (I), wherein X is formula (II), wherein p=1 or 2, and q=0, or a pharmaceutically acceptable salt thereof.

The present invention also provides a compound represented by the aforementioned formula (I), wherein X is formula (II), wherein p=0 and q=1, or a pharmaceutically acceptable salt thereof.

The present invention also provides a compound represented by the aforementioned formula (I), wherein X is formula (II), wherein p=1, q=1, and Ra and Rb are the same or different and each is independently a hydrogen atom, a C$_{1-8}$ alkyl group, or Ra and Rb together with the atom to which they are bonded form a C$_{3-8}$ cycloalkyl group, wherein said C$_{1-8}$ alkyl group and said C$_{3-8}$ cycloalkyl group may substituted with a group selected from a hydrogen atom, a carboxyl, carbamoyl, hydroxyl, phenyl and C$_{3-8}$ cycloalkyl group, or a pharmaceutically acceptable salt thereof.

The present invention also provides a compound represented by the aforementioned formula (I), wherein R$^1$ and R$^2$ are the same or different and each is independently a methyl, ethyl, or propyl group, or R$^1$ and R$^2$ together with the carbon atoms to which they are bonded form a cyclobutyl or cyclopentyl group, or a pharmaceutically acceptable salt thereof.

The present invention also provides a compound represented by the aforementioned formula (I), X is formula (II), wherein q=1, and A is phenyl, pyridyl or C$_{1-6}$ heterocyclic group containing 1-4 oxygen atom(s), or a pharmaceutically acceptable salt thereof.

The present invention also provides a compound represented by the aforementioned formula (I), wherein q=1, Ya is a carboxyl, carboxyl C$_{1-3}$ alkyl, hydroxyl, sulfo, carbonyl group, or a halogen atom; and Yb is a hydrogen atom, a carboxyl, hydroxyl group or a halogen atom, or a pharmaceutically acceptable salt thereof.

The present invention also provides a compound represented by the aforementioned formula (I), wherein X is —NR$^4$R$^5$, wherein when R$^4$ or R$^5$ have a substituent, said substituent is selected from selected from the group consisting of a carboxyl, hydroxyl, carboxyl C$_{1-3}$ alkyl, C$_{3-8}$ alkenyl, carbamoyl, phenyl, amino, sulfo, cyano, C$_{3-8}$ cycloalkyl group, a halogen atom, and a C$_{1-8}$ heterocyclic group containing 1 to 4 heteroatoms selected from the group consisting of O, N, and S, or a pharmaceutically acceptable salt thereof.

The present invention also provides a compound represented by the aforementioned formula (I), wherein X is formula (II), wherein, when Ra or Rb has a substituent, said substituent is selected from the group consisting of a carboxyl, hydroxyl, phenyl, amino, methylthio, thiol, carbamoyl, guanidino, C$_{3-8}$ cycloalkyl, and C$_{1-8}$ heterocyclic group containing 1-4 heteroatoms selected from the group consisting of O, N and S, or a pharmaceutically acceptable salt thereof.

Further, the present invention provides pharmaceutical compositions comprising the above-mentioned compound, or a pharmaceutically acceptable salt thereof as an active ingredient.

The present invention also provides an intestinal serine protease inhibitor, comprising the above-mentioned compound, or a pharmaceutically acceptable salt thereof as an active ingredient.

The present invention also provides a dual inhibitor of trypsin and enteropeptidase, comprising the above-mentioned compound, or a pharmaceutically acceptable salt thereof as an active ingredient.

The present invention also provides a hyperglycemic inhibitor or hypoglycemic agent, comprising the above-mentioned compound, or a pharmaceutically acceptable salt thereof as an active ingredient.

The present invention also provides a prophylactic or therapeutic drug for diabetes, comprising the above-mentioned compound, or a pharmaceutically acceptable salt thereof as an active ingredient.

The present invention also provides an insulin sensitizer comprising the above-mentioned compound, or a pharmaceutically acceptable salt thereof as an active ingredient.

The present invention also provides a prophylactic or therapeutic drug for obesity, hyperlipidemia, diabetic complication, or metabolic syndrome, comprising the above-mentioned compound, or a pharmaceutically acceptable salt thereof as an active ingredient.

The present invention also provides a method for preventing or treating diabetes, comprising administering an effective amount of the above-mentioned compound, or a pharmaceutically acceptable salt thereof.

The present invention also provides a method for improving insulin resistance, comprising administering an effective amount of the above-mentioned compound, or a pharmaceutically acceptable salt thereof.

The present invention also provides a method for preventing or treating obesity, hyperlipidemia, diabetic complication or metabolic syndrome, comprising administering an effective amount of the above-mentioned compound, or a pharmaceutically acceptable salt thereof.

The present invention also provides use of the above-mentioned compound, or a pharmaceutically acceptable salt thereof for the prophylaxis or treatment of diabetes.

The present invention also provides use of the above-mentioned compound, or a pharmaceutically acceptable salt thereof for the improvement of insulin resistance.

The present invention also provides use of the above-mentioned compound, or a pharmaceutically acceptable salt thereof for the prophylaxis or treatment of obesity, hyperlipidemia, diabetic complication or metabolic syndrome.

The compound of the present invention has a blood glucose elevation suppressing action and can be preferably used as a drug for the treatment or prophylaxis of diabetes.

DETAILED DESCRIPTION OF THE PREFERRED EMBODIMENTS

The present invention is explained in detail in the following.

In the present specification, the phrase "may be substituted" or "optionally having substituent(s)" means "being substituted or unsubstituted". Unless otherwise specified, the position and number of the substituents may be any, and are not particularly limited. When substituted by two or more substituents, the substituents may be the same or different. Examples of the substituent include a nitro group, a halogen atom, a cyano group, a hydroxyl group, a thiol group, an amino group, a guanidino group, a formyl group, a phenyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and the like.

In the present specification, examples of the substituent of the "aryl group optionally having substituent(s)" and "heterocyclic group optionally having substituent(s)" include a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, and the like.

The "cyclic amino group" in the present specification is a saturated or unsaturated cyclic amino group having a carbon number of 2 to 7, which may contain one or more hetero atoms in the ring, such as a nitrogen atom, an oxygen atom, a sulfur atom, and the like. For example, a pyrrolidinyl group, a pyrrolinyl group, a piperidinyl group, a morpholinyl group, a piperazinyl group, a thiomorpholinyl group, a piperidinonyl group, a piperazinonyl group, and the like can be mentioned.

The term "lower" in, for example, a lower alkyl group in the present specification indicates that the group has 1 to 6 carbon atoms, preferably 1 to 4 carbon atoms, and more preferably, 1 to 3 carbon atoms, unless otherwise specified.

The "alkyl group" is a straight chain or branched chain or cyclic alkyl group, preferably, having a carbon number of 1 to 10. For example, a methyl group, an ethyl group, an n-propyl group, an n-butyl group, an n-pentyl group, an n-hexyl group, an isopropyl group, an isobutyl group, a sec-butyl group, a tert-butyl group, an isopentyl group, a tert-pentyl group, a neopentyl group, a 2-pentyl group, a 3-pentyl group, a 2-hexyl group, a cyclopropyl group, a cyclopentyl group, and the like can be mentioned.

The "alkenyl group" is a straight chain or branched chain alkenyl group, preferably, having a carbon number of 2 to 10, which includes each isomer. For example, a vinyl group, an allyl group, a propenyl group, a butenyl group, a pentenyl group, a hexenyl group, and the like can be mentioned.

The "alkynyl group" is a straight chain or branched chain alkynyl group having a carbon number of 2 to 10, which includes each isomer. For example, an ethynyl group, a 1-propynyl group, a 2-propynyl group, a 2-butynyl group, a 3-butynyl group, a pentynyl group, and the like can be mentioned.

Examples of the "halogen atom" include a fluorine atom, a chlorine atom, a bromine atom, an iodine atom, and the like.

The "acyl group" is an acyl group having a straight chain or branched chain or cyclic alkyl group or alkenyl group having a carbon number of 1 to 10, preferably, 1 to 8, more preferably, 1 to 6. For example, an acetyl group, a propionyl group, a butyryl group, an isobutyryl group, a valeryl group, an isovaleryl group, a pivaloyl group, a hexanoyl group, an acryloyl group, a methacryloyl group, a crotonoyl group, an isocrotonoyl group, a cyclopropanoyl group, a cyclobutanoyl group, a cyclopentanoyl group, a cyclohexanoyl group, and the like can be mentioned.

The "alkoxy group" is an alkoxyl group having a straight chain or branched chain or cyclic alkyl group having a carbon number of 1 to 10, preferably, 1 to 8, more preferably, 1 to 6, and further more preferably 1 to 3. For example, a methoxy group, an ethoxy group, an n-propoxy group, an n-butoxy group, an n-pentyloxy group, an n-hexyloxy group, an isopropoxy group, an isobutoxy group, a sec-butoxy group, a tert-butoxy group, a cyclopropyloxy group, a cyclobutyloxy group, a cyclopentyloxy group, and a cyclohexyloxy group can be mentioned.

The "alkylthio group" is an alkylthio group having a straight chain or branched chain or cyclic alkyl group having a carbon number of 1 to 10, preferably, 1 to 8, more preferably, 1 to 6. For example, a methylthio group, an ethylthio group, an n-propylthio group, an isopropylthio group, an n-butylthio group, an isobutylthio group, a sec-butylthio group, a tert-butylthio group, a cyclopropylthio group, a cyclobutylthio group, a cyclopentylthio group, a cyclobutylthio group, and the like can be mentioned.

The "alkylamino group" is an amino group mono- or di-substituted by the aforementioned "alkyl group", preferably, "lower alkyl group". For example, a methylamino group, an ethylamino group, a propylamino group, an isopropylamino group, a dimethylamino group, a diethylamino group, a dipropylamino group, a diisopropylamino group, an ethylmethylamino group and the like can be mentioned.

The "acyloxy group" is a group wherein an oxygen atom is bonded to the carbon of the carbonyl moiety of the aforementioned "acyl group", preferably, "lower acyl group". For example, an acetyloxy group, a propionyloxy group, a butyryloxy group, an isobutyryloxy group, a valeryloxy group, an isovaleryloxy group, a pivaloyloxy group, a hexanoyloxy group, an acryloyloxy group, a methacryloyloxy group, a crotonoyloxy group, an isocrotonoyloxy group, and the like can be mentioned.

The "acylamino group" is a group wherein a nitrogen atom is bonded to the carbon of the carbonyl moiety of the aforementioned "acyl group", preferably, "lower acyl group". For example, an acetylamino group, a propionylamino group, a butyrylamino group, an isobutyrylamino group, a valerylamino group, an isovalerylamino group, a pivaloylamino group, a hexanoylamino group, an acryloylamino group, a methacryloylamino group, a crotonoylamino group, an isocrotonoylamino group, and the like can be mentioned.

The "alkoxycarbonyl group" is a carbonyl group having the aforementioned "alkoxyl group", preferably, "lower alkoxyl group". For example, a methoxycarbonyl group, an ethoxycarbonyl group, a propoxycarbonyl group, an isopropoxycarbonyl group, an n-butoxycarbonyl group, an isobutoxycarbonyl group, a sec-butoxycarbonyl group, a tert-butoxycarbonyl group, and the like can be mentioned.

The "alkylcarbamoyl group" is a group wherein a nitrogen atom of the aforementioned "alkylamino group" or "cyclic amino group", and a carbon atom of the carbonyl group are bonded. For example, an N-methylcarbamoyl group, an N-ethylcarbamoyl group, an N,N-dimethylcarbamoyl group, a 1-pyrrolidinylcarbonyl group, a 1-piperidinylcarbonyl group, a 4-morpholinylcarbonyl group, and the like can be mentioned.

The "alkylsulfonylamino group" is a group wherein a nitrogen atom is bonded to a sulfonyl group wherein the aforementioned "alkyl group", preferably, "lower alkyl group" is bonded to a sulfur atom. For example, a methylsulfonylamino group, an ethylsulfonylamino group, a propylsulfonylamino group, an isopropylsulfonylamino group, a butylsulfonylamino group, an isobutylsulfonylamino group, and the like can be mentioned.

The "arylsulfonylamino group" is a group wherein a nitrogen atom is bonded to a sulfur atom of a sulfonyl group substituted by an aryl group. For example, a phenylsulfonylamino group, a naphthylsulfonylamino group, and the like can be mentioned.

Examples of the "aryl group" include an aryl group having a carbon number of 6 to 14 such as a phenyl group, a naphthyl group, and the like.

The "heterocyclic group" is a 5- to 14-membered monocyclic to tricyclic heterocyclic group containing, as a ring atom, 1 to 4 hetero atoms selected from an oxygen atom, a sulfur atom, and a nitrogen atom. Any carbon atom as a ring atom may be substituted by an oxo group, and a sulfur atom or a nitrogen atom may be oxidized to form an oxide. In addition, it may be condensed with a benzene ring. For example, a pyridyl group, a pyridazinyl group, a pyrimidinyl group, a pyrazinyl group, a furyl group, a thienyl group, a pyrrolyl group, an isoxazolyl group, an oxazolyl group, an isothiazolyl group, a thiazolyl group, a pyrazolyl group, an imidazolyl group, an oxadiazolyl group, a thiadiazolyl group, a triazolyl group, a tetrazolyl group, a benzofuranyl group, a benzothienyl group, an indolyl group, an isoindolyl group, a benzoxazolyl group (=a benzooxazolyl group), a benzothiazolyl group, a benzimidazolyl group (=a benzoimidazolyl group), an indazolyl group, a benzisoxazolyl group, a benzisothiazolyl group, a benzofurazanyl group, a benzothiadiazolyl group, a purinyl group, a quinolinyl group, an isoquinolyl group, a cinnolinyl group, a phthalazinyl group, a quinazolinyl group, a quinoxalinyl group, a pteridinyl group, an imidazooxazolyl group, an imidazothiazolyl group, an imidazoimidazolyl group, a dibenzofuranyl group, a dibenzothienyl group, a carbazolyl group, an acridinyl group, a pyrrolidinyl group, a pyrazolidinyl group, an imidazolidinyl group, a pyrrolinyl group, a pyrazolinyl group, an imidazolinyl group, a tetrahydrofuranyl group, a tetrahydrothiophenyl group, a thiazolidinyl group, a piperidinyl group, a piperazinyl group, a quinuclidinyl group, a tetrahydropyranyl group, a tetrahydrothiopyranyl group, a morpholinyl group, a thiomorpholinyl group, a dioxolanyl group, a homopiperidinyl group, a homopiperazinyl group, an indolinyl group, an isoindolinyl group, a chromanyl group, an isochromanyl group, a tetrahydronaphthyridinyl group, an azaindolyl group, and the like can be mentioned. Preferably, a thiadiazolyl group, an imidazolyl group, a tetrazolyl group, a piperidinyl group, a piperazinyl group, a thiazolidinyl group, and the like can be mentioned.

The "serine protease" in the present specification is a protease having, as a catalytic residue, a serine residue having nucleophilicity. For example, trypsin, chymotrypsin, elastase, enteropeptidase, kallikrein, thrombin, factor Xa, and tryptase, and the like can be mentioned. In addition, the term "serine protease inhibition" in the present specification means a decrease or disappearance of the aforementioned serine protease activity. Preferably, it is an inhibition of the activity of intestinal serine proteases such as trypsin, enteropeptidase, chymotrypsin, elastase and the like, particularly preferably inhibition of trypsin and enteropeptidase activities.

The serine protease inhibitor of the present invention is a dual inhibitor that simultaneously inhibits at least trypsin and enteropeptidase.

The diabetes in the present specification means type I diabetes mellitus and type II diabetes mellitus, with preference given to type II diabetes mellitus.

In the present invention, the compound represented by the formula (I) or a pharmaceutically acceptable salt thereof is preferably as follows.

In the formula (I), preferably, $R^1$ and $R^2$ may be the same or different from each other and, preferably, each is independently a linear or branched $C_{1-4}$ alkyl group, or $R^1$ and $R^2$ together with the carbon atom to which they are bonded form a $C_{3-5}$ cycloalkyl group, specifically, a cyclobutyl group, a cyclopentyl group and the like. More preferably $R^1$ and $R^2$ are independently a $C_{1-3}$ alkyl group, particularly extremely preferably a methyl and ethyl group and the like.

In other aspect, it is also preferable that $R^1$ and $R^2$ are the same.

In the formula (I), X is preferably —$OR^3$, —$NR^4R^5$, or the group represented by the formula (II) above, more preferably, —$NR^4R^5$ or a group represented by the formula (II), further more preferably, a group represented by the formula (II).

In the formula (I), $R^7$ is preferably a hydrogen atom, a halogen atom, such as fluorine atom or chlorine atom, more preferably, a fluorine atom. The structure-activity relationship for the variation on this substituent is well-supported by the previous application by the present inventors, WO2011/071048, which is incorporated herein by reference in its entirety.

In the group —$OR^3$, $R^3$ is preferably a hydrogen atom.

In the group —$NR^4R^5$, preferably $R^4$ and $R^5$ are independently a hydrogen atom, a $C_{1-8}$ alkyl group, carboxyl $C_{1-8}$ alkyl or a $C_{3-8}$ alkenyl group, more preferably, a $C_{1-3}$ alkyl or carboxyl $C_{1-3}$ alkyl group, wherein said $C_{1-8}$ alkyl group, said carboxyl $C_{1-8}$ alkyl group, said $C_{3-8}$ alkenyl group, said $C_{1-3}$ alkyl group, and said carboxyl $C_{1-3}$ alkyl group may be substituted with one or more substituents.

In the formula (II), preferably $R^6$ is a hydrogen atom, a $C_{1-8}$ alkyl or $C_{3-8}$ alkenyl group, more preferably, a hydrogen atom or a $C_{1-3}$ alkyl group, said $C_{1-8}$ alkyl group, wherein said $C_{3-8}$ alkenyl group and said $C_{1-3}$ alkyl group may be substituted with one or more substituents.

In the formula (II), Ra and Rb may be the same or different from each other and, preferably, each is independently a hydrogen atom, a phenyl, $C_{1-8}$ alkyl, carboxyl, or carboxyl $C_{1-8}$ alkyl group, more preferably, a hydrogen atom or a $C_{1-3}$ alkyl group, wherein said phenyl group, said $C_{1-8}$ alkyl group, said carboxyl $C_{1-8}$ alkyl group and said $C_{1-3}$ alkyl group may be substituted with one or more substituents.

In the formula (II), when Ra and Rb form ring, said ring is preferably a cyclopropyl, cyclobutyl group or cyclopentyl which may have substituents.

In the formula (II), A is preferably a phenyl, pyridyl, or $C_{3-6}$ heterocyclic group containing 1 to 4 oxygen atoms, more preferably, a phenyl or pyridyl group, even more preferably, a phenyl group.

In the formula (II), Ya is preferably a carboxyl, carboxyl $C_{1-3}$ alkyl, hydroxyl, sulfo group, a halogen atom, or a carbonyl group, more preferably, a carboxyl, carboxyl $C_{1-3}$ alkyl, hydroxyl group or a halogen atom, even more preferably, a carboxyl or carboxyl $C_{1-3}$ alkyl group.

In the formula (II), Yb is preferably a hydrogen atom, a carboxyl, hydroxyl group, or a halogen atom, more preferably, a carboxyl or hydroxyl group.

In the formula (II), p is preferably 0, 1, 2, 3, or 4, more preferably, 0, 1, 2, or 3, further more preferably, 0, 1, or 2.

In the formula (II), q is preferably 0 or 1, more preferably, 1.

In the formula (II), preferable combinations of p and q are when p=1 or 2, and q=0, and when p=0 or 1, and q=1, further preferable combinations are when p=1 or 2, and q=0, or when p=0 and q=1.

Here, when a group represented by $R^4$ or $R^5$ has a substituent, examples of the substituent include a nitro group, a halogen atom, a cyano group, a hydroxyl group, a thiol group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally having substituent(s), a cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group optionally having substituent(s), an aralkylthio group optionally having substituent(s), a heterocyclic group optionally having substituent(s), a heterocyclic oxy group optionally having substituent(s), a heterocyclic thio group optionally having substituent(s), an oxo group, and the like. A halogen atom, a hydroxyl group, a carboxyl group, a sulfo group, a cyano group, a phosphono group, a lower alkoxycarbonyl group, an aryl group optionally having substituent(s), a heterocyclic group optionally having substituent(s), an oxo group, and the like are preferable, and a hydroxyl group, a carboxyl group, a sulfo group, a lower alkoxycarbonyl group, and the like are particularly preferable. A carboxyl group, a hydroxyl group, a carboxyl $C_{1-3}$ alkyl group, a $C_{3-8}$ alkenyl group, a halogen atom, a carbamoyl group, a phenyl group, an amino group, a sulfo group, a cyano group, $C_{3-8}$ cycloalkyl group, and a $C_{1-8}$ heterocyclic group containing 1-4 heteroatoms selected from the group consisting of O, N, and S, and the like are also preferable. As for the $C_{1-8}$ heterocyclic group containing 1-4 heteroatoms, a tetrazolyl group, a 2,4-dioxo-1,3-thiazolidinyl group, and the like can be preferably mentioned. The number of the substituents is preferably 1 to 3, more preferably 1 or 2.

As a cyclic amino group formed by $R^4$ and $R^5$ bonded to each other, an aziridinyl group, an azetidinyl group, a pyrrolidinyl group, a piperidinyl group a tetrahydroquinolinyl, and the like are preferable.

When the cyclic amino group formed by $R^4$ and $R^5$ bonded to each other has a substituent, examples of the substituent include a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, an oxo group, and the like. A carboxyl group, a hydroxyl group, a carboxyl $C_{1-3}$ alkyl group, a $C_{3-8}$ alkenyl group, a halogen atom, a carbamoyl group, a phenyl group, an amino group, a sulfo group, a sulfo group, and a heterocyclic group containing 1-4 heteroatoms selected from the group consisting of O, N, and S, and the like are preferable. As for the $C_{1-8}$ heterocyclic group containing 1-4 heteroatoms, a tetrazolyl group, a 2,4-dioxo-1,3-thiazolidinyl group, and the like can be preferably mentioned. A hydroxyl group, a carboxyl group, a sulfo group, a phosphono group, a lower alkoxycarbonyl group, and the like are also preferable. The number of the substituents is preferably 1 to 3, more preferably 1 or 2.

Here, when a group represented by Ra or Rb has a substituent, examples of the substituent include a nitro group, a halogen atom, a cyano group, a hydroxyl group, a thiol group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally having substituent(s), a cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group optionally having substituent(s), an aralkylthio group optionally having substituent(s), a heterocyclic group optionally having substituent(s), a heterocyclic oxy group optionally having substituent(s), a heterocyclic thio group optionally having substituent(s), an oxo group, and the like. A carboxyl group, a hydroxyl group, a phenyl group, an amino group, a lower alkylthio group, a thiol group, a carbamoyl group, a guanidino group, $C_{3-8}$ cycloalkyl group, $C_{1-8}$ heterocyclic group containing 1 to 4 heteroatoms selected from O, N, and S, and the like are preferable, and a hydroxyl group, a carboxyl group, a sulfo group, a lower alkoxycarbonyl group, a 1H-tetraazolyl group, and the like are particularly preferable.

As a cycloalkyl group formed by Ra and Rb bonded to each other, a cyclopropyl group, a cyclobutyl group, a cyclopentyl, and the like are preferable.

As a heterocyclic group formed by Ra and Rb bonded to each other, a tetrahydrofuranyl group, a pyrrolidinyl group, and the like are preferable.

When the cycloalkyl group or heterocyclic group formed by Ra and Rb bonded to each other has a substituent, examples of the substituent include a nitro group, a halogen atom, a cyano group, a hydroxyl group, a thiol group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, an oxo group, and the like. A carboxyl group, a hydroxyl group, an oxo group, a phenyl group, an amino group, a lower alkylthio group, a thiol group, a carbamoyl group, a guanidino group, $C_{3-8}$ heterocyclic group containing 1 to 4 heteroatoms selected from O, N, and S, a $C_{3-8}$ cycloalkyl group, and the like are preferable. The number of the substituents is preferably 1 to 3, more preferably 1 or 2.

A compound represented by any of the following formulas or a pharmaceutically acceptable salt thereof is preferable.

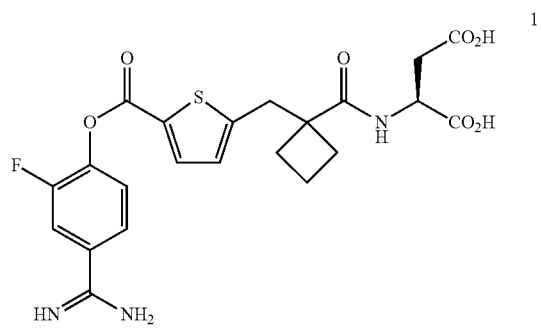

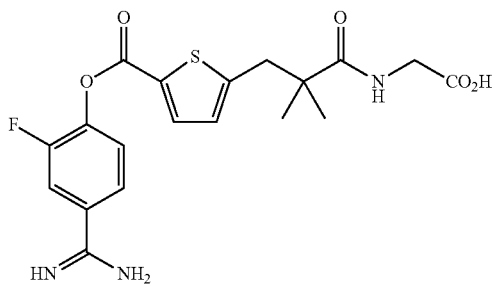
3
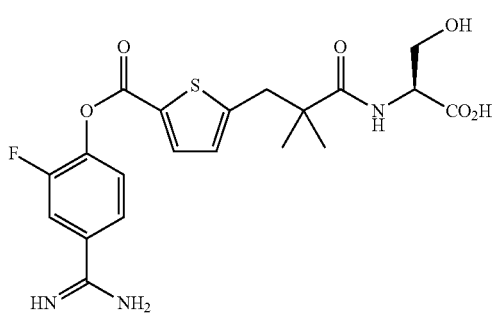
4
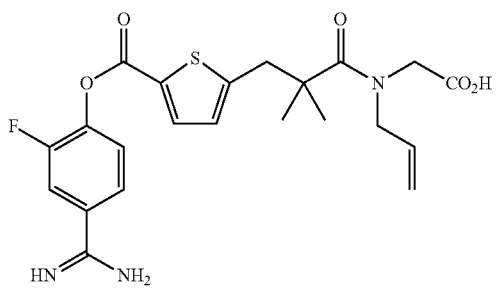
5
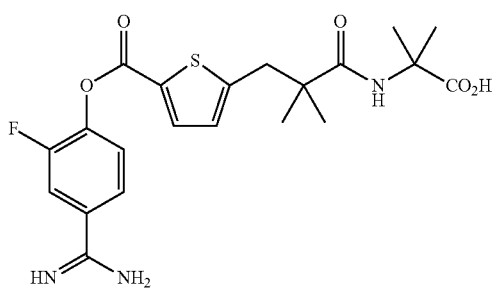
6
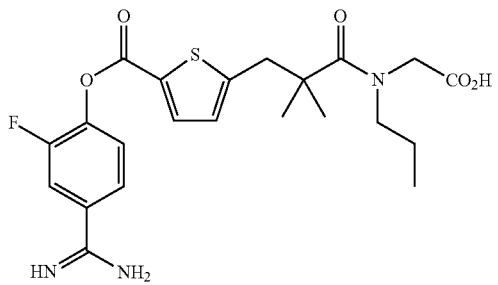
10
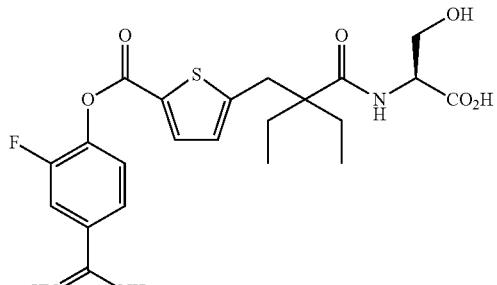
11
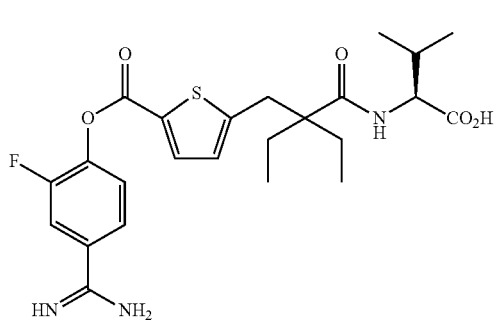
13
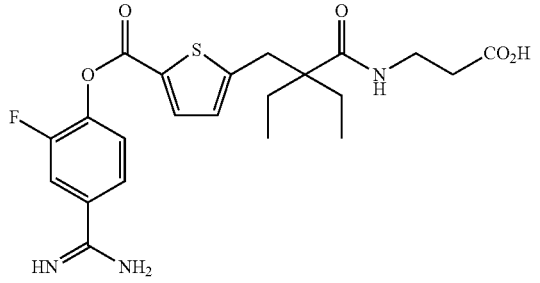
14
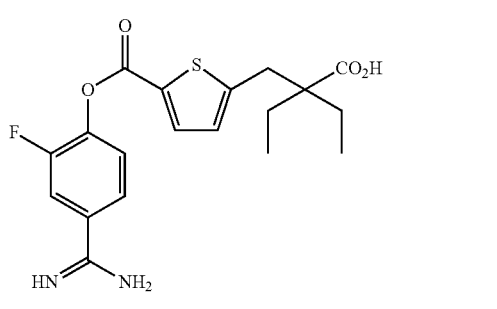
18
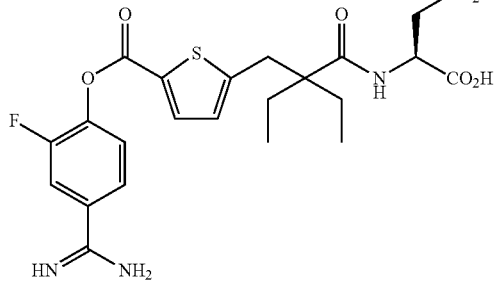
19

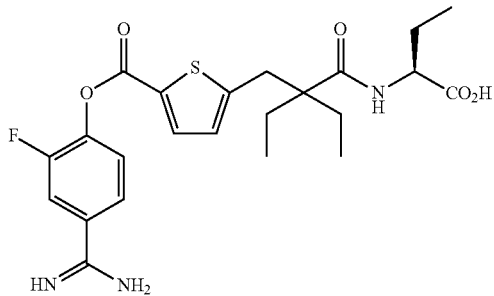
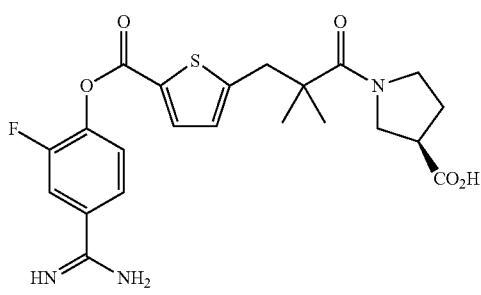
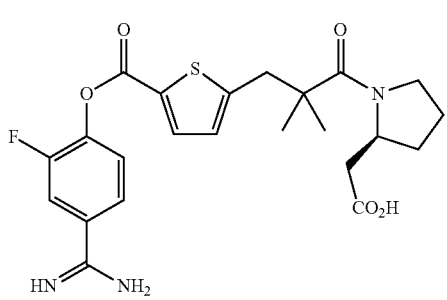
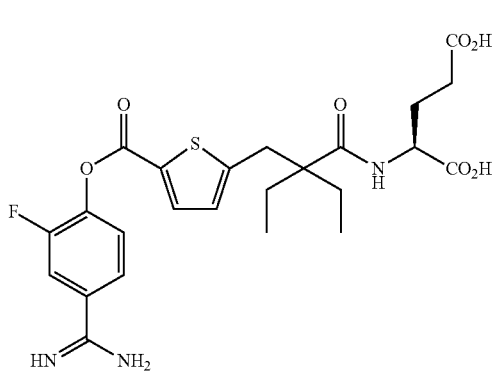
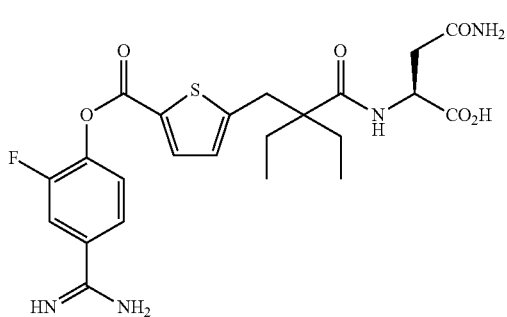
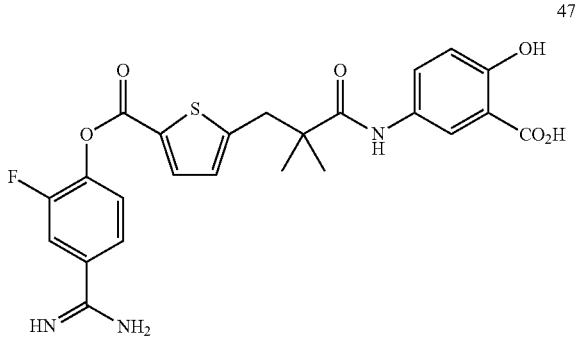
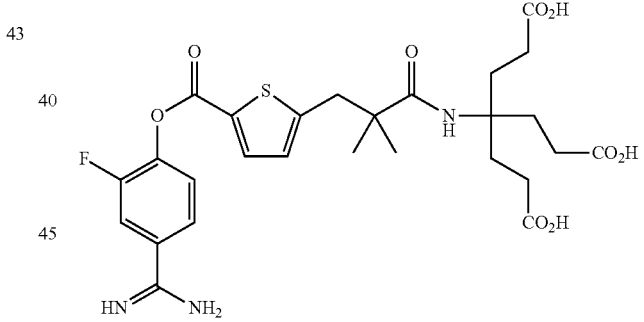
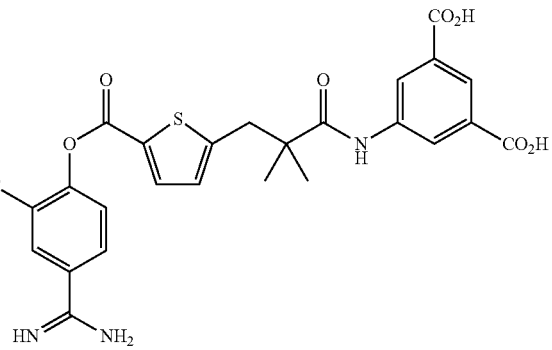

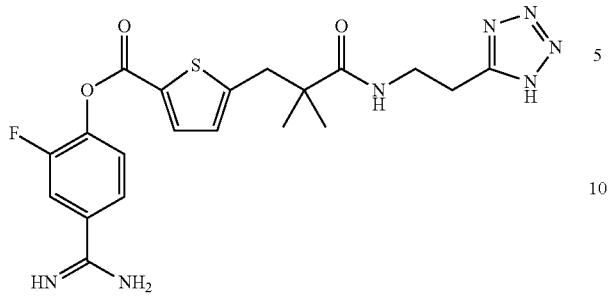

64

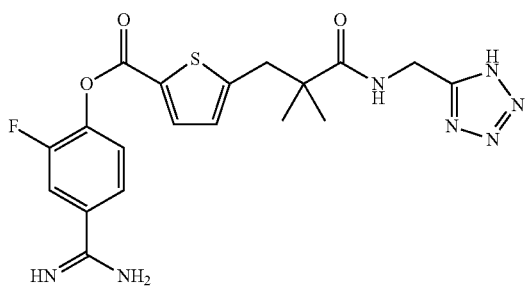

65

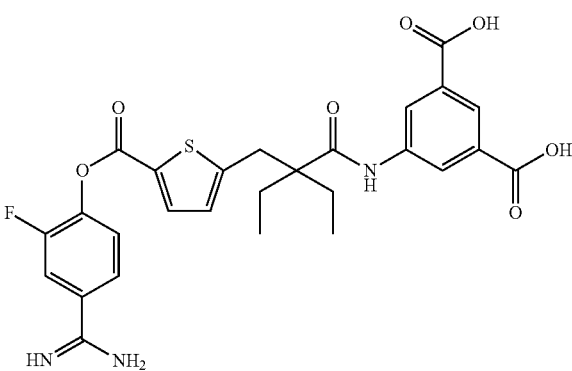

66

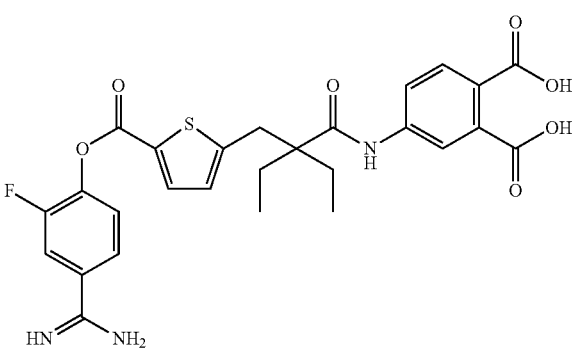

68

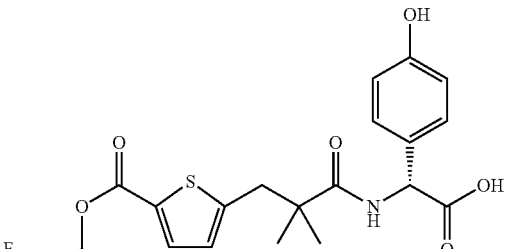

69

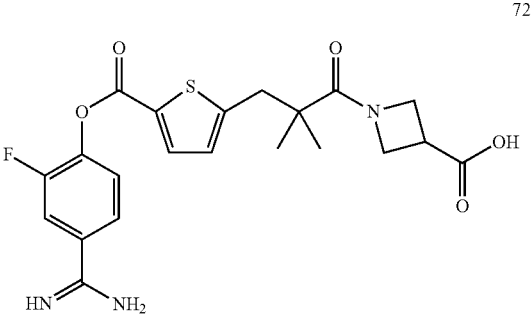

72

As preferable embodiments of the compound represented by the formula (I) or a pharmaceutically acceptable salt thereof, the following can also be mentioned.

Compound A.
A compound represented by the formula (I) wherein,
$R^1$ and $R^2$ are both methyl groups,
X is —$NR^4R^5$, wherein
$R^4$ is a hydrogen atom, a methyl, ethyl, propyl, or propenyl group,
$R^5$ is a $C_{3-4}$ alkyl group having 1 or 2 substituent(s) selected from the group of a carboxyl and hydroxyl group, and
$R^7$ is a fluorine atom,
or a pharmaceutically acceptable salt thereof.

Compound B.
A compound represented by the formula (I) wherein,
$R^1$ and $R^2$ are both ethyl groups,
X is —$NR^4R^5$, wherein,
$R^4$ is a hydrogen atom, a methyl, ethyl, propyl, or propenyl group,
$R^5$ is a $C_{1-6}$ alkyl group having 1 or 2 substituent(s) selected from the group of a carboxyl, hydroxyl, amino, and carbamoyl group, and
$R^7$ is a fluorine atom,
or a pharmaceutically acceptable salt thereof.

Compound C.
A compound represented by the formula (I) wherein,
$R^1$ and $R^2$ are both a methyl or ethyl group,
X is a group represented by formula (II) wherein,
$R^6$ is a hydrogen atom or a methyl group,
$R^7$ is a fluorine atom,
p=0,
q=1,
A is a phenyl, 3-pyridyl, or 4-pyridyl group,
Ya is a hydrogen, carboxyl, hydroxyl, methoxy, carboxy methyl, oxo group, or a halogen atom,
Yb is a hydrogen atom or a halogen atom,
or a pharmaceutically acceptable salt thereof.

As the serine protease inhibitory activity, an activity of simultaneously inhibiting trypsin and enteropeptidase is preferable.

When the compound of the present invention can form a salt, a pharmaceutically acceptable salt is preferable. Examples of such pharmaceutically acceptable salts for a compound having an acidic group such as a carboxyl group and the like include an ammonium salt, salts with alkali metals such as sodium, potassium, and the like, salts with alkaline earth metals such as calcium, magnesium, and the like, an aluminum salt, a zinc salt, salts with an organic amines such as triethylamine, ethanolamine, morpholine, pyrrolidine, piperidine, piperazine, dicyclohexylamine, and the like, and salts with a basic amino acid such as arginine, lysine, and the like. Examples of such pharmaceutically acceptable salts for a compound having a basic group include salts with an inorganic acid such as hydrochloric acid, sulfuric acid, phosphoric acid, nitric acid, hydrobromic acid, and the like, salts with an organic carboxylic acid such as acetic acid, citric acid, benzoic acid, maleic acid, fumaric acid, tartaric acid, succinic acid, tannic acid, butyric acid, pamoic acid, enanthic acid, decanoic acid, salicylic acid, lactic acid, oxalic acid, mandelic acid, malic acid, and the like, and salts with an organic sulfonic acid such as methanesulfonic acid, benzenesulfonic acid, p-toluenesulfonic acid, and the like.

The compound of the present invention also encompasses all optical isomers, stereoisomers, tautomers, rotamers, and mixtures thereof at optional ratios. These can be obtained each as a single product according to a synthesis method and separation method known per se. For example, an optical isomer can be obtained by using an optically active synthesis intermediate or by optically resolving a racemate of a synthesis intermediate or final product by a conventional method.

The compound of the present invention also includes solvates of the compound such as hydrates, alcohol adducts, and the like.

The compound of the present invention may be converted to a prodrug. The prodrug of the present invention means a compound that is converted in the body to produce the compound of the present invention. For example, when an active form contains a carboxyl group or a phosphoric acid group, an ester thereof, amide thereof, and the like can be mentioned. When an active form contains a carboxyl group, a group to be converted to a carboxyl group by oxidative metabolism, such as a hydroxymethyl group and the like can be mentioned. In addition, when the active form contains an amino group, examples thereof include an amide thereof, a carbamate thereof, and the like. When the active form contains a hydroxyl group, examples thereof include esters thereof, carbonates thereof, carbamates thereof, and the like. When the compound of the present invention is converted to a prodrug, it may be bonded to an amino acid or saccharide.

The present invention also encompasses a metabolite of the compound of the present invention. The metabolite of the compound of present invention means a compound resulting from the conversion of the compound of the present invention by a metabolic enzyme and the like in the body. For example, a compound wherein a hydroxyl group is introduced on the benzene ring of the compound of the present invention due to the metabolism, a compound wherein glucuronic acid, glucose, or an amino acid is bonded to the carboxylic acid moiety of the compound of the present invention or a hydroxyl group is added by the metabolism, and the like can be mentioned.

The compound of the present invention and a pharmaceutically acceptable salt thereof have a superior blood glucose elevation suppressing action for mammals such as humans, bovines, horses, dogs, mice, rats, cats, and the like, and can be used as a medicament, which is administered as it is or as a pharmaceutical composition containing the same mixed with a pharmaceutically acceptable carrier according to a method known per se. While oral administration is generally preferable, parenteral administration can also be employed (e.g., routes such as intravenous, subcutaneous, intramuscular, suppository, enema, ointment, patch, sublingual, eye drop, inhalation administrations, and the like). While the dose used for the above-mentioned objects is determined according to the desired treatment effect, administration method, duration of treatment, age, body weight, and the like, a daily dose of 1 µg to 10 g for oral administration and 0.01 µg to 1 g, preferably 0.1 µg to 1 g, for parenteral administration is used, which is generally administered to an adult by an oral or parenteral route in one to several portions per day. In addition, the content of the compound of the present invention in the above-mentioned pharmaceutical composition is about 0.01 wt % to 100 wt % of the whole composition.

Examples of the pharmaceutically acceptable carrier for the pharmaceutical composition of the present invention include various organic or inorganic carrier substances conventionally used as preparation materials. For example, an excipient, lubricant, binder, disintegrant, water-soluble polymer, and basic inorganic salt in a solid preparation; a solvent, solubilizing agents, suspending agent, isotonicity agent, buffering agent, and soothing agent in a liquid preparation, and the like can be mentioned. Where necessary, general additives such as a preservative, antioxidant, colorant, sweetening agent, souring agent, effervescing agent, flavor, and the like can also be used.

The dosage form of such a pharmaceutical composition may be a tablet, powder, pill, granule, capsule, suppository, solution, sugar-coated agent, depot, syrup, suspension, emulsion, troche, sublingual agent, adhesive preparation, oral disintegrant (tablet), inhalant, enema, ointment, patch, tape, or eye drop, and these can be produced using conventional formulation auxiliaries and according to a conventional method.

The pharmaceutical composition of the present invention can be produced according to a method conventionally used in the technical field of pharmaceutical formulation, for example, the method described in the Japanese Pharmacopoeia, which is incorporated herein by reference in its entirety, and the like. Specific production methods of the preparation are explained in detail in the following.

For example, when the compound of the present invention is prepared as an oral preparation, a excipient and, where necessary, a binder, disintegrant, lubricant, colorant, flavoring agent, and the like are further added, and the mixture is processed to give, for example, a tablet, powder, pill, granule, capsule, suppository, solution, sugar-coated agent, depot, syrup, and the like according to a conventional method. Examples of the excipient include lactose, cornstarch, sucrose, glucose, sorbitol, crystalline cellulose, and the like. Examples of the binder include polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone, and the like. Examples of the disintegrant include starch, agar, gelatin powder, crystalline cellulose, calcium carbonate, sodium hydrogen carbonate, calcium citrate, dextran, pectin, and the like. Examples of the lubricant include magnesium stearate, talc, polyethylene glycol, silica, hydrogenated vegetable oil, and the like. As the colorant, one acceptable to add to a pharmaceutical product is used, and as the flavoring agent, cocoa powder, menthol, aromatic acid, peppermint oil, borneol, powdered cinnamon bark, and the like are used. Where necessary, these tablets and granules are applied with a coating as appropriate such as a sugar coating, gelatin coating, and the like.

When an injection is to be prepared, a pH adjuster, buffering agent, stabilizer, preservative, and the like are added where necessary, and the mixture is processed to give subcutaneous, intramuscular, or intravenous injection according to a conventional method.

While the compound of the present invention can be used as an agent for the treatment or prophylaxis of diabetes as mentioned above, it can also be used in combination with other therapeutic agents for diabetes and agents for the treatment or prophylaxis of diabetic complications, which are used generally. Examples of the therapeutic agents for diabetes and agents for the treatment or prophylaxis of diabetic complications, which are used generally, include combinations and mixtures of one or more kinds of an insulin preparation, insulin derivative, insulin-like agent, insulin secretagogue, insulin sensitizer, biguanide, gluconeogenesis inhibitor, glucose absorption inhibitor, renal glucose reabsorption inhibitor, β3 adrenoceptor agonist, glucagon-like peptide-1(7-37), glucagon-like peptide-1(7-37) analogs, glucagon-like peptide-1 receptor agonist, dipeptidyl peptidase IV inhibitor, aldose reductase inhibitor, inhibitor of advanced glycation end product formation, glycogen synthase kinase-3 inhibitor, glycogen phosphorylase inhibitor, antihyperlipidemic drug, anorectic agent, lipase inhibitor, antihypertensive agent, peripheral circulation improving agent, antioxidant, a therapeutic drug for diabetic neuropathy, and the like.

A medicament to be used in combination with the compound of the present invention may be mixed to give a single agent or each may be formulated into separate preparations, or prepared into a combination preparation (set, kit, or pack) obtained by packaging each of the separately formulated preparations in one container.

The administration form of combined use is not particularly limited and, for example, (1) administration as a single preparation, (2) simultaneous administration of separate preparations by the same administration route, (3) administration of separate preparations in a staggered manner by the same administration route, (4) simultaneous administration of separate preparations by different administration routes, (5) administration of separate preparations in a staggered manner by different administration routes, and the like can be mentioned.

In addition, the compound of the present invention is also useful even when contained in food.

A food composition containing the compound of the present invention is useful as a food for the treatment or prophylaxis of diabetes.

The "food" of the present invention means general foods, which include foods for specified health uses and foods with nutrient function claims defined by Food with Health Claims of Consumer Affairs Agency, Government of Japan, in addition to general foods including so-called health food, and further encompasses dietary supplements.

The form of the food composition of the present invention is not particularly limited, and the composition may take any form as long as it can be orally ingested.

Examples thereof include a powder, granule, tablet, hard capsules, soft capsule, liquid (drinks, jelly drinks, and the like), candy, chocolate, and the like, all of which can be produced according to a method known per se in the technical field.

The content of the compound of the present invention in the food composition is appropriately determined to afford an appropriate dose within the indicated range.

The food composition of the present invention can use other food additives as necessary. Examples of such food additives include those generally used as components of health foods such as a fruit juice, dextrin, cyclic oligosaccharide, saccharides (monosaccharides such as fructose, glucose, and the like, and polysaccharides), acidulant, flavor, powdered green tea, and the like, which are used for controlling and improving taste, emulsifier, collagen, whole milk powder, polysaccharide thickener, agar, and the like, which are used for improving texture, and further, vitamins, eggshell calcium, calcium pantothenate, the other minerals, royal jelly, propolis, honey, dietary fiber, Agaricus, chitin, chitosan, flavonoids, carotenoids, lutein, traditional Japanese herbal medicine, chondroitin, various amino acids, and the like.

A production method of a representative compound of the heteroarylcarboxylic acid ester derivatives represented by the formula (I), which is the compound of the present invention, is shown below.

Heteroarylcarboxylic acid ester derivative (H) represented by the formula (I)

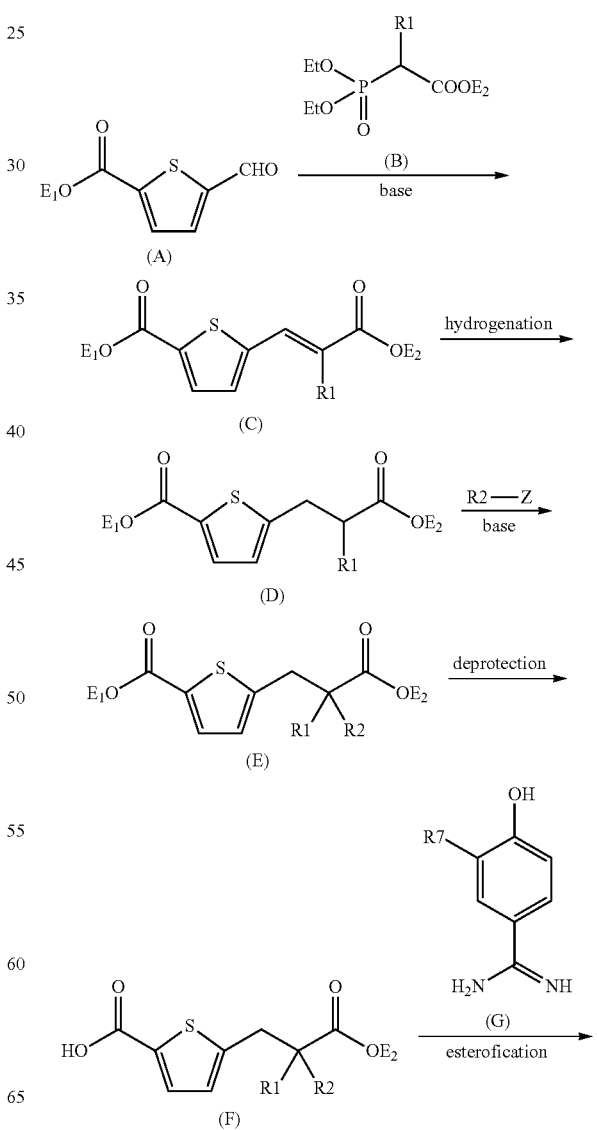

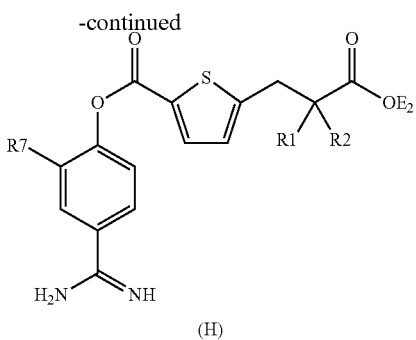

(H)

wherein X is —OR³, and R³ is a lower alkyl group can be produced as follows.

Alkenylene derivative (C) can be synthesized by reacting aldehyde (A) (wherein $E_1$ is a protecting group such as a methyl group, an ethyl group, a tert-butyl group, a benzyl group, and the like) with Wittig reagent (B) in, for example, a solvent that does not adversely influence the reaction, such as tetrahydrofuran, N,N-dimethylformamide and the like, in the presence of, for example, a base such as sodium hydride and the like. Alkenylene derivative (C) can be converted to alkylene derivative (D) by hydrogenation with a catalyst in the presence of a catalyst, for example, 10% palladium/carbon, palladium hydroxide/carbon, and the like under a hydrogen atmosphere in a solvent that does not adversely influence the reaction, such as ethyl acetate, methanol, tetrahydrofuran, dichloromethane, chloroform and the like.

After converting alkylene derivative (D) into the enolate with a base such as litium bis(trimethylsilyl)azanide, lithium diisopropylamide, and the like in a solvent, for example tetrahydrofuran, N,N-dimethylformamide, and like, at low temperature, it can be reacted with R2-Z (wherein Z is a leaving group such as a iodo group, bromo group, and the like) to can lead to dialkyl derivative (E).

Carboxylic acid derivative (F) can be obtained by deprotecting dialkyl derivative (E) by, for example, hydrolysis with a base such as sodium hydroxide and the like, hydrolysis with an acid such as hydrochloric acid, trifluoroacetic acid and the like or treating with, for example, 10% palladium/carbon and the like under a hydrogen atmosphere.

Heteroarylcarboxylic acid ester derivative (H) can be produced by esterifying carboxylic acid derivative (F) with amidinophenol derivative (G).

The esterification reaction can be performed by a known method which is, for example, (1) a method using an acid halide, (2) a method using a condensation agent and the like.

(1) The method using an acid halide is performed, for example, by reacting an acid chloride obtained by reaction with thionyl chloride, oxalyl chloride, and the like in a solvent that does not adversely influence the reaction, such as dichloromethane, N-methylpyrrolidone, and the like, or without solvent in the presence or absence of, for example, a catalyst such as N,N-dimethylformamide and the like, with the alcohol in a solvent that does not adversely influence the reaction such as dichloromethane, tetrahydrofuran, and the like in the presence of a base such as pyridine and triethylamine.

(2) The method using a condensation agent is performed, for example, by reacting the carboxylic acid with the alcohol in, for example, a solvent that does not adversely influence the reaction such as tetrahydrofuran, N,N-dimethylformamide, dichloromethane, 1,2-dichloloethane, pyridine, and the like in, for example, the presence or absence of a base such as pyridine, triethylamine, and the like, by using a condensation agent such as 1-ethyl-3-(3'-dimethylaminopropyl)carbodiimide (WSC), 1,3-dicyclohexylcarbodiimide, and the like.

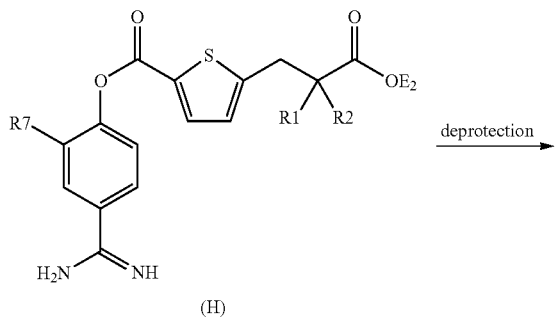

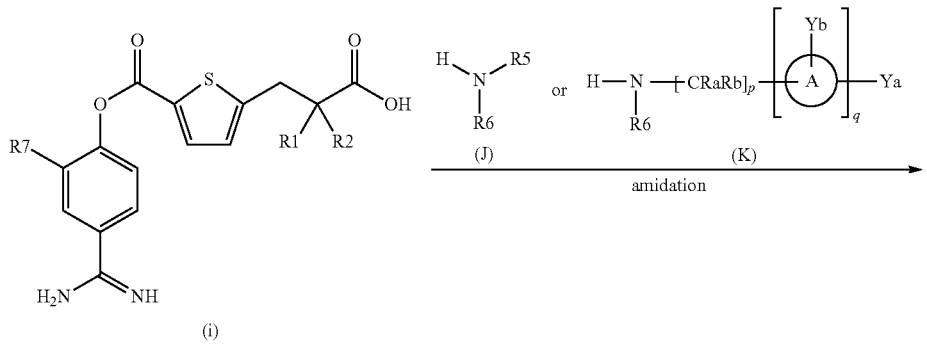

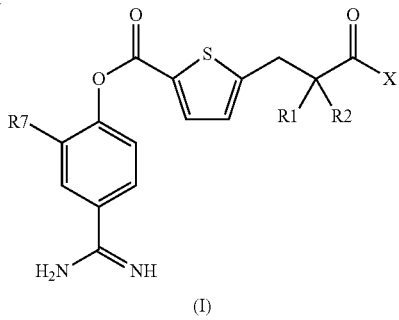

Heteroarylcarboxylic acid ester derivative (H) can be converted to carboxylic acid derivative (i) in the same manner as in the afore-mentioned deprotection reaction. Heteroarylcarboxylic acid ester derivative (I) can be produced by amidating carboxylic acid derivative (i) with amine (J) or (K). The amidation reaction of the carboxylic acid derivative is performed using the corresponding amine instead of an alcohol and in the same manner as in the aforementioned esterification reaction.

Dialkyl derivative (E) can be also synthesized by reacting alpha-dialkyl carboxylic acid (L) with alkyl halide (M) (wherein Z is a leaving group such as a chloro group, bromo group, and the like).

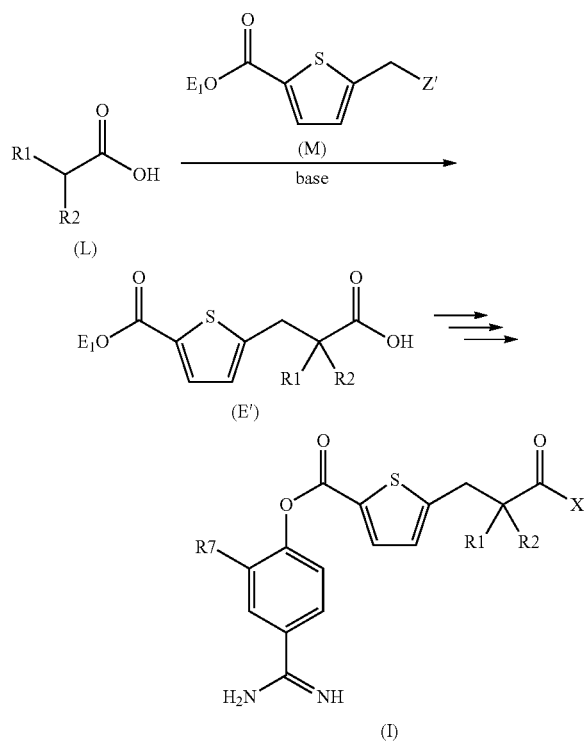

After converting alpha-dialkyl carboxyric acid (L) into the enolate with a base such as litium bis(trimethylsilyl)azanide, lithium diisopropylamide, and the like in a solvent, for example tetrahydrofuran, N,N-dimethylformamide, and like, at low temperature, it can be reacted with alkyl halide (M) and to lead to dialkyl derivative (E').

Dialkyl derivative (E') can be converted to heteroarylcarboxylic acid ester derivative (I) in the same manner as in the afore-mentioned protection, deprotection, esterification, and amidation.

Amines (J) or (K) can be obtained according to the following Examples or any know methods.

Other features of the invention will become apparent in the course of the following descriptions of exemplary embodiments which are given for illustration of the invention and are not intended to be limiting thereof.

EXAMPLES

Example 1

Synthesis of N-[1{5-(4-amidino-2-fluorophenoxycarbonyl)thiophen-2-ylmethyl}-cyclobutylcarbonyl]-1-aspartic acid trifluoroacetic acid salt (compound 1)

Step 1. Synthesis of 3-fluoro-4-hydroxylbenzamidine hydrochloride

To 3-fluoro-4-hydroxybenzonitrile (7.56 g, 55.2 mmol) were added ethanol (20 mL) and 4N-Hydrogen chloride in 1,4-Dioxane (100 mL), and the mixture was stirred at room temperature. After 5 days, the mixture was concentrated and dried with a vacuum pump. Then, the mixture was dissolved in ethanol (100 mL), ammonium carbonate (11.0 g, 115 mmol) was added, and the mixture was stirred at room temperature. After 12 hours, the solvent was evaporated, and the residue was dissolved in water (100 mL). The mixture was lyophilized to give the title compound (11.2 g, quantitative).

1H-NMR(300 MHz, DMSO-d6) δ 11.28(1H, br s), 9.19 (2H, br s), 9.02(2H, br s), 7.75(1H, dd, J=2.4, 12.0 Hz), 7.59(1H, m), 7.18(1H, dd, J=8.4, 8.7 Hz).

MS(ESI) m/z 155(M+H)+

Step 2. Synthesis of 5-formyl-2-thiophencarboxylic acid tert-butyl ester

To a solution of 5-formyl-2-thiophencarboxylic acid (25 g, 0.16 mol) in tert-butyl alcohol (200 mL) and dichloromethane (100 mL) was added di-tert-butyl dicarbonate (41g, 0.19mol), N,N-dimethylaminopyridine (2.0 g, 0.016 mol), and pyridine (5 mL), and the mixture was stirred at room temperature for 24 hours. The reaction mixture was concentrated under reduced pressure. The residue was added to ethyl acetate and 0.5N-hydrochloric acid solution, the organic layer was extracted, and the aqueous layer was extracted two times with ethyl acetate. The organic layers were collected, washed with 0.5 N sodium hydroxide solution and brine, and dried over anhydrous magnesium sulfate. The solvent of the filtrate after filtration was evaporated under reduced pressure to give the title compound (32.1 g, 0.15 mol, 94%).

1H-NMR(400 MHz, CDCl$_3$) δ 9.95(1H, s), 7.75(1H, d, J=4.0 Hz), 7.70(1H, d, J=4.0 Hz), 1.59(9H, s).

Step 3. Synthesis of 5-chloromethyl-2-thiophencarboxylic acid tert-butyl ester To a solution of 5-formyl-2-thiophencarboxylic acid tert-butyl ester (5g, 23.6mmol) in tetrahydrofuran (50 ml) and methanol (5 ml), was added sodium borohydride (0.50 g, 13.0 mmol) at 0° C., and the mixture was stirred for 2 hours at room temperature. The reaction mixture was partitioned between ethyl acetate and 0.5N-hydrochloric acid solution. The aqueous layer was extracted with ethyl acetate, and the combined organic layers were washed with brine and dried over anhydrous magnesium sulfate. The solvent was removed under reduced pressure, and the obtained residue was dissolved in dichloromethane (100 mL), methanesulfonyl chloride (1.9 ml, 24mmol) and diisopropylethylamine (5.7 ml, 33 mmol) were added at 0° C., and the mixture was stirred at room temperature overnight. The solvent was evaporated under reduced pressure, 0.5N-hydrochloric acid solution was added to the residue, and the mixture was extracted with ethyl acetate. The extract was washed with brine, dried over anhydrous magnesium sulfate, and concentrated under reduced pressure. The obtained residue was purified by silica gel column chromatography to give the title compound (5.3 g, 23 mmol).

$^1$H NMR(400 MHz, CDCl$_3$) δ 7.56(1H, d, J=3.8 Hz), 7.03 (1H, d, J=3.8 Hz), 4.75(2H, s), 1.57(9H, s).

Step 4. Synthesis of 1-{5-(tert-butoxycarbonyl) thiophen-2-ylmethyl}cyclobutylcarboxylic acid To a solution of diisopropylamine (905 uL, 6.44 mmol) in tetrahydrofuran (0.5 mL), was added n-butyllithium (3.9 mL, 1.65 M in hexane) at −78 ° C. After stirring at 0 ° C. for 25 minutes, a mixture was cooled to −78 ° C. Cyclobutylcarboxylic acid (372 uL, 3.58 mmol) was added to the reaction mixture, and stirred at room temperature for 15 minutes. After cooled to −78 ° C., 5-chloromethyl-2-thiophencarboxylic acid tert-butyl ester obtained in step 3 (333 mg, 1.43 mmol) in tetrahydrofuran (0.5 mL) was added to the reaction mixture. After stirred at room temperature for 2 hours, the reaction mixture was partitioned between ethyl acetate and 1N-hydrochloric acid solution. The aqueous layer was extracted with ethyl acetate, and the combined organic layers were washed with brine and dried over anhydrous magnesium sulfate. The solvent was removed under reduced pressure, and the obtained residue was purified by high performance liquid chromatography (water-acetonitrile, each containing 0.1% trifluoroacetic acid) to give the title compound (60 mg, 0.201 mmol, 14%).

1H-NMR (400 MHz, CDCl$_3$) δ 7.53 (1H, d, J=3.7 Hz), 6.79 (1H, d, J=3.7 Hz), 3.30 (2H, s), 2.63-2.47 (2H, m), 2.18-2.05 (2H, m), 2.05-1.88 (2H, m), 1.53 (9H, s).

MS(ESI) m/z 297(M+H)+

Step 5. Synthesis of N-{1-(5-carboxylthiophen-2-ylmethy)cyclobutylcarbonyl}-1-aspartic acid dimethyl ester 3-{5-(tert-butylcarboxyl)thiophen-2-yl}-2-cyclobutylpropanoic acid (50 mg, 0.169 mmol) was solved in sulfonyl chloride (0.5 mL), and stirred at 60° C. for 30 minutes. After the solvent was removed under reduced pressure, to a solution of the product obtained in step 4 in dichloromethane (0.3 mL) was added L-aspartic acid dimethyl ester (50 mg, 0.253 mmol), and pyridine (0.3 mL). After the reaction mixture was stirred at room temperature for 1 hour, WSC hydrochloride (60 mg, 0.338 mmol) was added and stirred at room temperature for 3 hours. After the solvent was removed under reduced pressure, the residue was resolved in trifluoroacetic acid (0.5 mL). After the solution was stirred at room temperature for 1 hour, the reaction mixture was concentrated under reduced pressure. The obtained residue was purified by high performance liquid chromatography (water-acetonitrile, each containing 0.1% trifluoroacetic acid) to give the title compound (32 mg, 0.093 mmol, 55%).

1H-NMR (400 MHz, DMSO-d6) δ 8.18 (1H, d, J=7.9 Hz), 7.52 (1H, d, J=3.7 Hz), 6.85 (1H, d, J=3.7 Hz), 4.72-4.53 (1H, m), 3.61 (3H, s), 3.60 (3H, s), 3.28 (2H, s), 2.84 (1H, dd, J=16.2, 6.2 Hz), 2.66 (1H, dd, J=16.2, 7.9 Hz), 2.39-2.20 (2H, m), 2.01-1.78 (3H, m), 1.77-1.63 (1H, m).

MS(ESI) m/z 384 (M+H)+

Step 6. Synthesis of N-[1-{5-(4-amidino-2-fluorophenoxycarbonyl) thiophen-2-ylmethyl}cyclobutylcarbonyl]-1-aspartic acid trifluoroacetic acid salt (compound 1)

To a solution of N-{3-(5-carboxylthiophen-2-yl)-2-cyclobutylpropanoyl}-1-aspartic acid dimethyl ester (30 mg, 0.087 mmol) in pyridine (1.0 mL), was added 3-fluoro-4-hydroxylbenzamidine hydrochloride (25 mg, 0.131 mmol) and WSC hydrochloride (34 mg, 0.175 mmol), and the mixture was stirred at room temperature overnight. After the solvent was removed under reduced pressure, the obtained residue was dissolved in 4N-hydrogene chloride in 1,4-dioxane (0.6 mL) and water (0.2 mL). After the reaction mixture was stirred at 60° C. for 9 hours, the reaction mixture was concentrated under reduced pressure. The obtained residue was purified by high performance liquid chromatography (water-acetonitrile, each containing 0.1% trifluoroacetic acid) to give the title compound (18 mg, 0.030 mmol, 34%).

1H-NMR (400 MHz, DMSO-d6) δ 9.42 (2H, br s), 9.09 (2H, br s), 8.07 (1H, d, J=8.0 Hz), 7.99-7.83 (2H, m), 7.92-7.82 (1H, m), 7.79-7.69 (2H, m), 7.06 (1H, d, J=3.9 Hz), 4.56 (1H, dd, J=13.9, 7.6 Hz), 3.48 (2H, s), 2.74 (1H, dd, J=16.4, 6.0 Hz), 2.64-2.49 (1H, m), 2.40-2.25 (2H, m), 2.05-1.83(3H, m), 1.80-1.69(1H, m).

MS(ESI) m/z 492 (M+H)+

Example 2

Synthesis of N-{1-[5-(4-amidino-2-fluorophenoxycarbonyl) thiophen-2-ylmethyl]-2-cyclopentylcarbonyl}-1-aspartic acid trifluoroacetic acid salt (compound 2)

The compound 2 was synthesized by an operation in the same manner as in the above-mentioned Example 1.

1H-NMR (400 MHz, DMSO-d6) δ 9.36 (2H, br s), 9.08 (2H, br s), 7.97 (1H, d, J=7.9 Hz), 7.89-7.80 (2H, m), 7.72-7.63 (2H, m), 7.00 (1H, d, J=3.9 Hz), 4.49 (2H, dt, J=12.9, 6.4 Hz), 3.17 (2H, s), 2.69 (1H, dd, J=16.4, 6.0 Hz), 2.57-2.45 (2H, m), 2.02-1.81 (2H, m), 1.63-1.37 (6H, m).

MS(ESI) m/z 506 (M+H)+

Example 3

Synthesis of N-{3-[5-(4-amidino-2-fluoro-phenoxycarbonyl)thiophen-2-yl]-2,2-dimethylpropionyl}-1-valine hydrochloride (compound 9)

Step 1. Synthesis of 2-(diethylphosphono)propanoic acid methyl ester

Methyl 2-bromopropionate (100 g, 0.60 mol) and triethylphosphite (109 g, 0.66 mol) were mixed, and the mixture was stirred at 110° C. for 2 days. The reaction mixture was dried under reduced pressure to give the title compound.

Step 2. Synthesis of 5-[(1E)-2-(methoxycarbonyl)-prop-1-en-1-yl]thiophene-2-carboxylic acid tert-butyl ester 2-(Diethylphosphono)propanoic acid methyl ester (23.0 g, 0.103 mol) was dissolved in tetrahydrofuran (150 mL), 60% sodium hydride (2.4 g, 0.06 mol) was added at 0° C., and the mixture was stirred for 30 minutes. To the reaction mixture was added a solution of 5-formyl-2-thiophenecarboxylic acid tert-butyl ester obtained in Example 1, step 2(11.0 g, 0.052 mol) in tetrahydrofuran (10 mL), and the mixture was stirred at room temperature overnight. The solvent was evaporated, and the residue was partitioned between ethyl acetate and 1N-hydrochloric acid solution, and washed successively with water and brine. After drying over anhydrous magnesium sulfate, the residue was purified by silica gel column chromatography to give the title compound (13.1 g, 0.047 mol, 90%).
$^1$H-NMR(400 MHz, CDCl$_3$) δ 7.89(1H, s), 7.68(1H, d, J=4.0 Hz), 7.19(1H, d, J=4.0 Hz), 3.82(3H, s), 2.24(3H, s), 1.59(9H, s).

Step 3. Synthesis of 5-(2-methoxycarbonylpropyl)thiophene-2-carboxylic acid tert-butyl Ester 5 [(1E)-2-(methoxycarbonyl)-prop-1-en-1-yl]thiophene-2-carboxylic acid tert-butyl ester (13.77 g, 0.049 mol) was dissolved in ethyl acetate (60 mL), methanol (20 mL), and chloroform (10 mL), palladium hydroxide (2.8 g) was added, and the mixture was stirred at room temperature overnight under a hydrogen atmosphere. After completion of the reaction, palladium hydroxide was removed by celite filtration, and the solvent was evaporated under reduced pressure to give the title compound (13.14 g, 0.046 mol, 94%).
$^1$H-NMR(400 MHz, CDCl$_3$) δ 7.53(1H, d, J=4.0 Hz), 6.77 (1H, d, J=4.0 Hz), 3.67(3H, s), 3.18(1H, dd, J=14.4, 7.2 Hz), 2.91(1H, dd, J=14.4, 7.2 Hz), 2.77(1H, m), 1.56(9H, s), 1.21 (3H, d, J=7.2 Hz).

Step 4. Synthesis of 5-(2-methyl-2-methoxycarbonylpropyl)thiophene-2-carboxylic acid tert-butyl ester 5-(2-Methoxycarbonylpropyl)thiophene-2-carboxylic acid tert-butyl ester (13.14 g, 46.3 mmol) was dissolved in tetrahydrofuran (250 mL), 1.09 M lithium bis(trimethylsilyl) azanide/tetrahydrofuran solution (65 mL, 70.9 mmol) was added dropwise at −78° C., and the mixture was stirred for 2 hours. To the reaction mixture was added methyl iodide (11.7 g, 82.4 mmol) at −78° C., and the mixture was stirred at room temperature overnight. The reaction mixture was concentrated under reduced pressure. The residue was added to ethyl acetate and 0.5N-hydrochloric acid solution, the organic layer was extracted, and the aqueous layer was extracted two times with ethyl acetate. The organic layers were collected, washed with sodium thiosulfate solution and brine, and dried over anhydrous magnesium sulfate. The solvent of the filtrate after filtration was evaporated under reduced pressure. The obtained residue was purified by silica gel column chromatography to give the title compound (12.36 g, 41.4 mmol, 89%).
$^1$H-NMR(400 MHz, CDCl$_3$) δ 7.53(1H, d, J=3.6 Hz), 6.73 (1H, d, J=3.6 Hz), 3.71(3H, s), 3.05(2H, s), 1.56(9H, s), 1.23(6H, s).

Step 5. Synthesis of 3-[5-(4-amidino-2-fluorophenoxycarbonyl)thiophen-2-yl]-2,2-dimethylpropanoic acid trifluoroacetic acid salt To 5-(2-Methyl-2-methoxycarbonylpropyl)thiophene-2-carboxylic acid tert-butyl ester (5.0 g, 16.8 mmol) was added trifluoroacetic acid (20 mL), and the mixture was stirred at room temperature for 30 minutes. The solvent was evaporated, and the residue was dissolved in pyridine (30 mL), 3-fluoro-4-hydroxybenzamidine hydrochloride (3.2 g, 16.8 mmol) and WSC hydrochloride (3.8 g, 19.8 mmol) were added, and the mixture was stirred at 50° C. for 5 hours. The reaction mixture was concentrated under reduced pressure, 4N-hydrochloric acid solution (10 mL) and 4N-Hydrogen chloride in 1,4-Dioxane (10 mL) were added to the obtained residue, and the mixture was stirred at 80° C. for 2 hours. The reaction mixture was concentrated under reduced pressure, and the obtained residue was purified by high performance liquid chromatography (water-acetonitrile, each containing 0.1% trifluoroacetic acid) to give the title compound (2.8 g, 5.86 mmol, 35%).
$^1$H-NMR(400 MHz, DMSO-d6) δ 9.41(2H, br s), 9.10(2H, br s), 7.96(1H, d, J=4.0 Hz), 7.93(1H, d, J=8.1 Hz), 7.80-7.70 (2H, m), 7.09(1H, d, J=4.0 Hz), 3.14(2H, s), 1.16(6H, s).
MS(ESI) m/z 365(M+H)+

Step 6. Synthesis of N-{3-[5-(4-amidino-2-fluoro-phenoxycarbonyl)thiophen-2-yl]-2,2-dimethylpropionyl}-1-valine hydrochloride (compound 9)

3-[5-(4-Amidino-2-fluorophenoxycarbonyl)thiophen-2-yl]-2,2-dimethylpropanoic acid trifluoroacetic acid salt obtained in step 5(53 mg, 0.10 mmol) was dissolved in thionyl chloride (3 mL), and the mixture was stirred at room temperature for 3 hours. Thionyl chloride was evaporated under reduced pressure to give the acid chloride. The obtained acid chloride was dissolved in dichloromethane (3 mL), L-valine tert-butyl ester hydrochloride (25 mg, 0.12 mmol) and pyridine (0.1 mL) were added thereto, and the mixture was stirred at room temperature overnight. After evaporation of the solvent, trifluoroacetic acid (2 mL) was added, and the mixture was stirred at room temperature 1 hour. The mixture was concentrated under reduced pressure. The obtained residue was purified by high performance liquid chromatography (water-acetonitrile, each containing 0.1% trifluoroacetic acid) to give the trifluoroacetic acid salt of the title compound.
To the obtained trifluoroacetic acid salt was added 0.05N-hydrochloric acid solution (10 mL), and the mixture was lyophilized to give the title compound (40 mg, 0.80 mmol, 80%).
$^1$H-NMR(400 MHz, DMSO-d6) δ 9.41(2H, br s), 9.10(2H, br s), 8.00-7.89(2H, m), 7.80-7.70(2H, m), 7.57(1H, d, J=7.2 Hz), 7.08(1H, s), 4.13(1H, m), 3.21(1H, d, J=16.0 Hz), 3.15 (1H, d, J=16.0 Hz), 2.15-2.05(1H, m), 1.76-1.50(4H, m), 0.90(3H, d, J=6.8 Hz), 0.86-0.75(6H, m).
MS(ESI) m/z 464 (M+H)+

Example 4

Synthesis of N-{3-[5-(4-amidino-2-fluoro-phenoxycarbonyl)thiophen-2-yl]-2,2-dimethylpropionyl}-N-propylglycine hydrochloride (compound 10)

Step 1. Synthesis of N-allylglycine benzyl ester hydrochloride

To a solution of allylamine hydrochloride (5.0 g, 53.4 mmol) in tetrahydrofuran (100 mL) was added diisopropylethylamine (10 mL) and bromoacetic acid benzyl ester (3.06 g, 13.3 mmol) at 0° C. and the mixture was stirred at room temperature overnight. The reaction mixture was concentrated under reduced pressure. The residue was added ethyl acetate and 1 N-hydrochloric acid solution, the organic layer was extracted, and the aqueous layer was extracted two times with ethyl acetate. The organic layers were collected, washed with sodium thiosulfate solution and brine, and dried over anhydrous magnesium sulfate and concentrated under reduced pressure. The obtained residue was purified by silica gel column chromatography, and to the obtained oil was added 4N-Hydrogen chloride in 1,4-Dioxane (3.5 mL). The mixture was concentrated under reduced pressure and lyophilized to give the title compound (2.12 g, 8.79 mmol, 66%).

$^1$H-NMR(400 MHz, CDCl$_3$) δ 7.40-7.35(5H, m), 6.12-6.02(1H, m), 5.49-5.43(2H, m), 5.22(2H, s), 3.82(2H, s), 3.78(2H, d, J=7.2 Hz).
MS(ESI) m/z 206(M+H)+

Step 2. Synthesis of N-{3-[5-(4-amidino-2-fluoro-phenoxycarbonyl)thiophen-2-yl]-2,2-dimethylpropionyl}-N-allylglycine benzyl ester trifluoroacetic acid salt 3-[5-(4-Amidino-2-fluorophenoxycarbonyl)thiophen-2-yl]-2,2-dimethylpropanoic acid trifluoroacetic acid salt (100 mg, 0.20 mmol) obtained in Example 3, step 5 was dissolved in thionyl chloride (3 mL), and the mixture was stirred at 60° C. for 20 minutes. Thionyl chloride was evaporated under reduced pressure to give the acid chloride. The obtained acid chloride was dissolved in dichloromethane (5 mL), N-allylglycine benzyl ester hydrochloride obtained in step 1(51 mg, 0.21 mmol) and pyridine (0.1 mL) were added thereto, and the mixture was stirred at room temperature overnight. The mixture was concentrated under reduced pressure. The obtained residue was purified by high performance liquid chromatography (water-acetonitrile, each containing 0.1% trifluoroacetic acid) to give the title compound. (37 mg, 0.056 mmol, 28%).

$^1$H-NMR(400 MHz, DMSO-d6) δ 9.40(2H, br s), 9.05(2H, br s), 7.90(2H, m), 7.72(2H, m), 7.38-7.28(5H, m), 7.11(1H, d, J=4.0 Hz), 5.86-5.73(1H, m), 5.25-5.15(2H, m), 5.12(2H, s), 4.28-4.18(2H, m), 4.01-4.91(2H, m), 3.19(2H, s), 1.23 (6H, s).
MS(ESI) m/z 552 (M+H)+

Step 3. Synthesis of N-{3-[5-(4-amidino-2-fluoro-phenoxycarbonyl)thiophen-2-yl]-2,2-dimethylpropionyl}-N-propylglycine hydrochloride (compound 10)

N-{3-[5-(4-Amidino-2-fluoro-phenoxycarbonyl)thiophen-2-yl]-2,2-dimethylpropionyl}-N-allylglycine benzyl ester trifluoroacetic acid salt (1.94 g, 2.91 mmol) was dissolved in ethanol (40 mL) and water (10 mL), palladium hydroxide (0.4 g) was added, and the mixture was stirred at room temperature for 6 hours under a hydrogen atmosphere. The reaction mixture was filtered through celite, and the filtrate was concentrated under reduced pressure. To the obtained residue was added 0.01N-hydrochloric acid solution (250 mL), and the mixture was lyophilized to give the title compound (1.19 g, 2.02 mmol, 70%).

$^1$H-NMR(400 MHz, DMSO-d6) δ 9.41(2H, br s), 9.05(2H, br s), 7.93(2H, m), 7.74(2H, m), 7.11(1H, d, J=3.6 Hz), 3.75-3.65(2H, m), 3.18(2H, s), 1.58-1.48(2H, m), 1.25(6H, br s), 0.84(3H, m).
MS(ESI) m/z 464 (M+H)+

Example 5

Synthesis of 3-[5-(4-amidino-2-fluorophenoxycarbonyl)thiophen-2-yl]-2,2-diethylpropanoic acid trifluoroacetic acid salt (compound 18)

Step 1. Synthesis of 2-(diethylphosphono)butyric acid methyl ester

Methyl 2-bromobutanoate (92 g, 0.508 mol) and triethylphosphite (95 g, 0.57 mol) were mixed, and the mixture was stirred at 110° C. for 3 days. The reaction mixture was dried under reduced pressure to give the title compound.

$^1$H-NMR(400 MHz, CDCl$_3$) δ 4.20-4.05(4H, m), 3.76(3H, s), 2.88(1H, ddd, J=22.4, 10.4, 4.0 Hz), 2.18-1.98(2H, m), 1.35-1.30(6H, m), 1.19(3H, t, J=8.0 Hz).

Step 2. Synthesis of 5-[(1E)-2-(methoxycarbonyl)-but-1-en-1-yl]thiophene-2-carboxylic acid tert-butyl ester 2-(diethylphosphono)butyric acid methyl ester (46 g, 0.193 mol) was dissolved in tetrahydrofuran (300 mL), 60% sodium hydride (6.6 g, 0.165 mol) was added at 0° C., and the mixture was stirred for 30 minutes. To the reaction mixture was added a solution of 5-formyl-2-thiophenecarboxylic acid tert-butyl ester obtained in Example 1, step 2(32.1 g, 0.15 mol) in tetrahydrofuran (10 mL), and the mixture was stirred at room temperature for 2 hours. The solvent was evaporated, and the residue was partitioned between ethyl acetate and 1N-hydrochloric acid solution, and washed successively with water and brine. After drying over anhydrous magnesium sulfate, the residue was purified by silica gel column chromatography to give the title compound (35.6 g, 0.12 mol, 80%).

$^1$H-NMR(400 MHz, CDCl$_3$) δ 7.71(1H, s), 7.65(1H, d, J=4.0 Hz), 7.17(1H, d, J=4.0 Hz), 3.82(3H, s), 2.73(2H, q, J=7.6 Hz), 1.56(9H, s), 1.18(311, t, J=7.6 Hz).

Step 3. Synthesis of (E)-3-(5-tert-butoxycarbonylthiophen-2-yl)-2-ethyl-propenoic acid 5-[(1E)-2-(methoxycarbonyl)-but-1-en-1-yl]thiophene-2-carboxylic acid tert-butyl ester (34.6 g, 120 mol) was dissolved in tetrahydrofuran (150 mL), and methanol (60 mL), 1 N lithium hydroxide solution (144 mL, 144 mmol) was added, and the mixture was stirred at room temperature for 2 days. The mixture was concentrated under reduced pressure. 0.5 N-Hydrochloric acid solution and ethyl acetate were added to the obtained residue, the organic layer was extracted, and the aqueous layer was extracted three times with ethyl acetate. The organic layers were collected, washed with brine, and dried over anhydrous magnesium sulfate. After filtration, the solvent of the filtrate was evaporated under reduced pressure to give the title compound (32.2 g, 114 mmol, 95%).

¹H-NMR(400 MHz, CDCl₃) δ 7.82(1H, s), 7.66(1H, d, J=4.0 Hz), 7.21(1H, d, J=4.0 Hz), 2.74(2H, q, J=7.6 Hz), 1.59(9H, s), 1.21(3H, t, J=7.6 Hz).

Step 4. Synthesis of 2-((5-tert-butoxycarbonylthiophen-2-yl)methyl)-butanoic acid 5-[((1E)-2-Methoxycarbonyl)-but-1-en-1-yl]thiophene-2-carboxylic acid (20.43 g, 72.4 mmol) was dissolved in ethyl acetate (300 mL), methanol (20 mL) and chloroform (10 mL), palladium hydroxide (2.0 g) was added, and the mixture was stirred at room temperature overnight under a hydrogen atmosphere. After completion of the reaction, palladium hydroxide was removed by celite filtration, and the solvent was evaporated under reduced pressure to give the title compound (20.6 g, quantitative).

Step 5. Synthesis of 5-(2-benzyloxycarbonylbutyl)thiophene-2-carboxylic acid tert-butyl ester 2-(5-tert-Butoxycarbonylthiophen-2-yl)methyl-butanoic acid (20.6 g, 72.2 mmol) was dissolved in N,N-dimethylformamide (100 mL), potassium carbonate (10.4 g, 75.3 mmol) and benzyl bromide (13.0 g, 76.0 mmol) were added, and the mixture was stirred at room temperature overnight. The reaction mixture was filtered through celite, and the filtrate was concentrated under reduced pressure. 0.5 N-Hydrochloric acid solution and ethyl acetate were added to the obtained residue, the organic layer was extracted, and the aqueous layer was extracted three times with ethyl acetate. The organic layers were collected, washed with brine, and dried over anhydrous magnesium sulfate. After filtration, the solvent of the filtrate was evaporated under reduced pressure. The obtained residue was purified by silica gel column chromatography to give the title compound (27.0 g, 72.1 mmol, 96%).
¹H-NMR(400 MHz, CDCl₃) δ 7.49(1H, d, J=3.6 Hz), 7.35-7.25(5H, m), 6.71(1H, d, J=3.6 Hz), 5.11(1H, d, J=12.4 Hz), 5.07(1H, d, J=12.4 Hz), 3.16(1H, dd, J=14.8, 8.8 Hz), 2.96 (1H, dd, J=14.8, 6.0 Hz), 2.72(1H, m), 1.73-1.60(2H, m), 1.56(9H, s), 0.92(3H, t, J=7.6 Hz).

Step 6. Synthesis of 5-(2-benzyloxycarbonyl-2-ethyl-butyl)thiophene-2-carboxylic acid tert-butyl ester 5-(2-Benzyloxycarbonylbutyl)thiophene-2-carboxylic acid tert-butyl ester (29.5 g, 78.8 mmol) was dissolved in tetrahydrofuran (200 mL), 1.09 M lithium bis(trimethylsilyl) azanide/tetrahydrofuran solution (94 mL, 102 mmol) was added dropwise at −78° C., and the mixture was stirred for 2 hours. To the reaction mixture was added ethyl iodide (12.3 g, 156 mmol) at −78° C., and the mixture was stirred at room temperature overnight. The reaction mixture was concentrated under reduced pressure. The residue was added to ethyl acetate and 0.5 N-hydrochloric acid solution, the organic layer was extracted, and the aqueous layer was extracted two times with ethyl acetate. The organic layers were collected, washed with sodium thiosulfate solution and brine, and dried over anhydrous magnesium sulfate, and concentrated under reduced pressure. The obtained residue was purified by silica gel column chromatography to give the title compound (24.9 g, 61.9 mmol, 78%).
¹H-NMR(400 MHz, CDCl₃) δ 7.49(1H, d, J=4.0 Hz), 7.40-7.30(5H, m), 6.67(1H, d, J=4.0 Hz), 5.15(2H, s), 3.11(2H, s), 1.70-1.59(4H, m), 1.56(9H, s), 0.85(6H, t, J=7.6 Hz).

Step 7. Synthesis of 5-(2-benzyloxycarbonyl-2-ethyl-butyl)thiophene-2-carboxylic acid To 5-(2-Benzyloxycarbonyl-2-ethyl-butyl)thiophene-2-carboxylic acid tert-butyl ester (24.9 g, 61.9 mmol) was added trifluoroacetic acid (20 mL), and the mixture was stirred at room temperature for 2 hours. The solvent was evaporated to give the title compound (quantitative)

Step 8. Synthesis of 3-[5-(4-amidino-2-fluorophenoxycarbonyl)thiophen-2-yl]-2,2-diethylpropanoic acid benzyl ester trifluoroacetic acid salt 5-(2-Benzyloxycarbonyl-2-ethyl-butyl)thiophene-2-carboxylic acid (5.0 g, 14.4 mmol) was dissolved in N-methylpyrrolidone (5 mL), and dichloromethane (5 mL), thionylchloride (1.27 mL, 17.6 mmol) was added at 0° C., and the mixture was stirred for 15 minutes at 0° C. 3-fluoro-4-hydroxybenzamidine hydrochloride (2.7 g, 14.2 mmol) and pyridine (7 mL) were added to the reaction mixture, and the mixture was stirred for 2 hours at room temperature. The reaction mixture was concentrated under reduced pressure, and the obtained residue was purified by high performance liquid chromatography ( water-acetonitrile, each containing 0.1% trifluoroacetic acid) to give the title compound (4.3 g, 7.21 mmol, 51%).
MS(ESI) m/z 483(M+H)+

Step 9. Synthesis of 3-[5-(4-amidino-2-fluorophenoxycarbonyl)thiophen-2-yl]-2,2-diethylpropanoic acid trifluoroacetic acid salt (compound 18)

3-[5-(4-Amidino-2-fluorophenoxycarbonyl)pthiophen-2-yl]-2,2-diethylpropanoic acid benzyl ester trifluoroacetic acid salt (4.3 g, 7.21 mmol) was dissolved in 2-propanol (160 mL) and water (40 mL), palladium hydroxide (0.9 g) was added, and the mixture was stirred at room temperature overnight under a hydrogen atmosphere. The reaction mixture was filtered through celite, and the filtrate was concentrated under reduced pressure. Water and acetonitrile were added to the residue, the mixture was lyophilized to give the title compound (3.61 g, 7.12 mmol, 99%).
¹H-NMR(400 MHz, DMSO-d6) δ 9.42(2H, br s), 9.24(2H, br s), 7.97(1H, d, J=4.0 Hz), 7.94(1H, d, J=10.4 Hz), 7.80-7.70(2H, m), 7.10(1H, d, J=4.0 Hz), 3.15(2H, s), 1.60-1.40 (4H, m), 0.85(6H, t, J=7.6 Hz).
MS(ESI) m/z 393(M+H)+

Example 6

Synthesis of N-{3-[5-(4-amidino-2-fluoro-phenoxycarbonyl)thiophen-2-yl]-2,2-diethylpropionyl}-L-serine hydrochloride (compound 11)

3-[5-(4-Amidino-2-fluorophenoxycarbonyl)thiophen-2-yl]-2,2-diethylpropanoic acid trifluoroacetic acid salt (compound 18) (616 mg, 1.2 mmol) was dissolved in thionyl chloride (6 mL), and the mixture was stirred at 60° C. for 20 minutes. Thionyl chloride was evaporated under reduced pressure to give the acid chloride. The obtained acid chloride was dissolved in dichloromethane (20 mL), O-tert-butyl-1-serine tert-butyl ester hydrochloride (334 mg, 1.32 mmol) and pyridine (0.5 mL) were added thereto, and the mixture was stirred at room temperature overnight. After evaporation of the solvent, trifluoroacetic acid (5 mL) was added, and the mixture was stirred at room temperature for 30 minutes. The mixture was concentrated under reduced pressure. The obtained residue was purified by high performance liquid chromatography (water-acetonitrile, each containing 0.1% trifluoroacetic acid) to give the trifluoroacetic acid salt of the title compound.

To the obtained trifluoroacetic acid salt was added 0.05 N-hydrochloric acid solution (30 mL), and the mixture was lyophilized to give the title compound (513 mg, 0.99 mmol, 83%).

$^1$H-NMR(400 MHz, DMSO-d6) δ 9.41(2H, br s), 9.10(2H, br s), 7.95-7.90(2H, m), 7.78-7.72(2H, m), 7.63(1H, d, J=7.6 Hz), 7.10(1H, d, J=4.0 Hz), 4.34(1H, m), 3.75-3.64(1H, m), 3.64-3.56(1H, m), 3.16(2H, s), 1.62-1.46(4H, m), 0.88-0.78 (6H, m).

MS(ESI) m/z 480(M+H)+

Example 7

Synthesis of N-{3-[5-(4-amidino-2-fluoro-phenoxycarbonyl)thiophen-2-yl]-2,2-diethylpropionyl}-sarcosine hydrochloride (compound 21)

Step 1. Synthesis of N-{3-[5-(4-amidino-2-fluorophenoxycarbonyl)thiophen-2-yl]-2,2-diethylpropionyl}-sarcosine benzyl ester trifluoroacetic acid salt 3-[5-(4-Amidino-2-fluorophenoxycarbonyl)thiophen-2-yl]-2,2-diethylpropanoic acid trifluoroacetic acid salt (compound 18) (100 mg, 0.20 mmol) was dissolved in thionyl chloride (2 mL), and the mixture was stirred at room temperature for 30 minutes. Thionyl chloride was evaporated under reduced pressure to give the acid chloride. The obtained acid chloride was dissolved in 1,2-dichloroethane (5 mL), sarcosine benzyl ester hydrochloride (47 mg, 0.22 mmol) and pyridine (0.2 mL) were added thereto, and the mixture was stirred at 60° C. for 5 hours. The mixture was concentrated under reduced pressure. The obtained residue was purified by high performance liquid chromatography (water-acetonitrile, each containing 0.1% trifluoroacetic acid) to give the title compound (83 mg, 0.12 mmol, 62%).

Step 2. Synthesis of N-{3-[5-(4-amidino-2-fluorophenoxycarbonyl)thiophen-2-yl]-2,2-diethylpropionyl}-sarcosine hydrochloride (compound 21)

N-{3-[5-(4-amidino-2-fluoro-phenoxycarbonyethiophen-2-yl]-2,2-diethylpropionyl}-sarcosine benzyl ester trifluoroacetic acid salt (83 mg, 0.12 mmol) was dissolved in 2-propanol (5 mL) and water (5 mL), palladium hydroxide (50 mg) was added, and the mixture was stirred at room temperature for 2 hours under a hydrogen atmosphere. The mixture was concentrated under reduced pressure. The obtained residue was purified by high performance liquid chromatography (water-acetonitrile, each containing 0.1% trifluoroacetic acid) to give the trifluoroacetic acid salt of the title compound. To the obtained trifluoroacetic acid salt were added 0.01N-hydrochloric acid solution (30 mL), and the mixture was lyophilized to give the title compound (32 mg, 0.064 mmol, 53%).

1H-NMR(400 MHz, DMSO-d6) δ 9.35(2H, br s), 9.22(2H, br s), 7.90-7.85(2H, m), 7.70-7.65(2H, m), 7.06(1H, d, J=3.6 Hz), 3.92(2H, m), 3.15(3H, s), 3.12(2H, br s), 1.70-1.60(2H, m), 1.60-1.50(2H, m), 0.76(6H, t, J=7.2 Hz).

MS(ESI) m/z 464(M+H)+

Example 8

Synthesis of N-allyl-N-{3-[5-(4-amidino-2-fluorophenoxycarbonyl)-thiophen-2-yl]-2,2-dimethylpropionyl}taurine (compound 23)

Step 1. Synthesis of N-allyltaurine isopropyl ester

2-Chloroethylsulfonyl chloride (2 g, 12.3 mmol) was dissolved in 2-propanol (20 mL), pyridine (2.7 mL) was added, and the mixture was stirred at room temperature for 3 hours. Allylamine hydrochloride (1.15 g, 12.3 mmol) and diisopropylethylamine (6.4 ml) was added, and stirred at room temperature for 3 hours. The reaction mixture was evaporated under reduced pressure, 5% sodium bicarbonate solution was added to the residue, and the mixture was extracted with ethyl acetate. The extract was washed with brine, dried over anhydrous magnesium sulfate and concentrated under reduced pressure. The obtained residue was purified by silica gel column chromatography to give the title compound (0.5 g, 2.4 mmol, 20%).

$^1$H-NMR(400 MHz, CDCl$_3$) δ 6.55(1H, dd, J=10.0, 16.8 Hz), 6.39(1H, d, J=16.8 Hz), 6.07(1H, d, J=10.0 Hz), 4.81 (1H, sep, J=6.3 Hz), 1.40(6H, d, J=6.3 Hz).

MS(ESI) m/z 208 (M+H)+

Step 2. Synthesis of N allyl-N-{3-[5-(4-amidino-2-fluoro-phenoxycarbonyl)thiophen-2-yl]-2,2-dimethylpropionyl}taurine (compound 23)

3-[5-(4-Amidino-2-fluorophenoxycarbonyl)thiophen-2-yl]-2,2-dimethylpropanoic acid trifluoroacetic acid salt (200 mg, 0.40 mmol) obtained in Example 3, step 5 was dissolved in thionyl chloride (4 mL), and the mixture was stirred at room temperature for 30 minutes. Thionyl chloride was evaporated under reduced pressure to give the acid chloride. The obtained acid chloride was dissolved in 1,2-dichloroethane (10 mL), N-allyltaurine isopropyl ester obtained in step 1(88 mg, 0.43 mmol) and pyridine (0.4 mL) were added thereto, and the mixture was stirred at 50° C. overnight. The mixture was concentrated under reduced pressure. The obtained residue was purified by high performance liquid chromatography (water-acetonitrile, each containing 0.1% trifluoroacetic acid) to give the isopropyl ester of the title compound. The obtained solid was dissolved in 0.01 N aqueous hydrochloric acid (20 ml) solution and stirred at room temperature for 5 hours, and the precipitated solid was collected by filtration. The solid was washed with water and dried to give the title compound (47 mg, 0.092 mmol, 23%).

1H-NMR(400 MHz, DMSO-d6) δ 9.41(2H, br s), 9.02(2H, br s), 7.95-7.88(2H, m), 7.81-7.70(2H, m), 7.10(1H, d, J=3.6 Hz), 5.76(1H, m), 5.20-5.05(2H, m), 4.15-3.85(2H, m), 3.70-3.45(2H, m), 3.21(2H, s), 2.67(2H, m), 1.26(6H, s).

MS(ESI) m/z 512 (M+H)+

Example 9

Synthesis of N-{3-[5-(4-amidino-2-fluoro-phenoxycarbonyl)thiophen-2-yl]-2,2-diethylpropionyl}-beta-homoisoleucine hydrochloride (compound 49)

The compound 18(76 mg, 0.15 mmol) was dissolved in thionyl chloride (1.5 mL), and the mixture was stirred at room temperature for 30 minutes. Thionyl chloride was evaporated under reduced pressure to give the acid chloride. The obtained acid chloride was dissolved in dichloromethane (1.5 mL), beta-homoisoleucine methyl ester hydrochloride (44 mg, 0.225 mmol) and pyridine (0.2 mL) were added thereto, and the mixture was stirred at room temperature overnight. After evaporation of the solvent, trifluoroacetic acid (5 mL) was added, and the mixture was stirred at 60° C. for 1 hour. The mixture was concentrated under reduced pressure. After evaporation of the solvent, 4 N-hydrogen chloride in 1,4-dioxane (2 mL) and water (1 mL) were added, and the mixture was stirred at 80° C. 30 minutes. The mixture was concentrated under reduced pressure. The obtained residue was purified by high performance liquid chromatography (water-acetonitrile, each containing 0.1% trifluoroacetic acid) to give the trifluoroacetic acid salt of the title compound.

To the obtained trifluoroacetic acid salt was added 0.1 N-hydrochloric acid solution (10 mL), and the mixture was lyophilized to give the title compound (35.6 mg, 0.064 mmol, 43%).

1H NMR (400 MHz, DMSO-d™$_6$) δ12.09 (1H, s), 9.44 (2H, s), 9.17 (2H, s), 7.98-7.91 (2H, m), 7.78-7.72 (2H, m), 7.37 (1H, d, J=8.2 Hz), 7.06 (1H, d, J=3.8 Hz), 4.19-4.09 (1H, m), 3.17-3.06 (2H, m), 2.43-2.30 (2H, m), 1.63-1.44 (4H, m), 1.40-1.27 (1H, m), 1.11-0.98 (1H, m), 0.89-0.73 (10H, m)

MS(ESI) m/z 520 (M+H)+

The compounds 39, 40, 45, 46, 51, 55, 63, 64, 65, 68 and 81 shown in the following Table 1 were each synthesized using the compound 16 or the compound obtained in Example 3, step 5 and commercially available reagents and by an operation in the same manner as in the above-mentioned Example 4, step 2.

The compounds 3, 4, 6, 12, 13, 14, 15, 16, 19, 24, 25, 27, 28, 29, 30, 31, 34, 42, 43, 44, 52, 58 and 83 shown in the following Table 1 were each synthesized using the compound 16 or the compound obtained in Example 3, step 5 and commercially available reagents and by an operation in the same manner as in the above-mentioned Example 6.

The compounds 7, 8, 17, 20, 22, 26, 32, 33, 41, 48, 56, 57, 62, 66, 67, 69, 70, 71, 73, 75, 76, 77, 78, 79, 80, 84, 85 and 86 shown in the following Table 1 were each synthesized using the compound 16 or the compound obtained in Example 3, step 5 and commercially available reagents and by an operation in the same manner as in the above-mentioned Example 7.

The compounds 5, 35, 36, 37, 38, 47, 50, 53, 54, 59, 60, 61, 72, 74 and 82 shown in the following Table 1 were each synthesized using the compound 16 or the compound obtained in Example 3, step 5 and commercially available reagents and by an operation in the same manner as in the above-mentioned Example 9.

TABLE 1-1

| Compound No. | Structure | Analysis data |
|---|---|---|
| 1 | 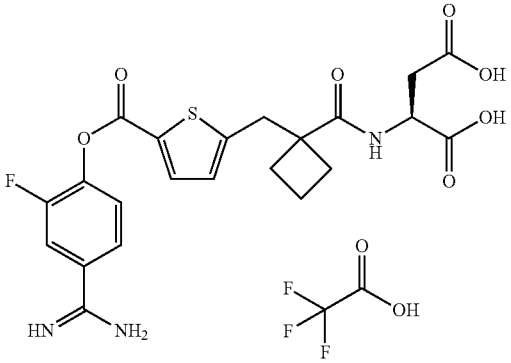 [SMILES: N=C(N)c1ccc(OC(=O)c2ccc(CC3(C(=O)N[C@@H](CC(=O)O)C(=O)O)CCC3)s2)c(F)c1 ; O=C(O)C(F)(F)F] | 1H-NMR (400 MHz, DMSO-d6) δ 9.42 (2H, br s), 9.09 (2H, br s), 8.07 (1H, d, J = 8.0 Hz), 7.99-7.83 (2H, m), 7.92-7.82 (1H, m), 7.79-7.69 (2H, m), 7.06 (1H, d, J = 3.9 Hz), 4.56 (1H, dd, J = 13.9, 7.6 Hz), 3.48 (2H, s), 2.74 (1H, dd, J = 16.4, 6.0 Hz), 2.64-2.49 (1H, m), 2.40-2.25 (2H, m), 2.05-1.83 (3H, m), 1.80-1.69 (1H, m). MS(ESI) m/z 492 (M + H)+ |
| 2 | 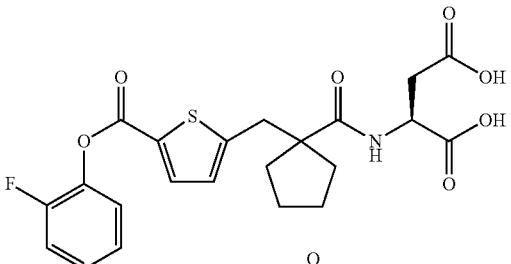 | 1H-NMR (400 MHz, DMSO-d6) δ 9.36 (2H, br s), 9.08 (2H, br s), 7.97 (1H, d, J = 7.9 Hz), 7.89-7.80 (2H, m), 7.72-7.63 (2H, m), 7.00 (1H, d, J = 3.9 Hz), 4.49 (2H, dt, J = 12.9, 6.4 Hz), 3.17 (2H, s), 2.69 (1H, dd, J = 16.4, 6.0 Hz), 2.57-2.45 (2H, m), 2.02-1.81 (2H, m), 1.63-1.37 (6H, m). MS(ESI) m/z 506 (M + H)+ |

TABLE 1-1-continued

| Compound No. | Structure | Analysis data |
|---|---|---|
| 3 | (structure) | 1H NMR (400 MHz, DMSO-d6) δ 9.42 (2H, br s), 9.17 (2H, br s), 8.12-7.98 (1H, m), 7.98-7.87 (2H, m), 7.83-7.68 (2H, m), 7.08 (1H, d, J = 3.9 Hz), 3.73 (2H, d, J = 5.8 Hz), 3.12 (2H, s), 1.13 (6H, s)<br>MS(ESI) m/z 422 (M + H)+ |
| 4 | (structure) | 1H NMR (400 MHz, DMSO-d6) δ 9.41 (2H, br s), 9.07 (2H, br s), 7.98-7.87 (2H, m), 7.82-7.69 (2H, m), 7.56 (1H, d, J = 7.8 Hz), 7.09 (1H, d, J = 3.9 Hz), 4.30 (1H, dt, J = 7.9, 5.0 Hz), 3.70 (2H, ddd, J = 15.2, 11.1, 4.9 Hz), 3.16 (2H, s), 1.17 (6H, s)<br>MS(ESI) m/z 452 (M + H)+ |
| 5 | (structure) | MS(ESI) m/z 462 (M + H)+ |
| 6 | (structure) | 1H NMR (400 MHz, DMSO-d6) δ 9.41 (2H, br s), 9.12 (2H, br s), 8.00-7.87 (2H, m), 7.81-7.68 (2H, m), 7.54 (1H, s), 7.08 (1H, d, J = 3.8 Hz). 3.13 (2H, s), 1.36 (6H, s), 1.14 (6H, s)<br>MS(ESI) m/z 450 (M + H)+ |
| 7 | (structure) | 1H NMR (400 MHz, DMSO-d6) δ 9.41 (2H, br s), 9.18 (2H, br s), 7.98-7.88 (2H, m), 7.81-7.70 (2H, m), 7.12 (1H, d, J = 3.8 Hz), 3.99 (3H, s), 3.21 (2H, s), 1.26 (6H, s)<br>MS(ESI) m/z 436 (M + H)+ |

TABLE 1-1-continued

| Compound No. | Structure | Analysis data |
|---|---|---|
| 8 | 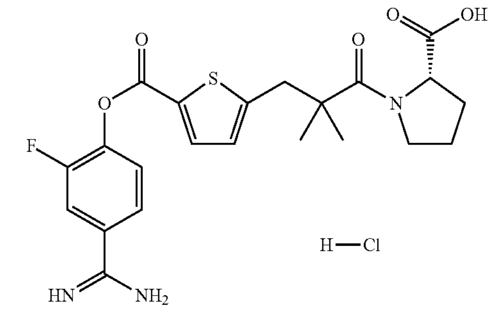 [SMILES: CC(C)(Cc1ccc(C(=O)Oc2ccc(C(=N)N)cc2F)s1)C(=O)N1CCC[C@H]1C(=O)O ; Cl] | MS(ESI) m/z 462 (M + H)+ |
| 9 | 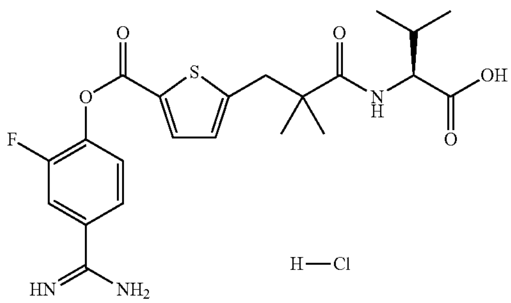 [SMILES: CC(C)[C@H](NC(=O)C(C)(C)Cc1ccc(C(=O)Oc2ccc(C(=N)N)cc2F)s1)C(=O)O ; Cl] | 1H-NMR (400 MHz, DMSO-d6) δ 9.41 (2H, br s), 9.10 (2H, br s), 8.00-7.89 (2H, m), 7.80-7.70 (2H, m), 7.57 (1H, d, J = 7.2 Hz), 7.08 (1H, s), 4.13 (1H, m), 3.21 (1H, d, J = 16.0 Hz), 3.15 (1H, d, J = 16.0 Hz), 2.15-2.05 (1H, m), 1.76-1.50 (4H, m), 0.90 (3H, d, J = 6.8 Hz), 0.86-0.75 (6H, m). MS(ESI) m/z 464 (M + H)+ |
| 10 | 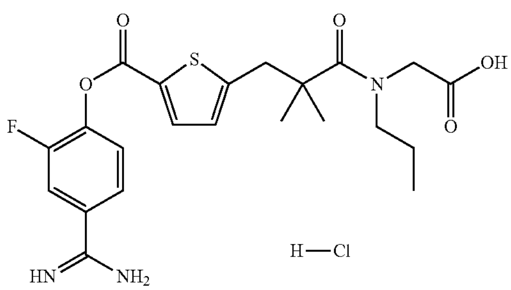 [SMILES: CCCN(CC(=O)O)C(=O)C(C)(C)Cc1ccc(C(=O)Oc2ccc(C(=N)N)cc2F)s1 ; Cl] | 1H-NMR (400 MHz, DMSO-d6) δ 9.41 (2H, br s), 9.05 (2H, br s), 7.93 (2H, m), 7.74 (2H, m), 7.11 (1H, d, J = 3.6 Hz), 3.75-3.65 (2H, m), 3.18 (2H, s), 1.58-1.48 (2H, m), 1.25 (6H, br s), 0.84 (3H, m). MS(ESI) m/z 464 (M + H)+ |
| 11 | 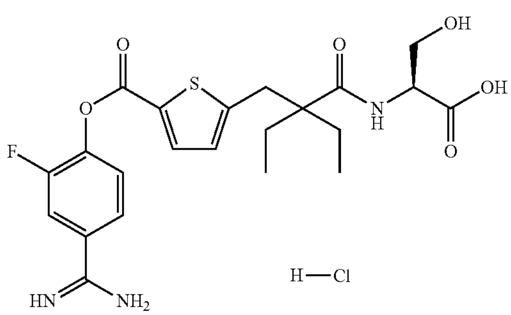 [SMILES: CCC(CC)(Cc1ccc(C(=O)Oc2ccc(C(=N)N)cc2F)s1)C(=O)N[C@@H](CO)C(=O)O ; Cl] | 1H-NMR (400 MHz, DMSO-d6) δ 9.41 (2H, br s), 9.10 (2H, br s), 7.95-7.90 (2H, m), 7.78-7.72 (2H, m), 7.63 (1H, d, J = 7.6 Hz), 7.10 (1H, d, J = 4.0 Hz), 4.34 (1H, m), 3.75-3.64 (1H, m), 3.64-3.56 (1H, m), 3.16 (2H, s), 1.62-1.46 (4H, m), 0.88-0.78 (6H, m). MS(ESI) m/z 480 (M + H)+ |
| 12 | 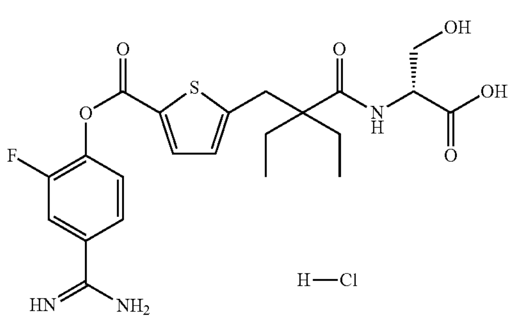 [SMILES: CCC(CC)(Cc1ccc(C(=O)Oc2ccc(C(=N)N)cc2F)s1)C(=O)N[C@H](CO)C(=O)O ; Cl] | 1H-NMR (400 MHz, DMSO-d6) δ 9.37 (4H, br s), 7.95-7.88 (2H, m), 7.78-7.72 (2H, m), 7.56 (1H, d, J = 6.8 Hz), 7.10 (1H, d, J = 3.6 Hz), 4.23 (1H, m), 3.72-3.68 (1H, m), 3.65-3.58 (1H, m), 3.16 (2H, s), 1.62-1.49 (4H, m), 0.88-0.80 (6H, m). MS(ESI) m/z 480 (M + H)+ |

TABLE 1-1-continued

| Compound No. | Structure | Analysis data |
|---|---|---|
| 13 | 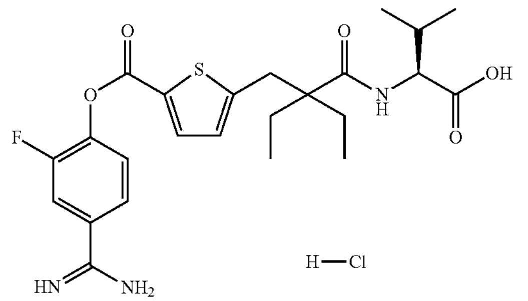 [SMILES: CCC(CC)(Cc1ccc(C(=O)Oc2ccc(C(=N)N)cc2F)s1)C(=O)N[C@H](C(=O)O)C(C)C ; Cl] | 1H-NMR (400 MHz, DMSO-d6) δ 9.41 (2H, br s), 9.10 (2H, br s), 7.95-7.88 (2H, m), 7.80-7.70 (2H, m), 7.57 (1H, d, J = 7.2 Hz), 7.08 (1H, d, J = 3.6 Hz), 4.13 (1H, m), 3.23-3.10 (2H, m), 2.08 (1H, m), 1.65-1.45 (4H, m), 0.90 (6H, d, J = 6.8 Hz), 0.88-0.80 (6H, m). MS(ESI) m/z 492 (M + H)+ |
| 14 | 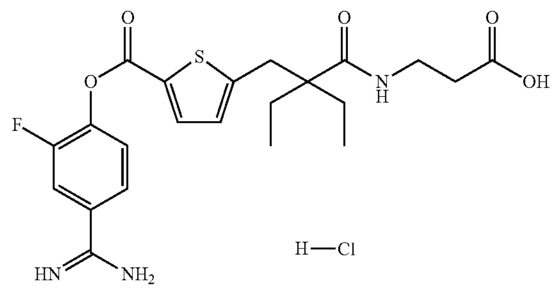 [SMILES: CCC(CC)(Cc1ccc(C(=O)Oc2ccc(C(=N)N)cc2F)s1)C(=O)NCCC(=O)O ; Cl] | 1H-NMR (400 MHz, DMSO-d6) δ 9.39 (2H, br s), 9.10 (2H, br s), 7.90-7.85 (2H, m), 7.75-7.65 (3H, m), 6.97 (1H, d, J = 2.4 Hz), 3.30 (2H, m), 3.05 (2H, s), 2.35 (2H, t, J = 6.4 Hz), 1.50-1.30 (4H, m), 0.75-0.65 (6H, t, J = 7.2 Hz). MS(ESI) m/z 464 (M + H)+ |
| 15 | 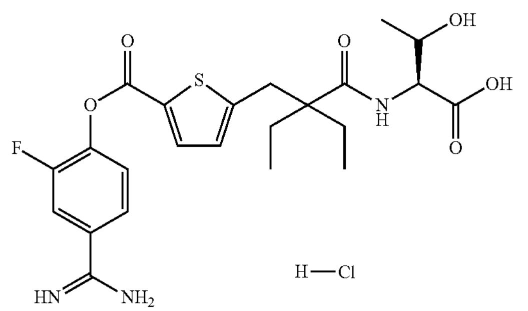 [SMILES: CCC(CC)(Cc1ccc(C(=O)Oc2ccc(C(=N)N)cc2F)s1)C(=O)N[C@H](C(=O)O)C(C)O ; Cl] | 1H-NMR (400 MHz, DMSO-d6) δ 9.41 (2H, br s), 9.18 (2H, br s), 7.95-7.90 (2H, m), 7.78-7.72 (2H, m), 7.18 (1H, d, J = 8.0 Hz), 7.10 (1H, d, J = 4.0 Hz), 4.22 (1H, m), 4.12 (1H, m), 3.16 (2H, s), 1.62-1.49 (4H, m), 1.03 (3H, d, J = 6.4 Hz), 0.88-0.80 (6H, t, J = 7.2 Hz). MS(ESI) m/z 494 (M + H)+ |
| 16 | 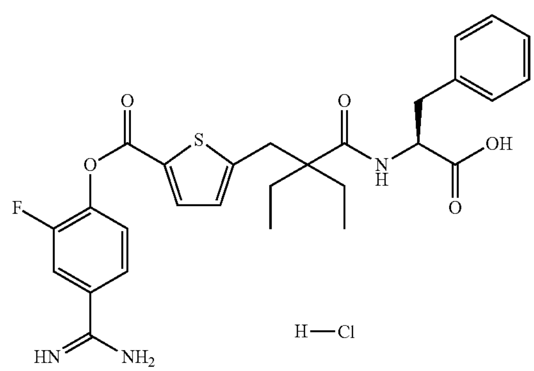 [SMILES: CCC(CC)(Cc1ccc(C(=O)Oc2ccc(C(=N)N)cc2F)s1)C(=O)N[C@@H](Cc1ccccc1)C(=O)O ; Cl] | 1H-NMR (400 MHz, DMSO-d6) δ 9.44 (4H, br s), 7.95 (1H, d, J = 11.2 Hz), 7.88-7.80 (2H, m), 7.78-7.70 (2H, m), 7.30-7.20 (4H, m), 7.20-7.12 (1H, m), 6.88 (1H, d, J = 4.0 Hz), 4.54 (1H, m), 3.18-2.92 (4H, m), 1.55-1.30 (4H, m), 0.72 (3H, t, J = 7.2 Hz), 0.53 (3H, t, J = 7.2 Hz). MS(ESI) m/z 540 (M + H)+ |
| 17 | 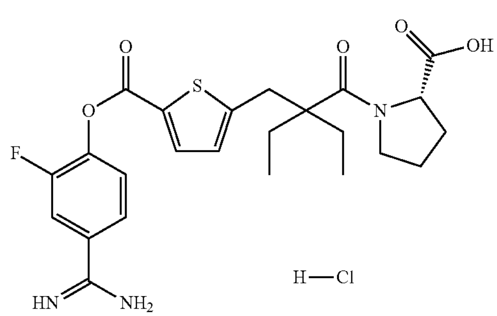 [SMILES: CCC(CC)(Cc1ccc(C(=O)Oc2ccc(C(=N)N)cc2F)s1)C(=O)N1CCC[C@H]1C(=O)O ; Cl] | 1H-NMR (400 MHz, DMSO-d6) δ 9.43 (2H, br s), 9.16 (2H, br s), 7.98-7.92 (2H, m), 7.80-7.70 (2H, m), 7.11 (1H, d, J = 4.0 Hz), 4.39 (1H, m), 3.78-3.60 (2H, m), 3.24 (1H, d, J = 15.2 Hz), 3.16 (1H, d, J = 15.2 Hz), 2.10 (1H, m), 2.00-1.85 (2H, m), 1.80-1.45 (5H, m), 0.88 (3H, t, J = 7.2 Hz), 0.78 (3H, t, J = 7.2 Hz). MS(ESI) m/z 490 (M + H)+ |

TABLE 1-1-continued

| Compound No. | Structure | Analysis data |
|---|---|---|
| 18 | 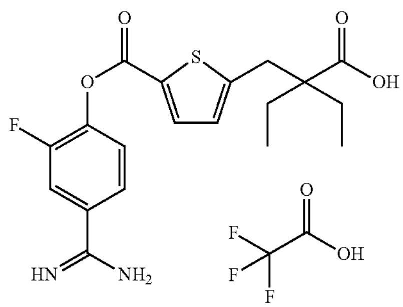 | 1H-NMR (400 MHz, DMSO-d6) δ 9.42 (2H, br s), 9.24 (2H, br s), 7.97 (1H, d, J = 4.0 Hz), 7.94 (1H, d, J = 10.4 Hz), 7.80-7.70 (2H, m), 7.10 (1H, d, J = 4.0 Hz), 3.15 (2H, s), 1.60-1.40 (4H, m), 0.85 (6H, t, J = 7.6 Hz). MS(ESI) m/z 393 (M + H)+ |
| 19 | 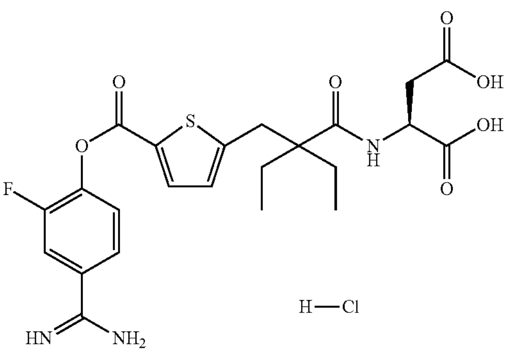 [SMILES: CCC(CC)(Cc1ccc(C(=O)Oc2ccc(C(=N)N)cc2F)s1)C(=O)N[C@@H](CC(=O)O)C(=O)O ; Cl] | 1H-NMR (400 MHz, DMSO-d6) δ 9.39 (2H, br s), 9.12 (2H, br s), 7.90-7.85 (3H, m), 7.70-7.65 (2H, m), 7.02 (1H, d, J = 4.0 Hz), 4.50 (1H, m), 3.06 (2H, s), 2.70 (1H, dd, J = 16.4, 6.0 Hz), 2.51 (1H, dd, J = 16.4, 7.2 Hz), 1.50-1.38 (4H, m), 0.80-0.70 (6H, m). MS(ESI) m/z 508 (M + H)+ |
| 20 | 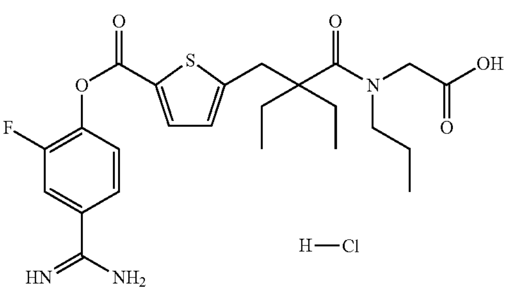 [SMILES: CCCN(CC(=O)O)C(=O)C(CC)(CC)Cc1ccc(C(=O)Oc2ccc(C(=N)N)cc2F)s1 ; Cl] | 1H-NMR (400 MHz, DMSO-d6) δ 9.46 (4H, br s), 8.00-7.92 (2H, m), 7.80-7.70 (2H, m), 7.13 (1H, d, J = 3.6 Hz), 3.89 (2H, m), 3.40 (2H, m), 3.21 (2H, s), 1.80-1.40 (6H, m), 0.90-0.70 (9H, m). MS(ESI) m/z 492 (M + H)+ |
| 21 | 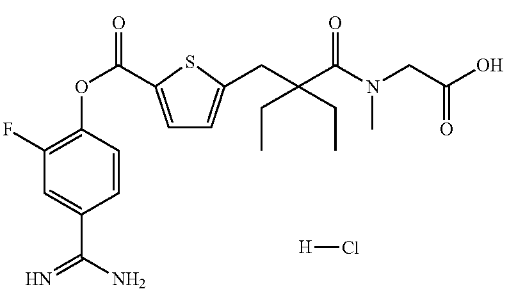 [SMILES: CCC(CC)(Cc1ccc(C(=O)Oc2ccc(C(=N)N)cc2F)s1)C(=O)N(C)CC(=O)O ; Cl] | 1H-NMR (400 MHz, DMSO-d6) δ 9.35 (2H, br s), 9.22 (2H, br s), 7.90-7.85 (2H, m), 7.70-7.65 (2H, m), 7.06 (1H, d, J = 3.6 Hz), 3.92 (2H, m), 3.15 (3H, s), 3.12 (2H, br s), 1.70-1.60 (2H, m), 1.60-1.50 (2H, m), 0.76 (6H, t, J = 7.2 Hz). MS(ESI) m/z 464 (M + H)+ |
| 22 | 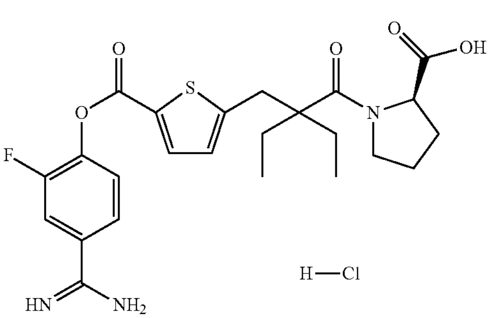 [SMILES: CCC(CC)(Cc1ccc(C(=O)Oc2ccc(C(=N)N)cc2F)s1)C(=O)N1CCC[C@@H]1C(=O)O ; Cl] | 1H-NMR (400 MHz, DMSO-d6) δ 9.46 (2H, br s), 9.21 (2H, br s), 7.98-7.94 (2H, m), 7.78-7.74 (2H, m), 7.11 (1H, d, J = 3.6 Hz), 4.39 (1H, m), 3.78-3.60 (2H, m), 3.24 (1H, d, J = 15.2 Hz), 3.16 (1H, d, J = 15.2 Hz), 2.10 (1H, m), 2.00-1.85 (2H, m), 1.80-1.45 (5H, m), 0.88 (3H, t, J = 7.2 Hz), 0.78 (3H, t, J = 7.2 Hz). MS(ESI) m/z 490 (M + H)+ |

TABLE 1-1-continued

| Compound No. | Structure | Analysis data |
|---|---|---|
| 23 | 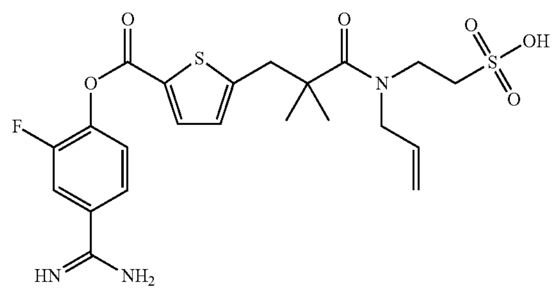 [SMILES: C=CCN(CCS(=O)(=O)O)C(=O)C(C)(C)Cc1ccc(C(=O)Oc2ccc(C(=N)N)cc2F)s1] | 1H-NMR (400 MHz, DMSO-d6) δ 9.41 (2H, br s), 9.02 (2H, br s), 7.95-7.88 (2H, m), 7.81-7.70 (2H, m), 7.10 (1H, d, J = 3.6 Hz), 5.76 (1H, m), 5.20-5.05 (2H, m), 4.15-3.85 (2H, m), 3.70-3.45 (2H, m), 3.21 (2H, s), 2.67 (2H, m), 1.26 (6H, s).<br>MS(ESI) m/z 512 (M + H)+ |
| 24 | 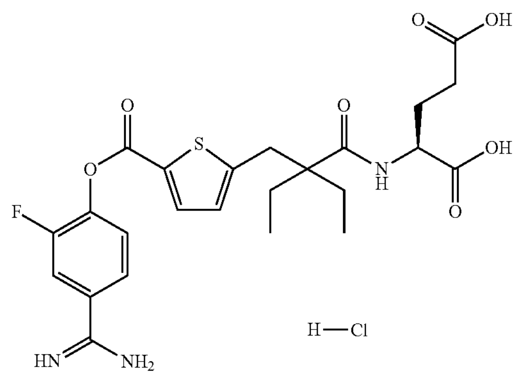 [SMILES: CCC(CC)(Cc1ccc(C(=O)Oc2ccc(C(=N)N)cc2F)s1)C(=O)N[C@@H](CCC(=O)O)C(=O)O ; Cl] | 1H-NMR (400 MHz, DMSO-d6) δ 9.46 (2H, br s), 9.25 (2H, br s), 7.97-7.92 (2H, m), 7.85 (1H, d, J = 7.2 Hz), 7.76-7.74 (2H, m), 7.08 (1H, d, J = 3.6 Hz), 4.25 (1H, m), 3.15 (2H, s), 2.26 (2H, t, J = 8.0 Hz), 2.06-1.95 (1H, m), 1.92-1.80 (1H, m), 1.60-1.46 (4H, m), 0.86-0.79 (6H, m).<br>MS(ESI) m/z 528 (M + H)+ |
| 25 | 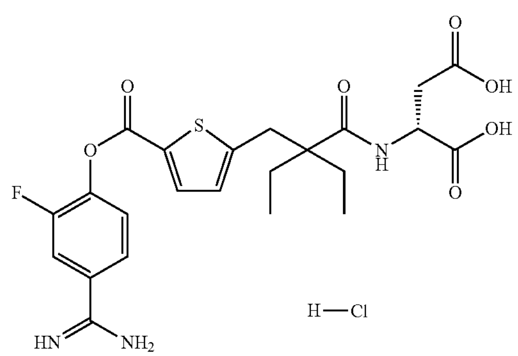 [SMILES: CCC(CC)(Cc1ccc(C(=O)Oc2ccc(C(=N)N)cc2F)s1)C(=O)N[C@H](CC(=O)O)C(=O)O ; Cl] | 1H-NMR (400 MHz, DMSO-d6) δ 9.45 (2H, br s), 9.16 (2H, br s), 7.97-7.92 (3H, m), 7.78-7.72 (2H, m), 7.09 (1H, d, J = 3.6 Hz), 4.57 (1H, m), 3.13 (2H, s), 2.76 (1H, dd, J = 16.4, 5.2 Hz), 2.58 (1H, dd, J = 16.4, 6.4 Hz), 1.56-1.44 (4H, m), 0.86-0.78 (6H, m).<br>MS(ESI) m/z 508 (M + H)+ |
| 26 | 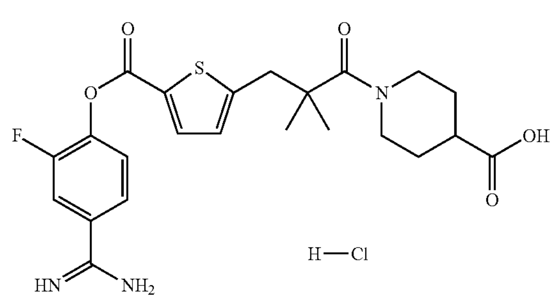 [SMILES: CC(C)(Cc1ccc(C(=O)Oc2ccc(C(=N)N)cc2F)s1)C(=O)N1CCC(C(=O)O)CC1 ; Cl] | 1H NMR (400 MHz, DMSO-d6) δ 9.45 (2H, br s), 9.18 (2H, br s), 7.99-7.88 (2H, m), 7.80-7.71 (2H, m), 7.09 (1H, d, J = 3.8 Hz), 4.20 (2H, d, J = 13.7 Hz), 3.22 (2H, s), 3.06-2.91 (2H, m), 2.61-2.51 (1H, m), 1.93-1.77 (2H, m), 1.50-1.35 (2H, m), 1.24 (6H, s)<br>MS(ESI) m/z 476 (M + H)+ |

TABLE 1-1-continued

| Compound No. | Structure | Analysis data |
| --- | --- | --- |
| 27 | 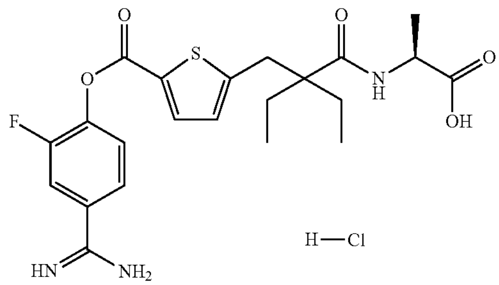 [SMILES: CCC(CC)(Cc1ccc(C(=O)Oc2ccc(C(=N)N)cc2F)s1)C(=O)N[C@@H](C)C(=O)O ; Cl] | MS(ESI) m/z 464 (M + H)+ |
| 28 | 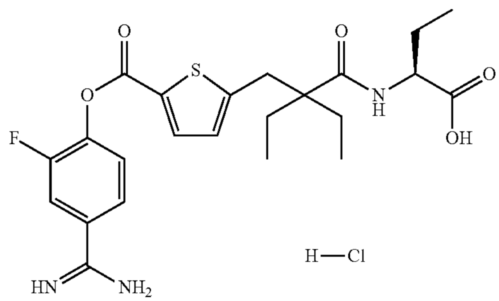 [SMILES: CC[C@H](NC(=O)C(CC)(CC)Cc1ccc(C(=O)Oc2ccc(C(=N)N)cc2F)s1)C(=O)O ; Cl] | MS(ESI) m/z 478 (M + H)+ |
| 29 | 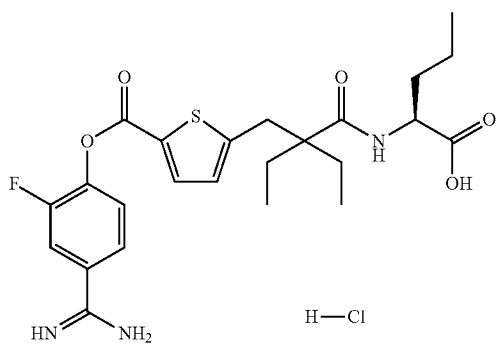 [SMILES: CCC[C@H](NC(=O)C(CC)(CC)Cc1ccc(C(=O)Oc2ccc(C(=N)N)cc2F)s1)C(=O)O ; Cl] | MS(ESI) m/z 492 (M + H)+ |
| 30 | 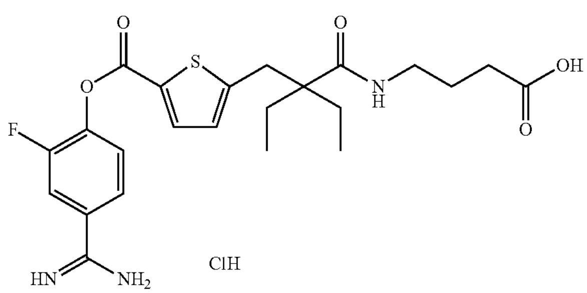 [SMILES: CCC(CC)(Cc1ccc(C(=O)Oc2ccc(C(=N)N)cc2F)s1)C(=O)NCCCC(=O)O ; Cl] | 1H NMR (400 MHz, DMSO-d6) δ 12.05 (1H, s), 9.69-9.03 (4H, m), 7.94 (2H, t, J = 7.6 Hz), 7.80-7.71 (3H, m), 7.04 (1H, d, J = 3.9 Hz), 3.16-3.08 (4H, m), 2.20 (2H, t, J = 7.4 Hz), 1.66 (2H, p, J = 7.2 Hz), 1.60-1.40 (4H, m), 0.80 (6H, t, J = 7.4 Hz) MS(ESI) m/z 478 (M + H)+ |
| 31 | 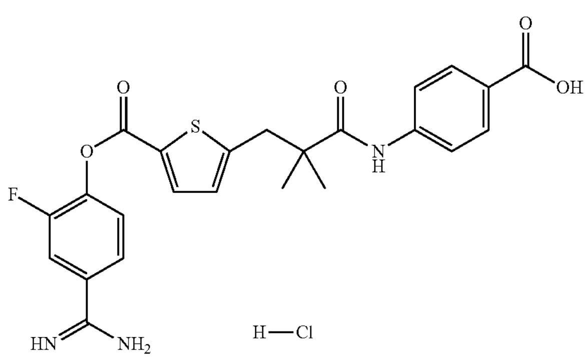 [SMILES: CC(C)(Cc1ccc(C(=O)Oc2ccc(C(=N)N)cc2F)s1)C(=O)Nc1ccc(C(=O)O)cc1 ; Cl] | 1H NMR (400 MHz, DMSO-d6) δ 9.71 (1H, s), 9.39 (2H, br s), 9.06 (2H, br s), 7.99-7.84 (4H, m), 7.84-7.76 (2H, m), 7.76-7.67 (2H, m), 7.07 (1H, d, J = 3.8 Hz), 3.34 (2H, s), 1.30 (6H, s) MS(ESI) m/z 484 (M + H)+ |

TABLE 1-1-continued

| Compound No. | Structure | Analysis data |
|---|---|---|
| 32 | 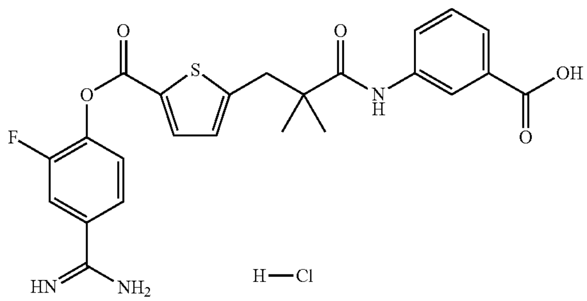 [SMILES: CC(C)(Cc1ccc(C(=O)Oc2ccc(C(=N)N)cc2F)s1)C(=O)Nc1cccc(C(=O)O)c1 ; Cl] | 1H NMR (400 MHz, DMSO-d6) δ 9.64 (1H, s), 9.40 (2H, br s), 9.07 (2H, br s), 8.25 (1H, s), 7.99-7.87 (3H, m), 7.79-7.69 (2H, m), 7.65 (1H, d, J = 7.9 Hz), 7.44 (1H, dd, J = 7.9 Hz), 7.08 (1H, d, J = 3.5 Hz), 3.34 (2H, s), 1.29 (6H, s)<br>MS(ESI) m/z 484 (M + H)+ |
| 33 | 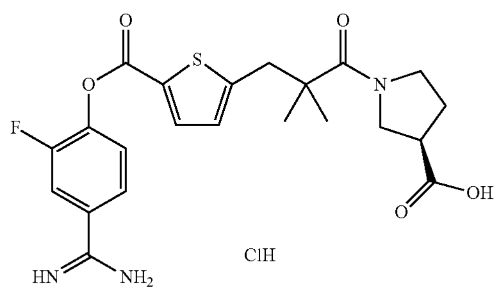 [SMILES: CC(C)(Cc1ccc(C(=O)Oc2ccc(C(=N)N)cc2F)s1)C(=O)N1CC[C@@H](C(=O)O)C1 ; Cl] | 1H NMR (400 MHz, DMSO-d6) δ 12.54 (1H, s), 9.47 (2H, s), 9.21 (2H, s), 7.95 (1H, d, J = 11.5 Hz), 7.92 (1H, d, J = 3.8 Hz), 7.81-7.69 (2H, m), 7.08 (1H, d, J = 3.8 Hz), 3.89-3.33 (4H, m), 3.24-2.91 (3H, m), 2.22-1.87 (2H, m), 1.22 (6H, s)<br>MS(ESI) m/z 462 (M + H)+ |
| 34 | 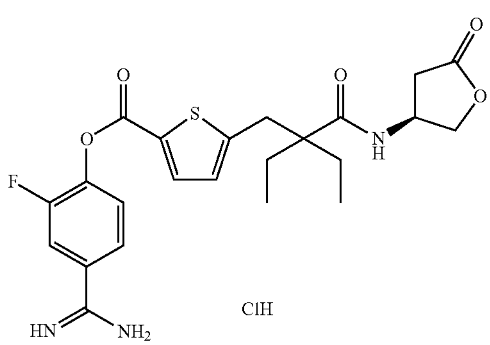 [SMILES: CCC(CC)(Cc1ccc(C(=O)Oc2ccc(C(=N)N)cc2F)s1)C(=O)N[C@@H]1COC(=O)C1 ; Cl] | 1H NMR (400 MHz, DMSO-d6) δ 9.46 (2H, s), 9.18 (2H, s), 8.20 (1H, d, J = 6.0 Hz), 8.00-7.91 (2H, m), 7.78-7.71 (2H, m), 7.06 (1H, d, J = 3.9 Hz), 4.58-4.43 (2H, m), 4.07 (1H, dd, J = 9.1, 3.0 Hz), 3.15 (2H, s), 2.87 (1H, dd, J = 17.7, 8.4 Hz), 2.45 (1H, dd, J = 17.7, 3.6 Hz), 1.64-1.42 (4H, m), 0.86- 0.76 (6H, m)<br>MS(ESI) m/z 476 (M + H)+ |
| 35 | 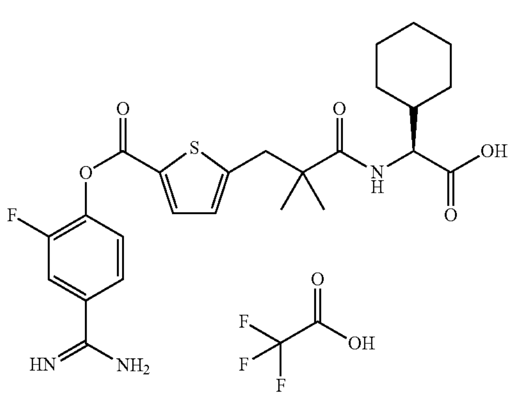 [SMILES: CC(C)(Cc1ccc(C(=O)Oc2ccc(C(=N)N)cc2F)s1)C(=O)N[C@H](C(=O)O)C1CCCCC1 ; O=C(O)C(F)(F)F] | MS(ESI) m/z 504 (M + H)+ |

TABLE 1-1-continued

| Compound No. | Structure | Analysis data |
|---|---|---|
| 36 | 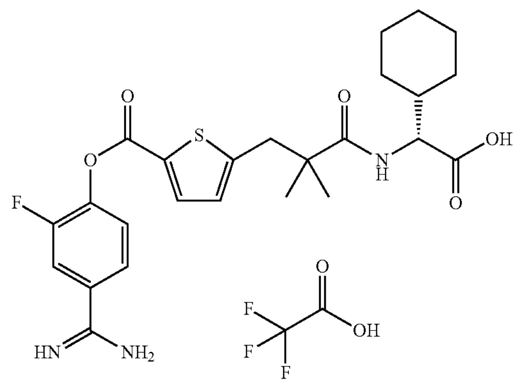 [SMILES: CC(C)(Cc1ccc(C(=O)Oc2ccc(C(=N)N)cc2F)s1)C(=O)N[C@@H](C(=O)O)C1CCCCC1 ; O=C(O)C(F)(F)F] | MS(ESI) m/z 504 (M + H)+ |
| 37 | 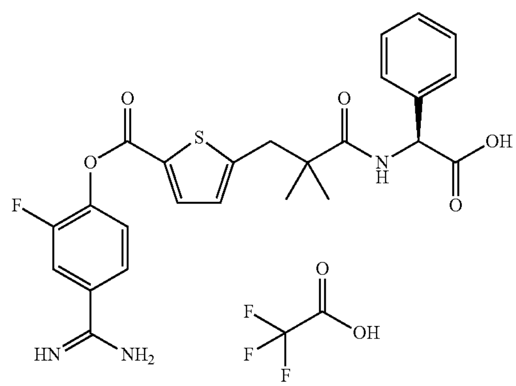 [SMILES: CC(C)(Cc1ccc(C(=O)Oc2ccc(C(=N)N)cc2F)s1)C(=O)N[C@H](C(=O)O)c1ccccc1 ; O=C(O)C(F)(F)F] | MS(ESI) m/z 498 (M + H)+ |
| 38 | 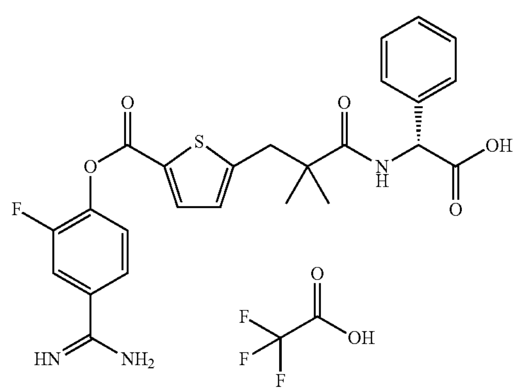 [SMILES: CC(C)(Cc1ccc(C(=O)Oc2ccc(C(=N)N)cc2F)s1)C(=O)N[C@@H](C(=O)O)c1ccccc1 ; O=C(O)C(F)(F)F] | MS(ESI) m/z 498 (M + H)+ |
| 39 | 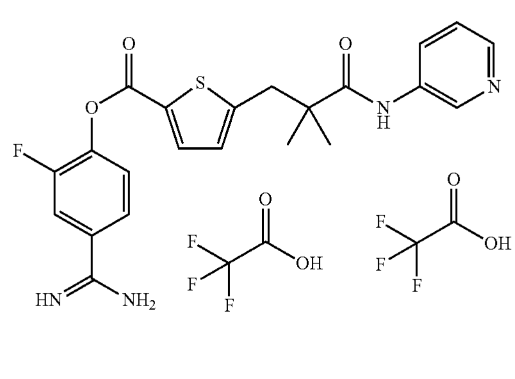 | MS(ESI) m/z 441 (M + H)+ |

TABLE 1-1-continued

| Compound No. | Structure | Analysis data |
|---|---|---|
| 40 | 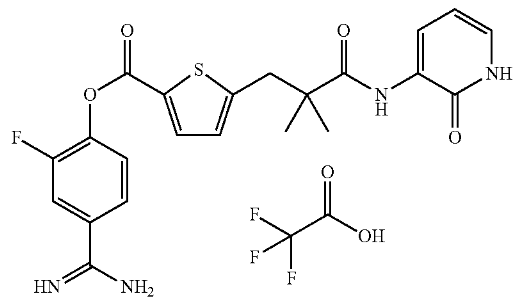 | MS(ESI) m/z 457 (M + H)+ |
| 41 | 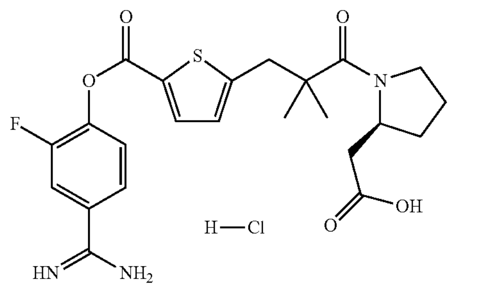 [SMILES: CC(C)(Cc1ccc(C(=O)Oc2ccc(C(=N)N)cc2F)s1)C(=O)N1CCC[C@H]1CC(=O)O ; Cl] | 1H NMR (400 MHz, DMSO-d6) δ 12.17 (1H, br s), 9.67-9.09 (4H, m), 8.00-7.89 (2H, m), 7.81-7.70 (2H, m), 7.08 (1H, d, J = 3.8 Hz). 4.33-4.21 (1H, m), 3.68-3.50 (2H, m), 3.27-3.09 (2H, m), 2.83-2.71 (1H, m), 2.26-2.12 (1H, m), 2.00-1.76 (3H, m), 1.67-1.54 (1H, m), 1.22 (6H, d, J = 7.2 Hz)<br>MS(ESI) m/z 476 (M + H)+ |
| 42 | 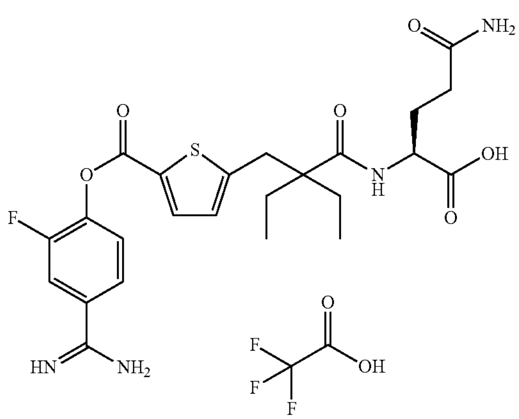 [SMILES: CCC(CC)(Cc1ccc(C(=O)Oc2ccc(C(=N)N)cc2F)s1)C(=O)N[C@@H](CCC(N)=O)C(=O)O ; O=C(O)C(F)(F)F] | 1H NMR (400 MHz, DMSO-d6) δ 12.17 (1H, br s), 9.67-9.09 (4H, m), 8.00-7.89 (2H, m), 7.81-7.70 (2H, m), 7.08 (1H, d, J = 3.8 Hz), 4.33-4.21 (1H, m), 3.68-3.50 (2H, m), 3.27-3.09 (2H, m), 2.83-2.71 (1H, m), 2.26-2.12 (1H, m), 2.00-1.76 (3H, m), 1.67-1.54 (1H, m), 1.22 (6H, d, J = 7.2 Hz)<br>MS(ESI) m/z 521 (M + H)+ |
| 43 | 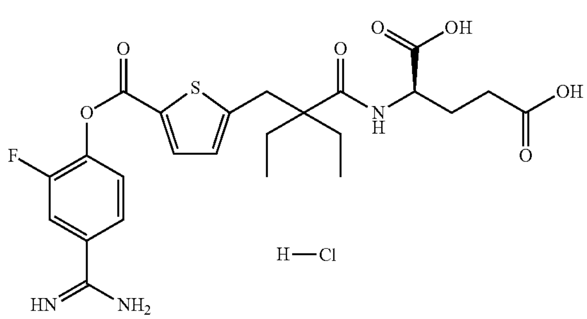 [SMILES: CCC(CC)(Cc1ccc(C(=O)Oc2ccc(C(=N)N)cc2F)s1)C(=O)N[C@H](CCC(=O)O)C(=O)O ; Cl] | 1H NMR (400 MHz, DMSO-d6) δ 12.36 (2H, br s), 9.46 (2H, s), 9.23 (2H, s), 7.98-7.91 (2H, m), 7.85 (1H, d, J = 7.5 Hz), 7.79-7.72 (2H, m), 7.08 (1H, d, J = 3.9 Hz), 4.29-4.20 (1H, m), 3.15 (2H, s), 2.27 (2H, t, J = 7.6 Hz), 2.09-1.80 (2H, m), 1.60-1.47 (4H, m), 0.89-0.78 (6H, m)<br>MS(ESI) m/z 522 (M + H)+ |

TABLE 1-1-continued
| Compound No. | Structure | Analysis data |
|---|---|---|
| 44 | 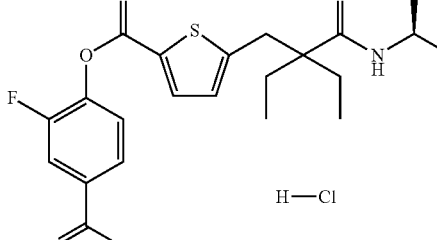 | 1H NMR (400 MHz, DMSO-d6) δ 12.54 (1H, s), 9.47 (2H, s), 9.21 (2H, s), 7.98-7.89 (3H, m), 7.80-7.73 (2H, m), 7.38 (1H, s), 7.09 (1H, d, J = 3.9 Hz), 6.92 (1H, s), 4.59 (1H, dd, J = 13.2, 7.4 Hz), 3.13 (2H, s), 2.64-2.52 (2H, m), 1.57-1.44 (4H, m), 0.89-0.75 (6H, m) MS(ESI) m/z 507 (M + H)+ |
| 45 | 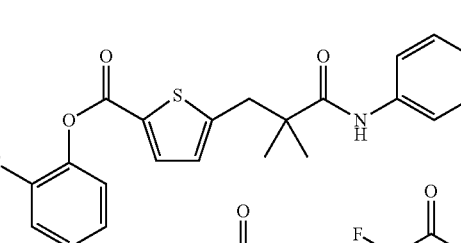 | MS(ESI) m/z 471 (M + H)+ |
| 46 | 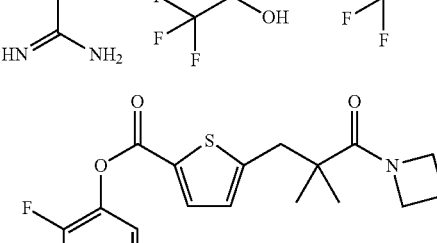 | MS(ESI) m/z 440 (M + H)+ |
| 47 | 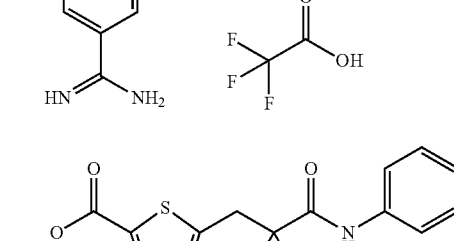 | MS(ESI) m/z 500 (M + H)+ |
| 48 | 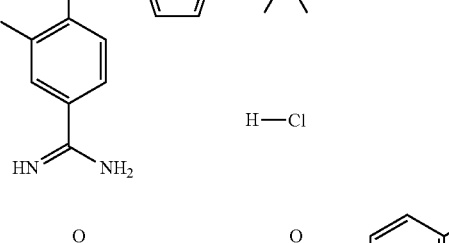 | 1H NMR (400 MHz, DMSO-d6) δ 12.35 (1H, s), 9.50-9.17 (4H, m), 8.03-7.96 (2H, m), 7.83-7.77 (2H, m), 7.60 (2H, d, J = 8.0 Hz), 7.25 (2H, d, J = 8.0 Hz), 7.14 (1H, d, J = 8.0), 3.57 (2H, s), 3.34 (2H, s), 1.79-1.65 (4H, m), 0.92 (6H, t, J = 8.0 Hz). MS(ESI) m/z 526 (M + H)+ |

TABLE 1-1-continued

| Compound No. | Structure | Analysis data |
|---|---|---|
| 49 | 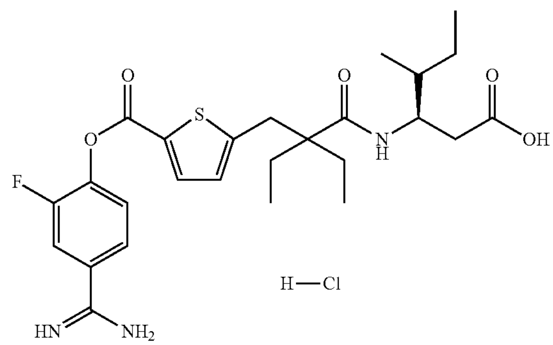 [SMILES: CCC(C)[C@@H](CC(=O)O)NC(=O)C(CC)(CC)Cc1ccc(C(=O)Oc2ccc(C(=N)N)cc2F)s1 ; Cl] | 1H NMR (400 MHz, DMSO-d6) δ 12.09 (1H, s), 9.44 (2H, s), 9.17 (2H, s), 7.98-7.91 (2H, m), 7.78-7.72 (2H, m), 7.37 (1H, d, J = 8.2 Hz), 7.06 (1H, d, J = 3.8 Hz), 4.19-4.09 (1H, m), 3.17-3.06 (2H, m), 2.43-2.30 (2H, m), 1.63-1.44 (4H, m), 1.40-1.27 (1H, m), 1.11-0.98 (1H, m), 0.89-0.73 (10H, m) MS(ESI) m/z 520 (M + H)+ |
| 50 | 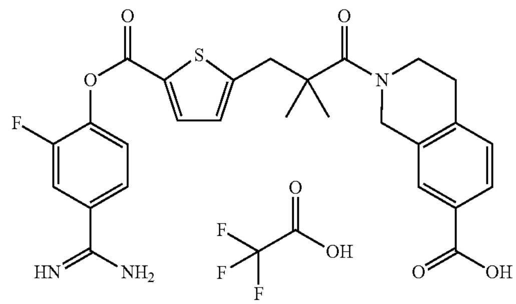 [SMILES: CC(C)(Cc1ccc(C(=O)Oc2ccc(C(=N)N)cc2F)s1)C(=O)N1CCc2ccc(C(=O)O)cc2C1 ; O=C(O)C(F)(F)F] | 1H NMR (400 MHz, DMSO-d6) δ 12.86 (1H, br s), 9.41 (2H, s), 9.14 (2H, s), 7.96-7.85 (3H, m), 7.77-7.70 (3H, m), 7.29 (1H, d, J = 8.0 Hz), 7.07 (1H, d, J = 3.8 Hz), 4.82 (2H, s), 3.89-3.80 (2H, m), 2.93-2.85 (2H, m), 1.30 (6H, s), 1.04 (2H, d, J = 6.1 Hz) MS(ESI) m/z 524 (M + H)+ |
| 51 | 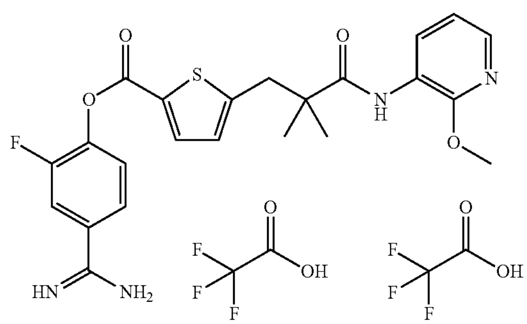 | MS(ESI) m/z 471 (M + H)+ |
| 52 | 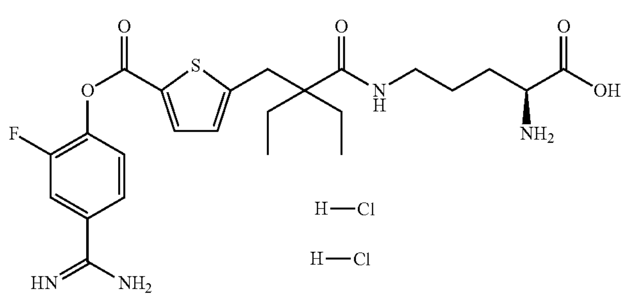 | 1H NMR (400 MHz, DMSO-d6) δ 9.45 (2H, br s), 9.30 (2H, br s), 8.00-7.91 (2H, m), 7.91-7.82 (1H, m), 7.82-7.69 (2H, m), 7.04 (1H, d, J = 3.9 Hz), 3.83-3.64 (1H, m), 3.19-3.04 (4H, m), 1.86-1.64 (2H, m), 1.64-1.37 (4H, m), 0.80 (6H, t, J = 7.4 Hz) MS(ESI) m/z 507 (M + H)+ |
| 53 | 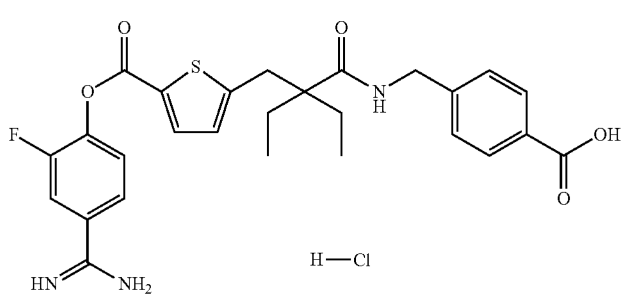 [SMILES: CCC(CC)(Cc1ccc(C(=O)Oc2ccc(C(=N)N)cc2F)s1)C(=O)NCc1ccc(C(=O)O)cc1 ; Cl] | MS(ESI) m/z 526 (M + H)+ |

TABLE 1-1-continued

| Compound No. | Structure | Analysis data |
|---|---|---|
| 54 | 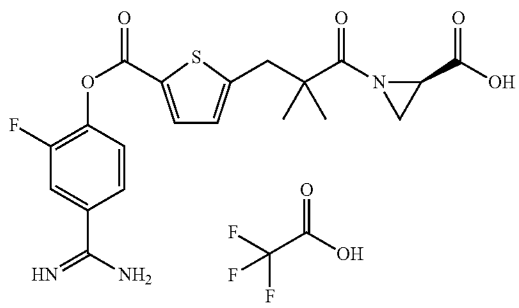 [SMILES: CC(C)(Cc1ccc(C(=O)Oc2ccc(C(=N)N)cc2F)s1)C(=O)N1C[C@@H]1C(=O)O ; O=C(O)C(F)(F)F] | MS(ESI) m/z 434 (M + H)+ |
| 55 | 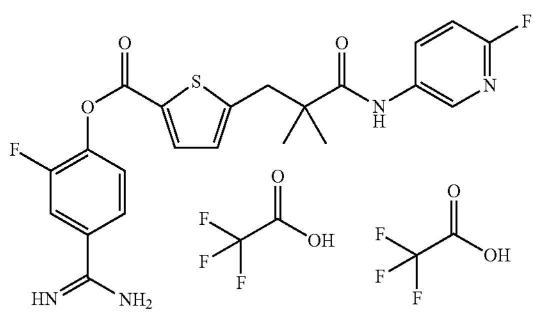 | MS(ESI) m/z 471 (M + H)+ |
| 56 | 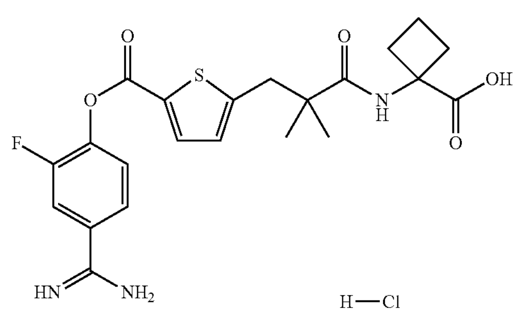 [SMILES: CC(C)(Cc1ccc(C(=O)Oc2ccc(C(=N)N)cc2F)s1)C(=O)NC1(C(=O)O)CCC1 ; Cl] | 1H NMR (400 MHz, DMSO-d6) δ 9.31 (4H, br s), 8.09 (1H, s), 7.97-7.89 (2H, m), 7.79-7.70 (2H, m), 7.08 (1H, d, J = 3.9 Hz), 3.14 (2H, s), 2.30-2.14 (2H, m), 1.88 (4H, dd, J = 14.5, 6.8 Hz), 1.15 (6H, s)<br>MS(ESI) m/z 462 (M + H)+ |
| 57 | 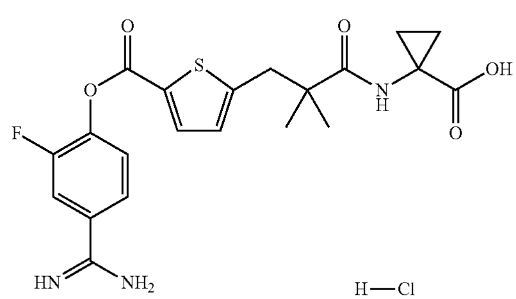 [SMILES: CC(C)(Cc1ccc(C(=O)Oc2ccc(C(=N)N)cc2F)s1)C(=O)NC1(C(=O)O)CC1 ; Cl] | MS(ESI) m/z 448 (M + H)+ |

TABLE 1-1-continued
| Compound No. | Structure | Analysis data |
|---|---|---|
| 58 | 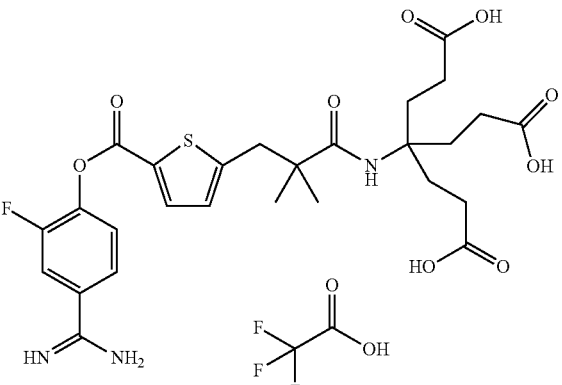 | MS(ESI) m/z 594 (M + H)+ |
| 59 | 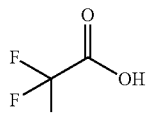 | MS(ESI) m/z 528 (M + H)+ |
| 60 | 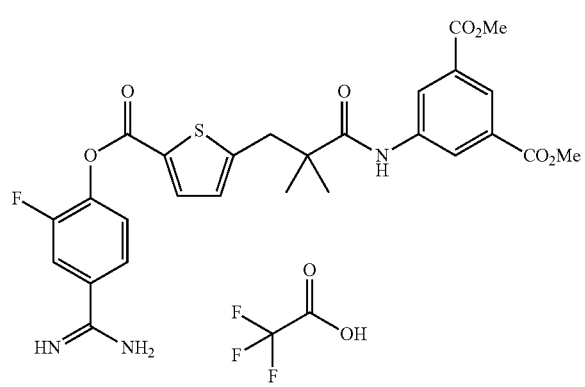 [SMILES: COC(=O)c1cc(NC(=O)C(C)(C)Cc2ccc(C(=O)Oc3ccc(C(=N)N)cc3F)s2)cc(C(=O)OC)c1 ; O=C(O)C(F)(F)F] | MS(ESI) m/z 542 (M + H)+ |
| 61 | 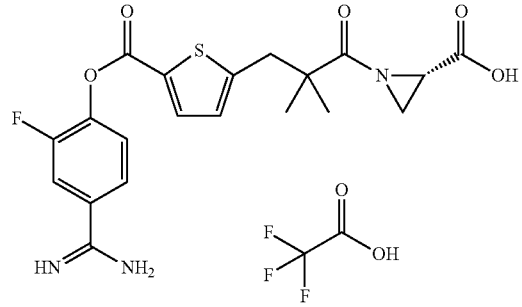 [SMILES: CC(C)(Cc1ccc(C(=O)Oc2ccc(C(=N)N)cc2F)s1)C(=O)N1C[C@H]1C(=O)O ; O=C(O)C(F)(F)F] | MS(ESI) m/z 434 (M + H)+ |

TABLE 1-1-continued

| Compound No. | Structure | Analysis data |
| --- | --- | --- |
| 62 | 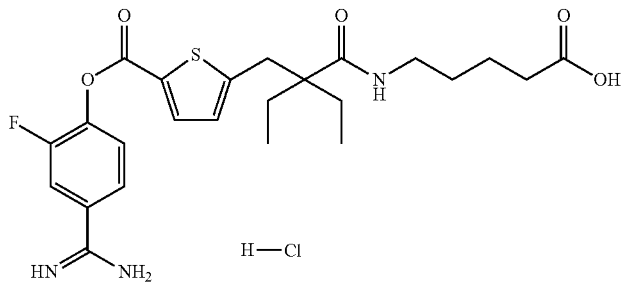 [SMILES: CCC(CC)(Cc1ccc(C(=O)Oc2ccc(C(=N)N)cc2F)s1)C(=O)NCCCCC(=O)O ; Cl] | 1H NMR (400 MHz, DMSO-d6) δ 11.98 (1H, br s), 9.44 (2H, s), 9.18 (2H, s), 7.95-7.92 (2H, m), 7.78-7.69 (m, 3H), 7.04 (1H, d, J = 3.9 Hz), 3.12-3.08 (4H, m), 2.20 (2H, t, J = 6.6 Hz), 1.59-1.40 (8H, m), 0.79 (6H, t, J = 7.4 Hz). MS(ESI) m/z 492 (M + H)+ |
| 63 | 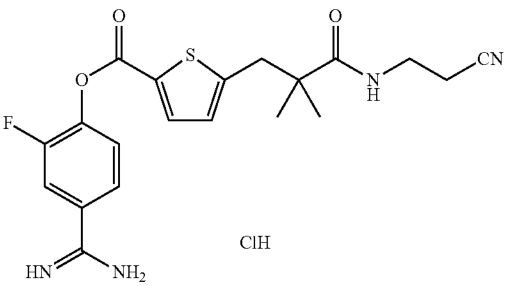 [SMILES: CC(C)(Cc1ccc(C(=O)Oc2ccc(C(=N)N)cc2F)s1)C(=O)NCCC#N ; Cl] | MS(ESI) m/z 417 (M + H)+ |
| 64 | 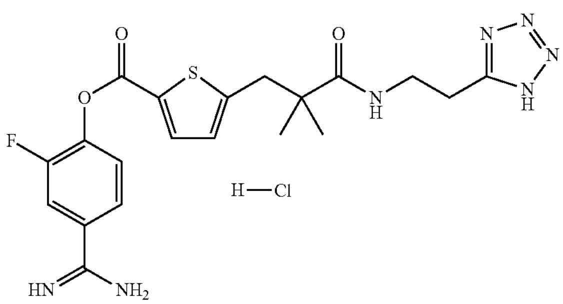 | 1H NMR (400 MHz, DMSO-d6) δ 9.47 (2H, s), 9.21 (2H, s), 7.98-7.86 (3H, m), 7.79-7.73 (2H, m), 6.99 (1H, d, J = 3.8 Hz), 3.46 (2H, dd, J = 12.8, 7.1 Hz), 3.09 (2H, s), 3.05 (2H, t, J = 7.1 Hz), 1.10 (6H, s) MS(ESI) m/z 460 (M + H)+ |
| 65 | 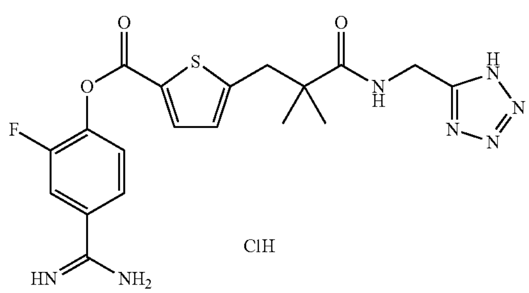 [SMILES: CC(C)(Cc1ccc(C(=O)Oc2ccc(C(=N)N)cc2F)s1)C(=O)NCc1nnn[nH]1 ; Cl] | 1H NMR (400 MHz, DMSO-d6) δ 9.45 (2H, s), 9.22 (2H, s), 8.50 (1H, t, J = 5.5 Hz), 7.98-7.92 (1H, m), 7.89 (1H, d, J = 3.8 Hz), 7.79-7.73 (2H, m), 6.99 (1H, d, J = 3.8 Hz), 4.54 (2H, d, J = 5.6 Hz), 3.13 (2H, s), 1.17 (6H, s) MS(ESI) m/z 446 (M + H)+ |
| 66 | 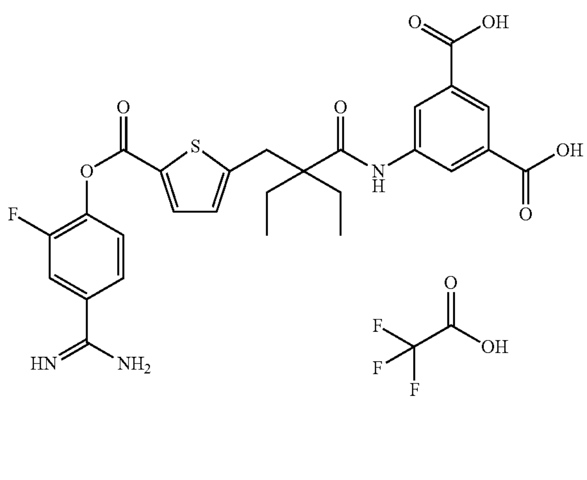 [SMILES: CCC(CC)(Cc1ccc(C(=O)Oc2ccc(C(=N)N)cc2F)s1)C(=O)Nc1cc(C(=O)O)cc(C(=O)O)c1 ; O=C(O)C(F)(F)F] | 1H NMR (400 MHz, DMSO-d6) δ 9.87 (1H, br s), 9.40 (2H, br s), 9.29 (2H, s), 8.54 (2H, d, J = 2.0 Hz), 8.19 (1H, t, J = 2.0 Hz), 7.96 (1H, d, J = 4.0 Hz), 7.94-7.92 (1H, m), 7.91-7.89 (1H, m), 7.75-7.72 (2H, m), 7.09 (1H, d, J = 4.0 Hz), 1.83-1.51 (4H, m), 0.87 (6H, t, J = 7.0 Hz) MS(ESI) m/z 556 (M + H)+ |

TABLE 1-1-continued
| Compound No. | Structure | Analysis data |
|---|---|---|
| 67 | 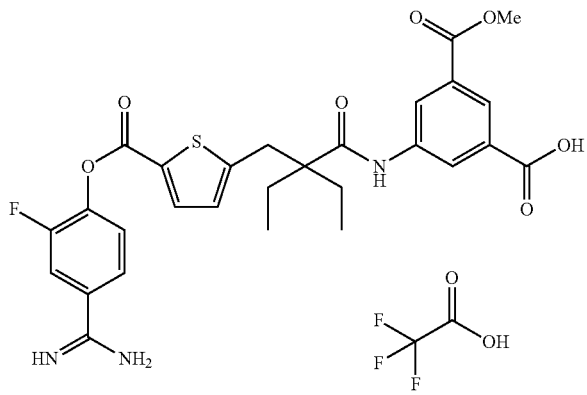 [SMILES: CCC(CC)(Cc1ccc(C(=O)Oc2ccc(C(=N)N)cc2F)s1)C(=O)Nc1cc(C(=O)O)cc(C(=O)OC)c1 ; O=C(O)C(F)(F)F] | MS(ESI) m/z 570 (M + H)+ |
| 68 | 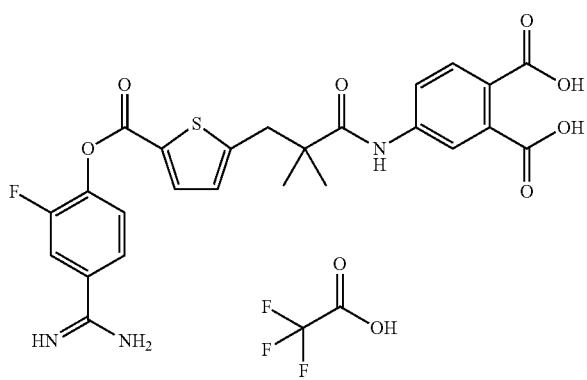 [SMILES: CC(C)(Cc1ccc(C(=O)Oc2ccc(C(=N)N)cc2F)s1)C(=O)Nc1ccc(C(=O)O)c(C(=O)O)c1 ; O=C(O)C(F)(F)F] | MS(ESI) m/z 528 (M + H)+ |
| 69 | 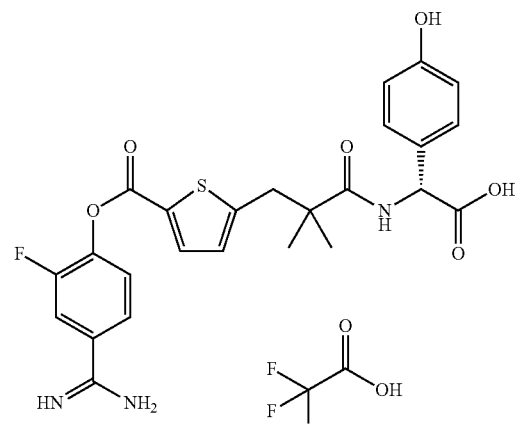 | 1H NMR (400 MHz, DMSO-d6) δ 9.47-9.30 (4H, br), 7.95-7.78 (2H, m), 7.71-7.63 (2H, m), 7.10 (2H, d, J = 9.0 Hz), 6.93 (1H, d, J = 4.0 Hz), 6.64 (2H, d, J = 9.0 Hz), 5.11 (1H, s), 3.09 (3H, d, J = 2.0 Hz), 1.11 (6H, d, J = 6.0 Hz)<br>MS(ESI) m/z 514 (M + H)+ |

TABLE 1-1-continued

| Compound No. | Structure | Analysis data |
|---|---|---|
| 70 | 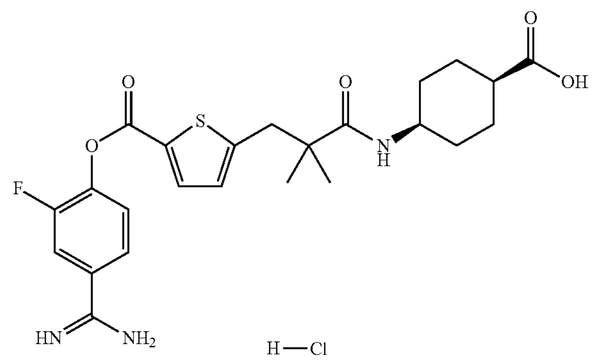 [SMILES: CC(C)(Cc1ccc(C(=O)Oc2ccc(C(=N)N)cc2F)s1)C(=O)N[C@H]1CC[C@@H](C(=O)O)CC1 ; Cl] | MS(ESI) m/z 490 (M + H)+ |
| 71 | 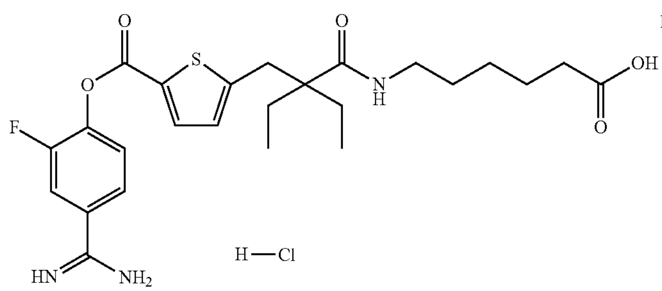 [SMILES: CCC(CC)(Cc1ccc(C(=O)Oc2ccc(C(=N)N)cc2F)s1)C(=O)NCCCCCC(=O)O ; Cl] | MS(ESI) m/z 506 (M + H)+ |
| 72 | 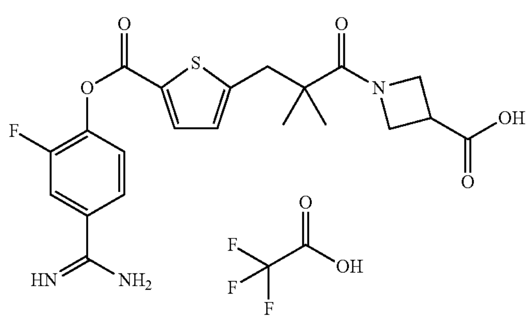 [SMILES: CC(C)(Cc1ccc(C(=O)Oc2ccc(C(=N)N)cc2F)s1)C(=O)N1CC(C(=O)O)C1 ; O=C(O)C(F)(F)F] | 1H NMR (400 MHz, DMSO-d6) δ 9.41 (2H, s), 9.17 (2H, s), 7.98-7.89 (2H, m), 7.81-7.70 (2H, m), 7.08 (1H, d, J = 4.0 Hz), 4.64-4.18 (2H, m), 4.11-3.79 (2H, m), 3.10 (2H, s), 1.15 (6H, s)<br>MS(ESI) m/z 448 (M + H)+ |
| 73 | 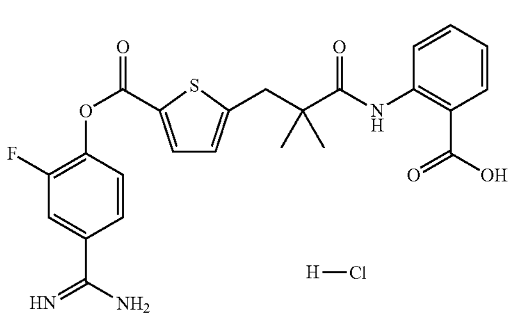 [SMILES: CC(C)(Cc1ccc(C(=O)Oc2ccc(C(=N)N)cc2F)s1)C(=O)Nc1ccccc1C(=O)O ; Cl] | MS(ESI) m/z 484 (M + H)+ |

TABLE 1-1-continued

| Compound No. | Structure | Analysis data |
|---|---|---|
| 74 | 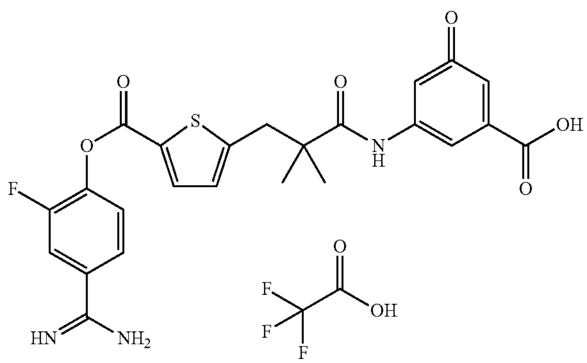 | MS(ESI) m/z 500 (M + H)+ |
| 75 | 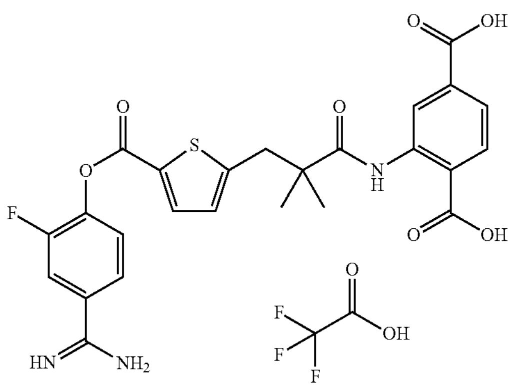 [SMILES: CC(C)(Cc1ccc(C(=O)Oc2ccc(C(=N)N)cc2F)s1)C(=O)Nc1cc(C(=O)O)ccc1C(=O)O ; O=C(O)C(F)(F)F] | MS(ESI) m/z 528 (M + H)+ |
| 76 | 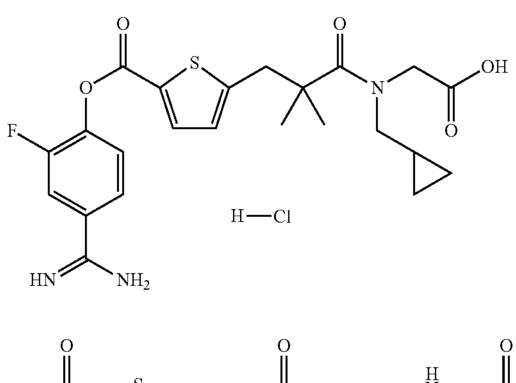 | MS(ESI) m/z 476 (M + H)+ |
| 77 | 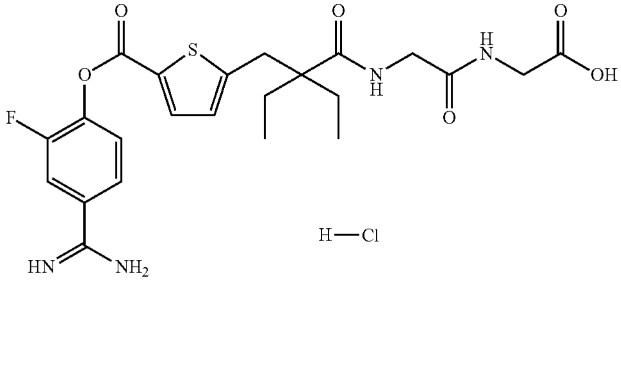 [SMILES: CCC(CC)(Cc1ccc(C(=O)Oc2ccc(C(=N)N)cc2F)s1)C(=O)NCC(=O)NCC(=O)O ; Cl] | MS(ESI) m/z 507 (M + H)+ |

TABLE 1-1-continued

| Compound No. | Structure | Analysis data |
|---|---|---|
| 78 | 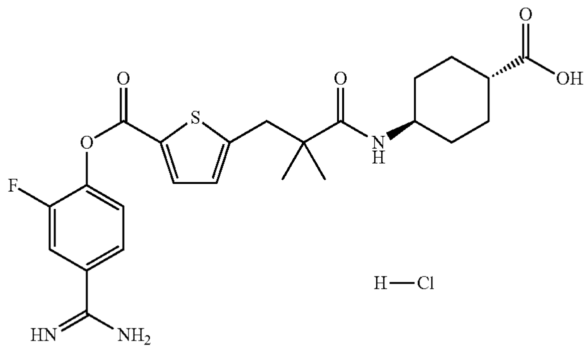 [SMILES: CC(C)(Cc1ccc(C(=O)Oc2ccc(C(=N)N)cc2F)s1)C(=O)N[C@H]1CC[C@H](C(=O)O)CC1 ; Cl] | MS(ESI) m/z 490 (M + H)+ |
| 79 | 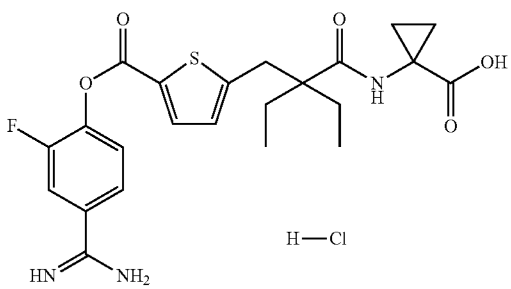 [SMILES: CCC(CC)(Cc1ccc(C(=O)Oc2ccc(C(=N)N)cc2F)s1)C(=O)NC1(C(=O)O)CC1 ; Cl] | MS(ESI) m/z 476 (M + H)+ |
| 80 | 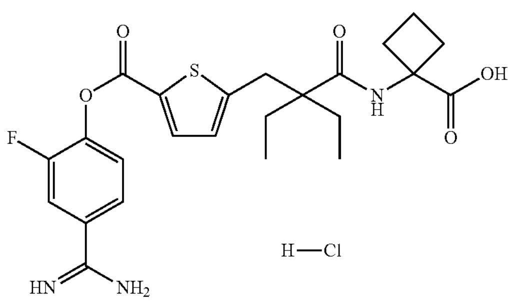 [SMILES: CCC(CC)(Cc1ccc(C(=O)Oc2ccc(C(=N)N)cc2F)s1)C(=O)NC1(C(=O)O)CCC1 ; Cl] | MS(ESI) m/z 490 (M + H)+ |
| 81 | 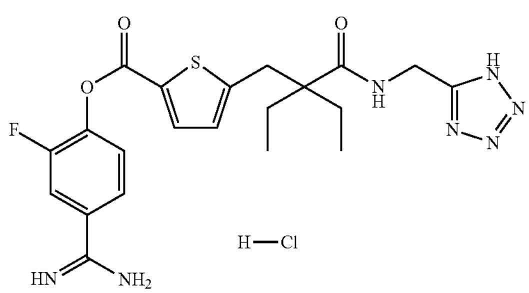 [SMILES: CCC(CC)(Cc1ccc(C(=O)Oc2ccc(C(=N)N)cc2F)s1)C(=O)NCc1nnn[nH]1 ; Cl] | 1H NMR (400 MHz, DMSO-d6) δ 9.47 (1H, s), 9.21 (1H, s), 8.57 (1H, s), 7.95 (1H, d, J = 11.6 Hz), 7.89 (1H, d, J = 3.8 Hz), 7.80-7.72 (1H, m), 7.00 (1H, d, J = 3.8 Hz), 7.00 (1H, d, J = 3.8 Hz), 4.55 (1H, d, J = 5.5 Hz), 3.14 (1H, s), 1.62-1.42 (1H, m), 0.78 (1H, t, J = 7.4 Hz) MS(ESI) m/z 474 (M + H)+ |
| 82 | 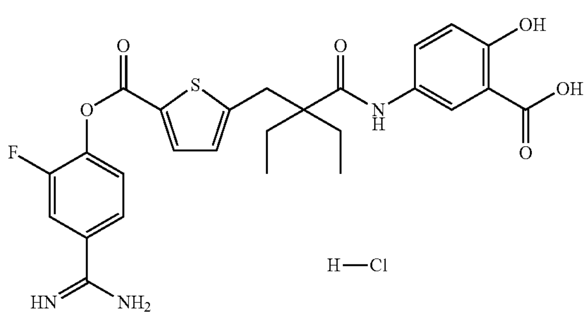 [SMILES: CCC(CC)(Cc1ccc(C(=O)Oc2ccc(C(=N)N)cc2F)s1)C(=O)Nc1ccc(O)c(C(=O)O)c1 ; Cl] | MS(ESI) m/z 528 (M + H)+ |

TABLE 1-1-continued

| Compound No. | Structure | Analysis data |
|---|---|---|
| 83 | 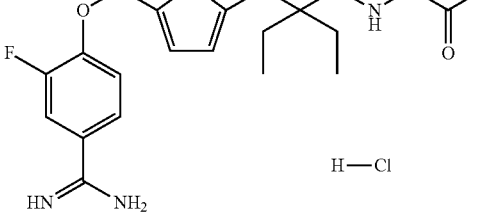 | MS(ESI) m/z 450 (M + H)+ |
| 84 | 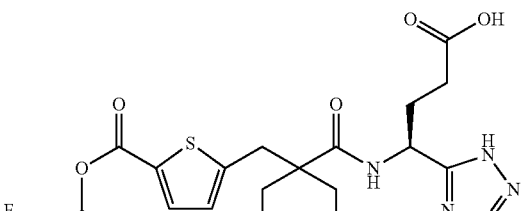 | 1H NMR (400 MHz, DMSO-d6) δ 9.46 (2H, s), 9.18 (2H, s), 8.27 (1H, d, J = 7.6 Hz), 7.97-7.92 (1H, m), 7.87 (1H, d, J = 3.8 Hz), 7.79-7.73 (2H, m), 6.98 (1H, d, J = 3.8 Hz), 5.29 (1H, dd, J = 14.4, 8.1 Hz), 3.20-3.09 (2H, m), 2.36-2.06 (4H, m), 1.61-1.48 (4H, m), 0.77 (6H, dt, J = 20.1, 7.4 Hz) MS(ESI) m/z 546 (M + H)+ |
| 85 | 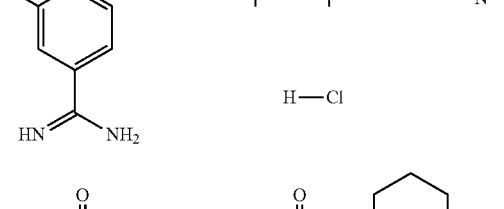 | MS(ESI) m/z 490 (M + H)+ |
| 86 | 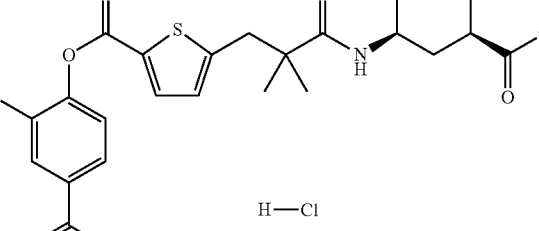 | 1H NMR (400 MHz, DMSO-d6) δ 9.41 (2H, s), 9.16 (2H, s), 8.11 (1H, d, J = 8.1 Hz), 7.96-7.85 (2H, m), 7.81-7.70 (2H, m), 6.98 (1H, d, J = 3.9 Hz), 4.88-4.78 (1H, m), 3.46-3.26 (2H, m), 3.08 (2H, s), 1.55-1.33 (4H, m), 0.75 (3H, t, J = 7.4 Hz), 0.65 (3H, t, J = 7.4 Hz) MS(ESI) m/z 532 (M + H)+ |

Experimental Example 1

Measurement of Trypsin Inhibitory Activity

Using a 96 well plate (#3915, Costar), a test compound (25 μL) was mixed with 20 μM fluorescence enzyme substrate (Boc-Phe-Ser-Arg-AMC, 50 μL) mixed with 200 mM Tris-HCl buffer (pH 8.0), and human trypsin (Sigma, 25 μL) was added. Using a fluorescence plate reader fmax (Molecular Devices, Inc.), the reaction rate was measured from the time-course changes at excitation wavelength 355 nm and fluorescence wavelength 460 nm. The Ki value was calculated from the concentration of the test compound, reciprocal of reaction rate, and Km value of the enzyme substrate, and by using Dixon plot. The results are shown in Table 2.

Experimental Example 2

Measurement of Enteropeptidase Inhibitory Activity

Using a 96 well plate (#3915, Costar), a test compound (25 μL), 400 mM Tris-HCl buffer (pH 8.0, 25 μL) and 0.5 mg/mL fluorescence enzyme substrate (Gly-Asp-Asp-Asp-Asp-Lys-β-Naphtylamide, 25 μL) were mixed, and recombinant human enteropeptidase (R&D Systems, Inc., 25 μL) was added. Using a fluorescence plate reader fmax (Molecular Devices, Inc.), the reaction rate was measured from the time-course changes at excitation wavelength 320 nm and fluorescence wavelength 405 nm. The Ki value was calculated from the concentration of the test compound, reciprocal of reaction rate, and Km value of the enzyme substrate, and by using Dixon plot. The results are shown in Table 2.

TABLE 2

| Compound No. | Enteropeptidase inhibitory activity Ki (nM) | Trypsin inhibitory activity Ki (nM) |
| --- | --- | --- |
| 1 | 0.14 | 0.61 |
| 2 | 0.73 | 4.10 |
| 3 | 0.29 | 0.42 |
| 4 | 0.46 | 0.75 |
| 5 | 0.24 | 0.50 |
| 6 | 0.69 | 0.95 |
| 7 | 0.41 | 1.33 |
| 8 | 0.87 | 1.69 |
| 9 | 0.79 | 2.02 |
| 10 | 0.49 | 1.50 |
| 11 | 0.41 | 1.87 |
| 12 | 0.94 | 1.78 |
| 13 | 1.56 | 5.18 |
| 14 | 0.99 | 2.50 |
| 15 | 0.84 | 1.74 |
| 16 | 1.10 | 8.30 |
| 17 | 1.69 | 6.38 |
| 18 | 1.24 | 2.49 |
| 19 | 0.33 | 0.82 |
| 20 | 2.61 | 7.91 |
| 21 | 0.88 | 1.76 |
| 22 | 1.00 | 3.57 |
| 23 | 1.81 | 3.17 |
| 24 | 0.27 | 2.01 |
| 25 | 0.26 | 1.04 |
| 26 | 1.33 | 3.10 |
| 27 | 0.73 | 1.67 |
| 28 | 0.65 | 1.93 |
| 29 | 1.18 | 3.84 |
| 30 | 0.94 | 2.73 |
| 31 | 1.08 | 2.89 |
| 32 | 1.43 | 0.70 |
| 33 | 1.02 | 2.00 |
| 34 | 2.56 | 2.73 |
| 35 | 2.56 | 3.04 |
| 36 | 4.70 | 3.07 |
| 37 | 0.96 | 1.51 |
| 38 | 0.97 | 1.45 |
| 39 | 7.56 | 3.60 |
| 40 | 6.66 | 4.54 |
| 41 | 1.58 | 3.88 |
| 42 | 1.69 | 3.88 |
| 43 | 0.42 | 1.96 |
| 44 | 0.67 | 1.69 |
| 45 | 4.13 | 3.36 |
| 46 | 5.27 | 3.89 |
| 47 | 0.53 | 0.92 |
| 48 | 2.41 | 3.35 |
| 49 | 3.26 | 1.97 |
| 50 | 3.46 | 3.49 |
| 51 | 3.75 | 1.87 |
| 52 | 5.53 | 5.78 |
| 53 | 2.69 | 9.27 |
| 54 | 1.76 | 1.53 |
| 55 | 2.51 | 3.30 |
| 56 | 0.51 | 1.49 |
| 57 | 0.67 | 1.01 |
| 58 | 0.71 | 1.59 |
| 59 | 0.31 | 0.49 |
| 60 | 1.22 | 1.02 |
| 61 | 1.13 | 0.96 |
| 62 | 0.98 | 5.17 |
| 63 | 2.90 | 3.65 |
| 64 | 0.53 | 1.60 |
| 65 | 0.53 | 0.75 |
| 66 | 0.71 | 1.58 |
| 67 | 3.73 | 4.40 |
| 68 | 0.24 | 0.21 |
| 69 | 0.72 | 1.14 |
| 70 | 1.11 | 1.70 |
| 71 | 4.97 | 8.01 |
| 72 | 0.63 | 1.85 |
| 73 | 2.41 | 3.65 |
| 74 | 0.58 | 0.18 |
| 75 | 0.39 | 3.72 |
| 76 | 0.67 | 2.01 |
| 77 | 0.69 | 1.42 |
| 78 | 1.53 | 2.57 |
| 79 | 1.12 | 2.19 |
| 80 | 1.33 | 4.67 |
| 81 | 1.20 | 3.54 |

Thus, the compound of the present invention was confirmed to show superior enteropeptidase inhibitory activity and superior trypsin inhibitory activity. Therefore, it has been shown that the compound of the present invention having an inhibitory activity on enteropeptidase and trypsin decreases digestive capacity for protein, lipid, and carbohydrates, and is effective as a therapeutic and prophylactic drug for obesity and hyperlipidemia.

Experimental Example 3

Evaluation of Anti-Diabetic Action

Anti-diabetic action of the compound or its pharmaceutical salt thereof of the present invention can be confirmed by, for example, the following procedure: KK-A$^y$/JCL mice (male, 5- to 7-week-old, CLEA Japan, Inc.) known to spontaneously develop obese type 2 diabetes are purchased and, after one week of preliminary rearing period, grouped (6 per group) with the body weight and non-fasting blood glucose levels as indices. The animals are individually housed in a polycarbonate cage and allowed to drink water freely from a watering bottle. During the test period, they are allowed to freely ingest a mixture of a test compound, which may be in salt form thereof (5.6 mg/100 g or 16.8 mg/100 g, for example) and powder feed CRF-1 (Oriental Yeast Co., Ltd.). CRF-1 alone is given to the control group. After one week of dosing period, blood (6 μL) is drawn from the tail vein of the animals, and the blood glucose level is measured by ACCU-CHEK Aviva (Roche Diagnostics K.K.).

Thus, the test compound can be confirmed to show a significant hypoglycemic action. The compound of the present invention having an enteropeptidase inhibitory activity and a trypsin inhibitory activity is shown to have a blood glucose elevation suppressing or hypoglycemic action. In addition, it has also been shown that the compound of the present invention shows an insulin sensitizing activity and is also useful as a prophylactic or therapeutic agent for obesity, diabetic complications, or metabolic syndrome, since it shows a blood glucose elevation suppressing or hypoglycemic action.

Industrial Applicability

The trypsin and enteropeptidase inhibitory compound relating to the present invention can be used as an active ingredient of a therapeutic or prophylactic drug of diabetes or diabetic complications.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. 3-[5-(4-amidino-2-fluorophenoxycarbonyl)thiophen-2-yl]-2,2-dimethylpropanoic acid:

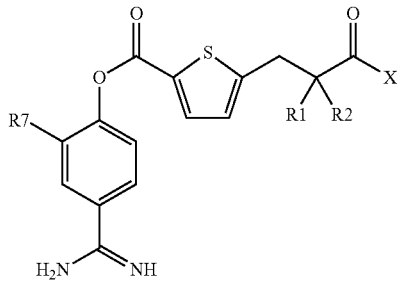

or a pharmaceutically acceptable salt thereof.

2. A pharmaceutical composition, comprising a compound or a pharmaceutically acceptable salt thereof according to claim 1 and at least one pharmaceutically acceptable carrier or excipient.

3. N-[3-{5-(4-amidino-2-fluorophenoxycarbonyl)thiophen-2-yl}-2,2-dimethylpropanoyl]glycine:

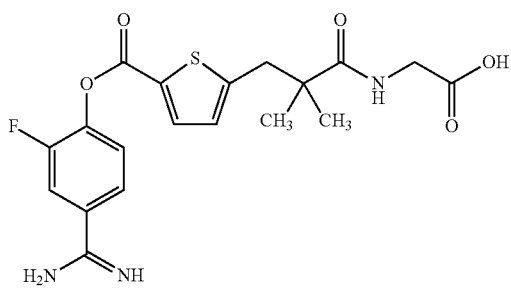 [SMILES: CC(C)(Cc1ccc(C(=O)Oc2ccc(C(=N)N)cc2F)s1)C(=O)NCC(=O)O]

or a pharmaceutically acceptable salt thereof.

4. A pharmaceutical composition, comprising a compound or a pharmaceutically acceptable salt thereof according to claim 3 and at least one pharmaceutically acceptable carrier or excipient.

5. N-[3-{5-(4-amidino-2-fluorophenoxycarbonyl)thiophen-2-yl}-2,2-Dimethylpropanoyl]-L-serine:

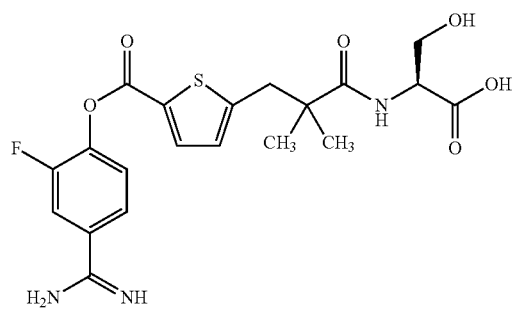 [SMILES: CC(C)(Cc1ccc(C(=O)Oc2ccc(C(=N)N)cc2F)s1)C(=O)N[C@@H](CO)C(=O)O]

or a pharmaceutically acceptable salt thereof.

6. A pharmaceutical composition, comprising a compound or a pharmaceutically acceptable salt thereof according to claim 5 and at least one pharmaceutically acceptable carrier or excipient.

7. N-allyl-N-[3-{5-(4-amidino-2-fluorophenoxycarbonyl)thiophen-2-yl}-2,2-dimethylpropanoyl]glycine:

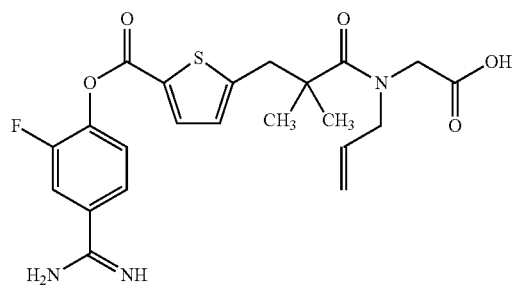 [SMILES: C=CCN(CC(=O)O)C(=O)C(C)(C)Cc1ccc(C(=O)Oc2ccc(C(=N)N)cc2F)s1]

or a pharmaceutically acceptable salt thereof.

8. A pharmaceutical composition, comprising a compound or a pharmaceutically acceptable salt thereof according to claim 7 and at least one pharmaceutically acceptable carrier or excipient.

* * * * *

UNITED STATES PATENT AND TRADEMARK OFFICE
CERTIFICATE OF CORRECTION

PATENT NO. : 9,024,044 B2
APPLICATION NO. : 13/517805
DATED : May 5, 2015
INVENTOR(S) : Takahiro Koshiba et al.

It is certified that error appears in the above-identified patent and that said Letters Patent is hereby corrected as shown below:

On the title page, Item (75), the Inventors' Information is incorrect. Item (75) should read:

--(75) Inventors: Takahiro Koshiba, Kawasaki-shi (JP);
Munetaka Tokumasu, Kawasaki-shi (JP);
Koji Ohsumi, Kawasaki-shi (JP);
Tamotsu Suzuki, Kawasaki-shi (JP)--

Signed and Sealed this
Seventh Day of July, 2015

Michelle K. Lee
*Director of the United States Patent and Trademark Office*

UNITED STATES PATENT AND TRADEMARK OFFICE
CERTIFICATE OF CORRECTION

PATENT NO. : 9,024,044 B2
APPLICATION NO. : 13/517805
DATED : May 5, 2015
INVENTOR(S) : Takahiro Koshiba et al.

Page 1 of 2

It is certified that error appears in the above-identified patent and that said Letters Patent is hereby corrected as shown below:

Specification

Column 26, line 34, "l-aspartic" should read --L-aspartic--.

Column 27, line 62, "l-aspartic" should read --L-aspartic--.

Column 28, line 25, "l-aspartic" should read --L-aspartic--.

Column 28, line 56, "l-aspartic" should read --L-aspartic--.

Column 29, lines 3-4, "l-valine" should read --L-valine--.

Column 30, line 40, "l-valine" should read --L-valine--.

Column 34, line 33, "pthiophen" should read --thiophen--.

Column 35, line 48, "phenoxycarbonyethiophen" should read --phenoxycarbonyl)thiophen--.

Column 36, line 26, "N allyl" should read --N-allyl--.

Signed and Sealed this
Twelfth Day of April, 2016

Michelle K. Lee
*Director of the United States Patent and Trademark Office*

CERTIFICATE OF CORRECTION (continued)
U.S. Pat. No. 9,024,044 B2

Claims

Claim 1, Column 79, line 23, " 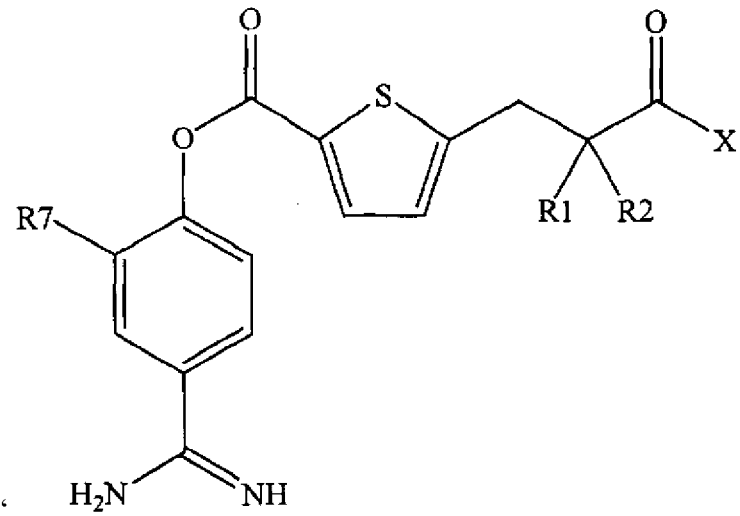 "

should read -- 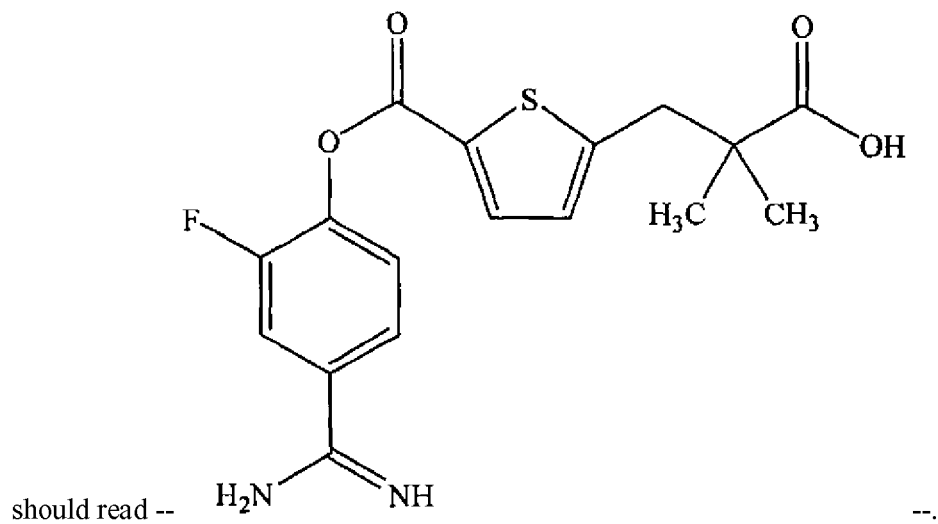 --.